(12) United States Patent
Uchiyama

(10) Patent No.: US 9,476,849 B2
(45) Date of Patent: Oct. 25, 2016

(54) BIOSENSOR SYSTEM AND METHOD FOR MEASURING CONCENTRATION OF ANALYTE

(75) Inventor: Motonori Uchiyama, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 481 days.

(21) Appl. No.: 13/262,979

(22) PCT Filed: May 20, 2010

(86) PCT No.: PCT/JP2010/003411
§ 371 (c)(1),
(2), (4) Date: Oct. 5, 2011

(87) PCT Pub. No.: WO2010/137266
PCT Pub. Date: Dec. 2, 2010

(65) Prior Publication Data
US 2012/0028282 A1    Feb. 2, 2012

(30) Foreign Application Priority Data

May 29, 2009    (JP) ................................. 2009-131248

(51) Int. Cl.
*G01N 27/327*    (2006.01)
*C12Q 1/00*    (2006.01)

(52) U.S. Cl.
CPC .......... *G01N 27/3274* (2013.01); *C12Q 1/004* (2013.01); *C12Q 1/006* (2013.01)

(58) Field of Classification Search
CPC ........................... G01N 27/00; G01N 33/483
USPC ................................................ 436/150, 149
See application file for complete search history.

(56) References Cited

U.S. PATENT DOCUMENTS

| | | | |
|---|---|---|---|
| 6,885,196 B2 | 4/2005 | Taniike et al. | |
| 7,232,510 B2 | 6/2007 | Miyazaki et al. | |
| 7,347,926 B2 | 3/2008 | Morita et al. | |
| 7,780,828 B2 | 8/2010 | Yamaoka et al. | |

(Continued)

FOREIGN PATENT DOCUMENTS

| | | |
|---|---|---|
| CN | 1 522 365 | 8/2004 |
| CN | 1 729 394 | 2/2006 |

(Continued)

OTHER PUBLICATIONS

"Fick's laws of diffusion" accessed by examiner on Aug. 27, 2014 at http://en.wikipedia.org/wiki/Fick's_laws_of_diffusion.*

(Continued)

*Primary Examiner* — Lyle Alexander
*Assistant Examiner* — Emily Berkeley
(74) *Attorney, Agent, or Firm* — Wenderoth, Lind & Ponack, L.L.P.

(57) ABSTRACT

A biosensor system can comprise a sensor chip and a measurement device. The sensor chip comprises a capillary and electrodes disposed within the capillary. The height of the capillary is set to be less than the maximum value of the sum of the diffusion distance of an electron-transfer mediator and the diffusion distance of an analyte at the upper limit of the measurement guaranteed temperature of the biosensor system. The measurement device applies an open circuit voltage, a voltage that is lower than during concentration measurement, or the like to the electrodes of the sensor chip.

9 Claims, 69 Drawing Sheets

(56) References Cited

U.S. PATENT DOCUMENTS

| | | |
|---|---|---|
| 7,850,839 B2 | 12/2010 | Miyazaki et al. |
| 8,097,147 B2 | 1/2012 | Miyazaki et al. |
| 8,101,063 B2 | 1/2012 | Miyazaki et al. |
| 8,298,400 B2 | 10/2012 | Miyazaki et al. |
| 8,425,757 B2 | 4/2013 | Wu et al. |
| 2003/0032875 A1* | 2/2003 | Taniike .......... C12Q 1/005 600/368 |
| 2003/0159945 A1* | 8/2003 | Miyazaki et al. ......... 205/777.5 |
| 2004/0259264 A1 | 12/2004 | Morita et al. |
| 2006/0175206 A1 | 8/2006 | Miyazaki et al. |
| 2006/0175207 A1 | 8/2006 | Miyazaki et al. |
| 2006/0231396 A1* | 10/2006 | Yamaoka .............. 204/403.14 |
| 2008/0110754 A1 | 5/2008 | Miyazaki et al. |
| 2008/0173552 A1 | 7/2008 | Wu et al. |
| 2009/0017483 A1 | 1/2009 | Yamaoka et al. |
| 2009/0301899 A1* | 12/2009 | Hodges et al. ........... 205/777.5 |
| 2010/0252454 A1 | 10/2010 | Miyazaki et al. |
| 2010/0320097 A1 | 12/2010 | Miyazaki et al. |
| 2011/0132776 A1 | 6/2011 | Miyazaki et al. |
| 2011/0132777 A1 | 6/2011 | Miyazaki et al. |
| 2012/0043227 A1 | 2/2012 | Miyazaki et al. |
| 2013/0020208 A1 | 1/2013 | Miyazaki et al. |
| 2013/0256156 A1 | 10/2013 | Wu et al. |

FOREIGN PATENT DOCUMENTS

| | | |
|---|---|---|
| CN | 1 311 233 | 4/2007 |
| CN | 100 339 701 | 9/2007 |
| CN | 100 346 158 | 10/2007 |
| CN | 101 163 963 | 4/2008 |
| EP | 1 577 665 | 9/2005 |
| EP | 1 712 919 | 10/2006 |
| JP | 2000-162176 | 6/2000 |
| JP | 2001-21525 | 1/2001 |
| JP | 2003-156469 | 5/2003 |
| JP | 2007-33459 | 2/2007 |
| JP | 2009-503452 | 1/2009 |
| WO | 02/08743 | 1/2002 |
| WO | 03/036285 | 5/2003 |
| WO | 2004/061444 | 7/2004 |

OTHER PUBLICATIONS

WikiBooks "Electronics/Voltage, Current, and Power" 2007 (https://web.archive.org/web/20071126064235/http://en.wikibooks.org/wiki/Electronics/Voltage%2C_Current%2C_and_Power).*

Chinese Office Action issued May 24, 2013 in corresponding Chinese Application No. 201080017884.1.

International Search Report issued Aug. 24, 2010 in International (PCT) Application No. PCT/JP2010/003411.

Supplementary European Search Report issued Jul. 18, 2014 in corresponding Application No. EP 10 78 0227.

* cited by examiner

BIOSENSOR SYSTEM AND METHOD FOR MEASURING CONCENTRATION OF ANALYTE

TECHNICAL FIELD

The present invention relates to a biosensor system and to a method for measuring the concentration of an analyte.

BACKGROUND ART

A portable biosensor system comprising a measurement device with a computer, and a sensor chip that can be installed in this measurement device, has been used in the past to measure the concentration of an analyte in a blood sample, such as the blood glucose concentration (glucose value). The concentration of the analyte is calculated on the basis of the amount of oxidized product and reduced product produced by an enzyme cycling reaction via a redox enzyme in which the analyte serves as the substrate. The speed of the enzyme cycling reaction depends on the temperature of the environment in which the reaction takes place (the reaction temperature). Accordingly, a biosensor system has been proposed that comprises a function of correcting the concentration of an analyte on the basis of the reaction temperature. The reaction temperature is measured, for example, by a temperature sensor disposed in the measurement device (Patent Literature 1).

CITATION LIST

Patent Literature

Patent Literature 1: Japanese Laid-Open Patent Application 2003-156469

SUMMARY

Technical Problem

With the biosensor system of Patent Literature 1, the internal temperature of the measurement device is measured with a temperature sensor. Thus, the measured temperature does not accurately reflect the temperature of the blood sample. Accordingly, error may occur in the measurement of the analyte concentration.

It is an object of the present invention to provide a biosensor system and a concentration measurement method with which error is less likely to be caused by temperature changes.

Solution to Problem

The biosensor system pertaining to a first aspect of the present invention is a biosensor system with which the concentration of an analyte in a liquid sample is measured using a redox enzyme or an electron-transfer mediator, said biosensor system comprising a sensor chip comprising a capillary into which a liquid sample is introduced, whose height is less than the maximum value of the sum of the diffusion distance of the electron-transfer mediator and the diffusion distance of the analyte at the upper limit of the measurement guaranteed temperature of the biosensor system, a plurality of electrodes disposed within the capillary, and a reagent layer that is disposed within the capillary and includes the electron-transfer mediator; a first voltage applicator that applies a first voltage to the electrodes; a concentration measurement section that measures the concentration of the analyte on the basis of the value of the current flowing through the liquid sample during the first voltage application; and a second voltage applicator that applies a second voltage to the electrodes prior to the application of the first voltage, so that the effect of the temperature of the liquid sample on the measurement results of the concentration measurement section will be diminished.

The measurement method pertaining to a second aspect of the present invention is a method for measuring the concentration of an analyte in a liquid sample using a redox enzyme or an electron-transfer mediator, which is executed by a biosensor system having a sensor chip comprising a capillary into which a liquid sample is introduced, whose height is less than the maximum value of the sum of the diffusion distance of the electron-transfer mediator and the diffusion distance of the analyte at the upper limit of the measurement guaranteed temperature of the biosensor system, a plurality of electrodes disposed within the capillary, and a reagent layer that is disposed within the capillary and includes the electron-transfer mediator, said measurement method comprising a first voltage application step of applying a first voltage to the electrodes, a current detection step of detecting the value of current flowing through the liquid sample during the application of the first voltage, a concentration measurement step of measuring the concentration of the analyte on the basis of the current value, and a second voltage application step of applying a second voltage to the electrodes prior to the detection of the current value, so that the temperature of the liquid sample will have less effect on the measurement results of the concentration measurement section.

Advantageous Effects

With the biosensor system and measurement method pertaining to the present invention, the distance that an analyte in a liquid sample can move by diffusion is limited by a capillary. Furthermore, a second voltage is applied to electrodes before a first voltage is applied, which reduces variance in the measurement result caused by temperature.

BRIEF DESCRIPTION OF DRAWINGS

FIG. 40B is a graph of the response current value under the same conditions as in FIG. 39A, except that the height of the capillary is 59 μm;

FIG. 40C is a graph of the response current value under the same conditions as in FIG. 39A, except that the height of the capillary is 49 μm;

FIG. 40D is a graph of the response current value under the same conditions as in FIG. 39A, except that the height of the capillary is 33 μm;

FIG. 41A is a graph of the response current value under the same conditions as in FIG. 33A, except that the voltage application conditions are open (3 seconds)—250 mV;

FIG. 41B is a graph of the response current value under the same conditions as in FIG. 41A, except that the height of the capillary is 104 μm;

FIG. 41C is a graph of the response current value under the same conditions as in FIG. 41A, except that the height of the capillary is 90 μm;

FIG. 41D is a graph of the response current value under the same conditions as in FIG. 41A, except that the height of the capillary is 82 μm;

FIG. 42A is a graph of the response current value under the same conditions as in FIG. 41A, except that the height of the capillary is 69 μm;

FIG. 42B is a graph of the response current value under the same conditions as in FIG. 41A, except that the height of the capillary is 59 μm;

FIG. 42C is a graph of the response current value under the same conditions as in FIG. 41A, except that the height of the capillary is 49 μm;

FIG. 42D is a graph of the response current value under the same conditions as in FIG. 41A, except that the height of the capillary is 33 μm;

FIG. 43A is a graph of the response current value under the same conditions as in FIG. 33A, except that the voltage application conditions are open (4 seconds)—250 mV;

Figure 33A:
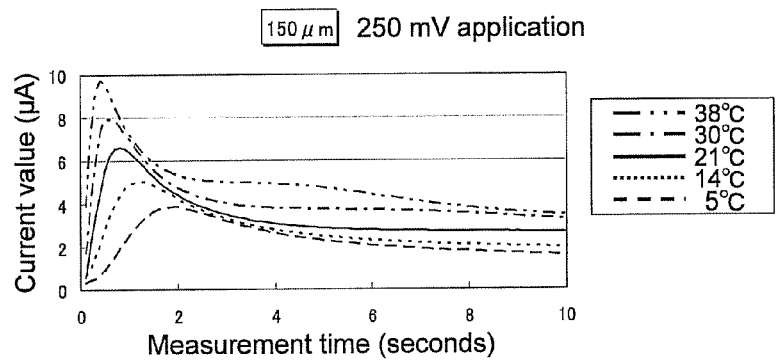
FIG. 33A is a graph of the response current value when the glucose concentration of the sample is 100 mg/dL, neither the application of open circuit voltage nor the application of low voltage is executed, the applied voltage is 250 mV, and the height of the capillary is 150 μm.
Figure 33B:
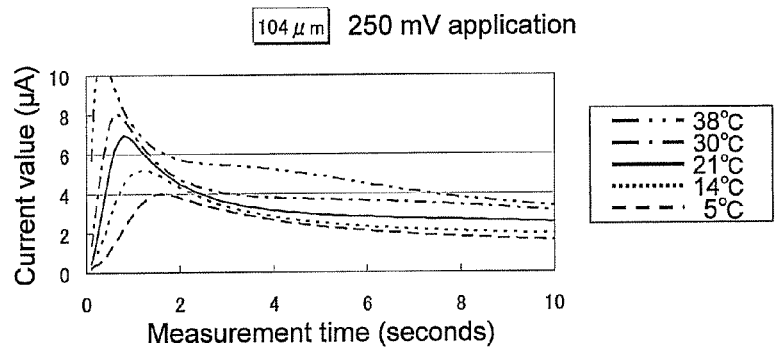
FIG. 33B is a graph of the response current value under the same conditions as in FIG. 33A, except that the height of the capillary is 104 μm.
Figure 33C:
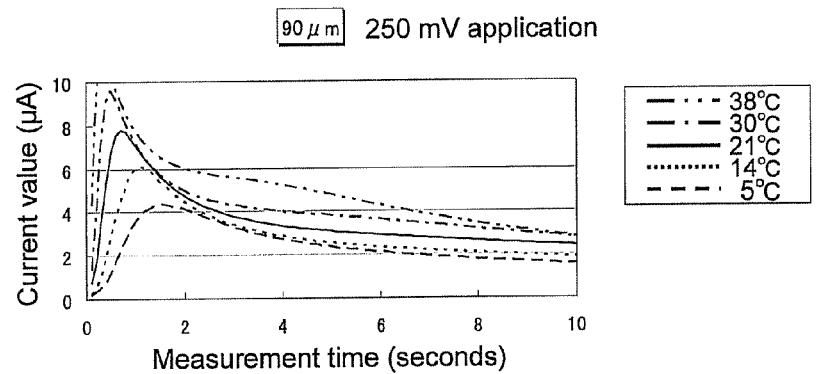
FIG. 33C is a graph of the response current value under the same conditions as in FIG. 33A, except that the height of the capillary is 90 μm.
Figure 33D:
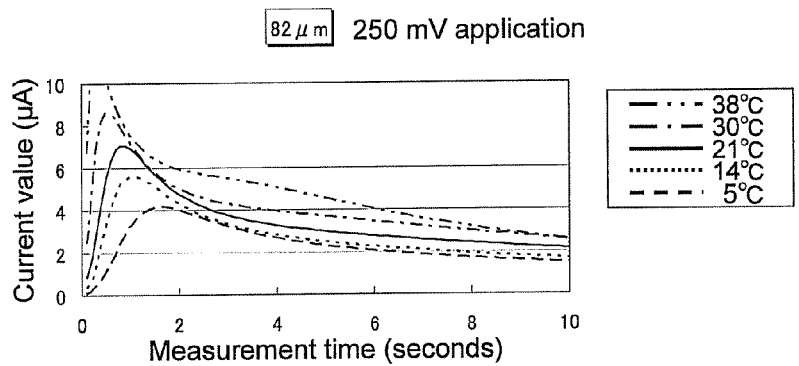
FIG. 33D is a graph of the response current value under the same conditions as in FIG. 33A, except that the height of the capillary is 82 μm.
Figure 34A:
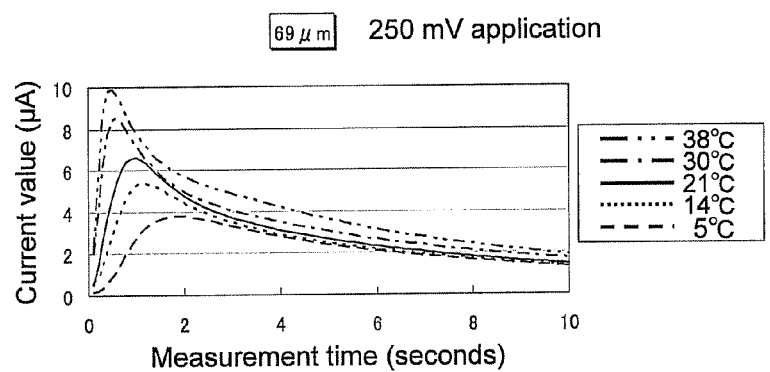
FIG. 34A is a graph of the response current value under the same conditions as in FIG. 33A, except that the height of the capillary is 69 μm.
Figure 34B:
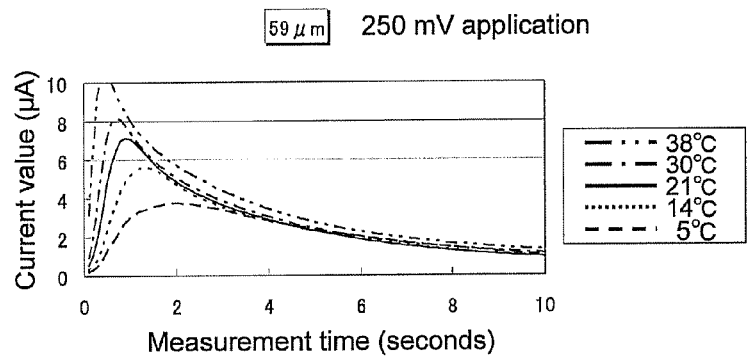
FIG. 34B is a graph of the response current value under the same conditions as in FIG. 33A, except that the height of the capillary is 59 μm.
Figure 34C:
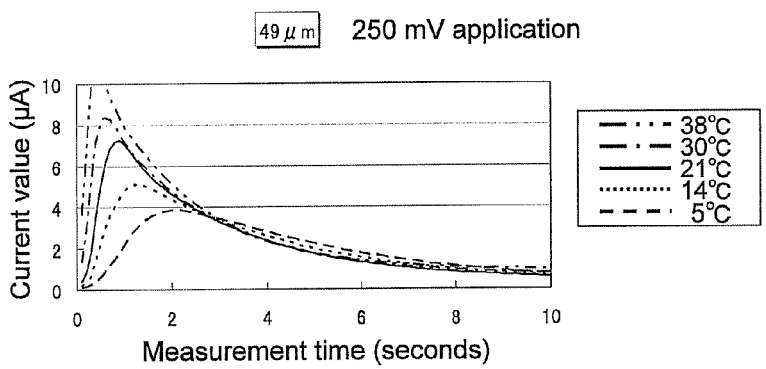
FIG. 34C is a graph of the response current value under the same conditions as in FIG. 33A, except that the height of the capillary is 49 μm.
Figure 34D:
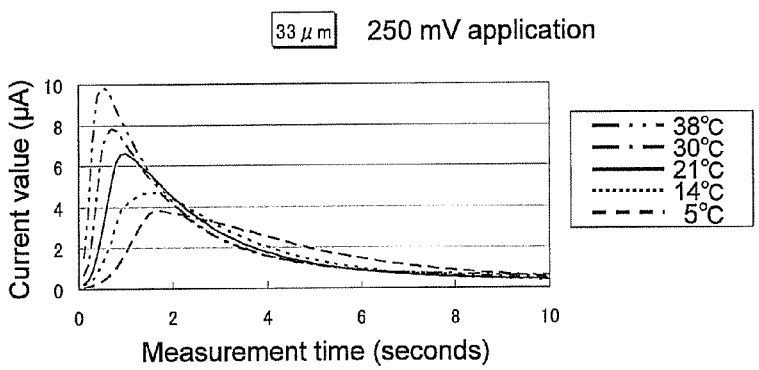
FIG. 34D is a graph of the response current value under the same conditions as in FIG. 33A, except that the height of the capillary is 33 μm.
Figure 35A:
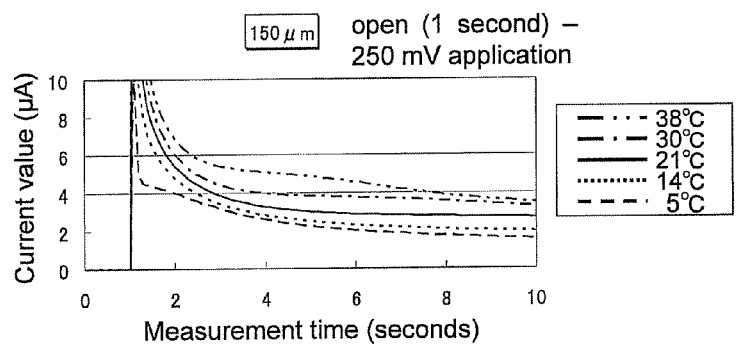
FIG. 35A is a graph of the response current value under the same conditions as in FIG. 33A, except that the voltage application conditions are open (1 second)—250 mV.
Figure 35B:
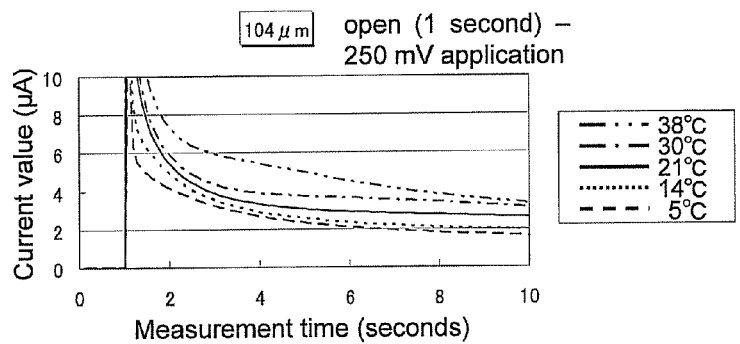
FIG. 35B is a graph of the response current value under the same conditions as in FIG. 35A, except that the height of the capillary is 104 μm.
Figure 35C:
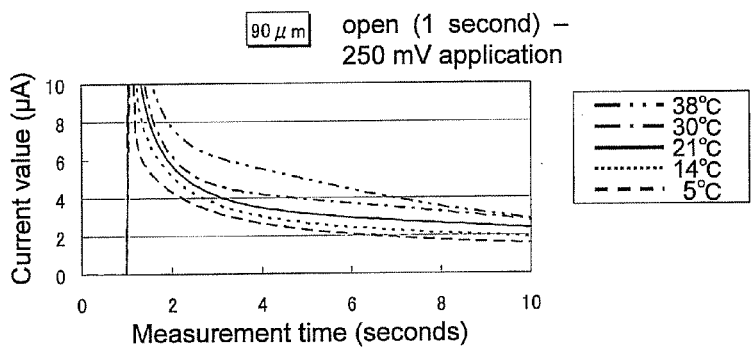
FIG. 35C is a graph of the response current value under the same conditions as in FIG. 35A, except that the height of the capillary is 90 μm.
Figure 35D:
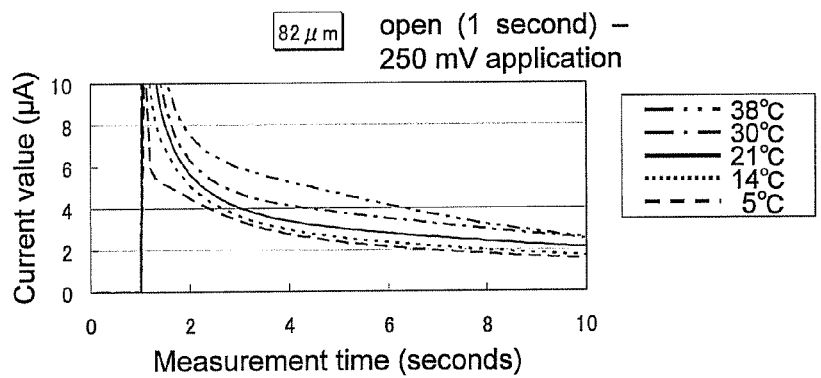
FIG. 35D is a graph of the response current value under the same conditions as in FIG. 35A, except that the height of the capillary is 82 μm.
Figure 36A:
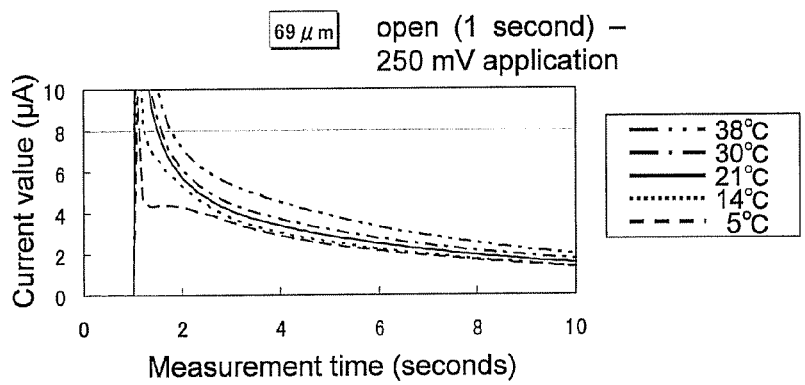
FIG. 36A is a graph of the response current value under the same conditions as in FIG. 35A, except that the height of the capillary is 69 μm.
Figure 36B:
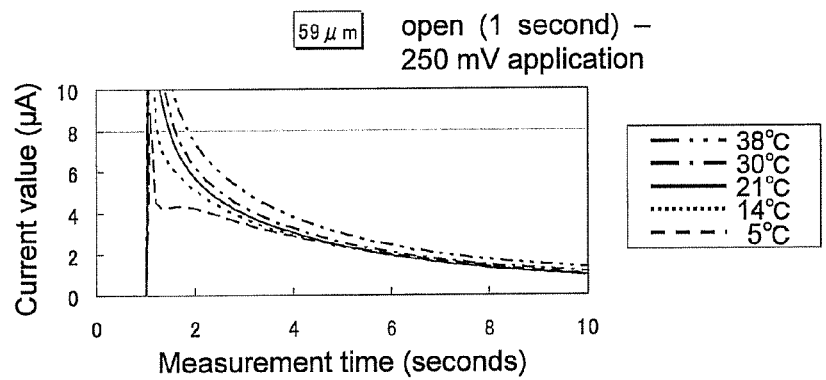
FIG. 36B is a graph of the response current value under the same conditions as in FIG. 35A, except that the height of the capillary is 59 μm.
Figure 36C:
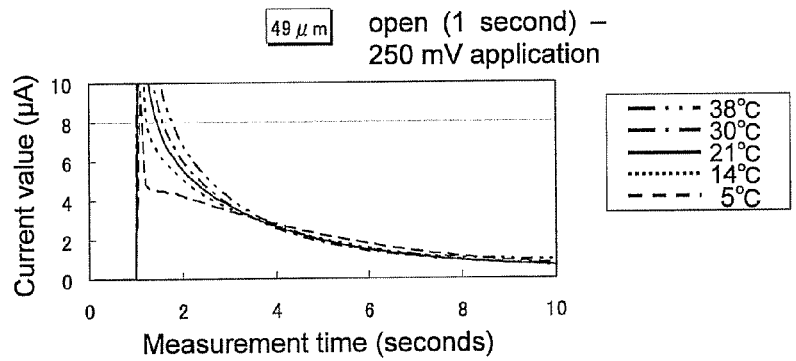
FIG. 36C is a graph of the response current value under the same conditions as in FIG. 35A, except that the height of the capillary is 49 μm.
Figure 36D:
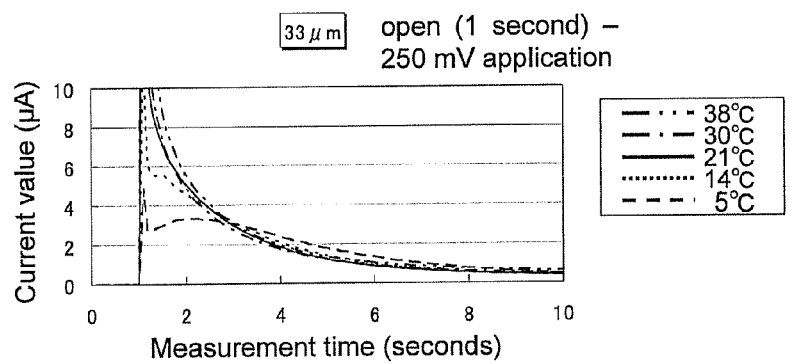
FIG. 36D is a graph of the response current value under the same conditions as in FIG. 35A, except that the height of the capillary is 33 μm.
Figure 37A:
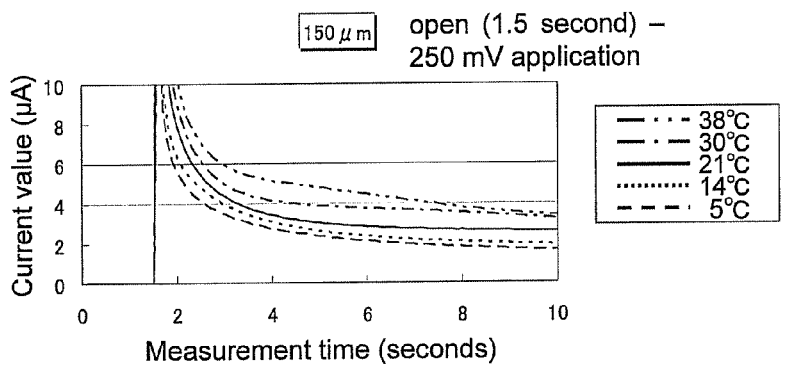
FIG. 37A is a graph of the response current value under the same conditions as in FIG. 33A, except that the voltage application conditions are open (1.5 seconds)—250 mV.
Figure 37B:
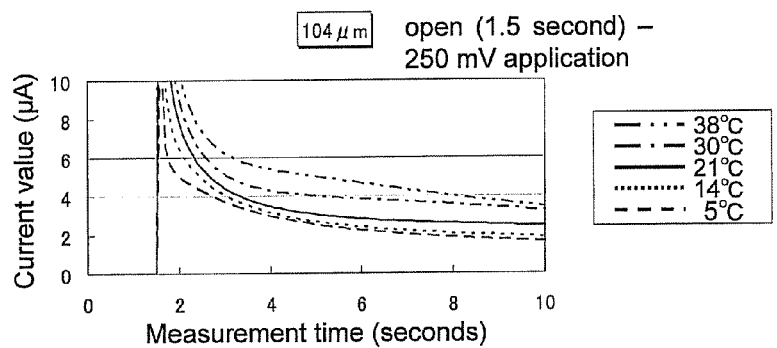
FIG. 37B is a graph of the response current value under the same conditions as in FIG. 37A, except that the height of the capillary is 104 μm.
Figure 37C:
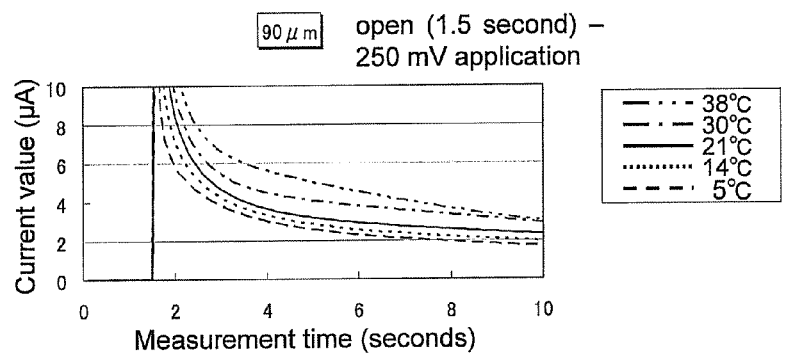
FIG. 37C is a graph of the response current value under the same conditions as in FIG. 37A, except that the height of the capillary is 90 μm.
Figure 37D:
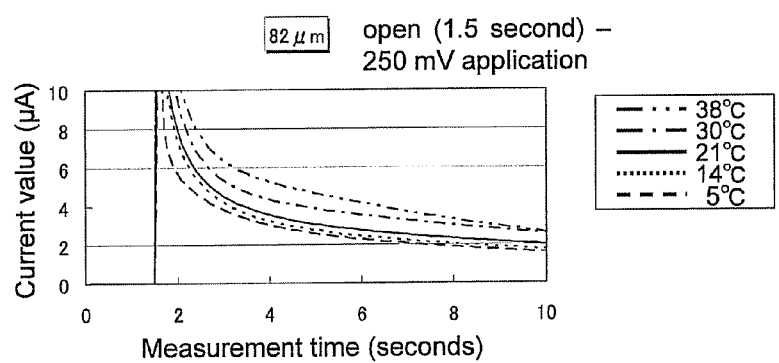
FIG. 37D is a graph of the response current value under the same conditions as in FIG. 37A, except that the height of the capillary is 82 μm.
Figure 38A:
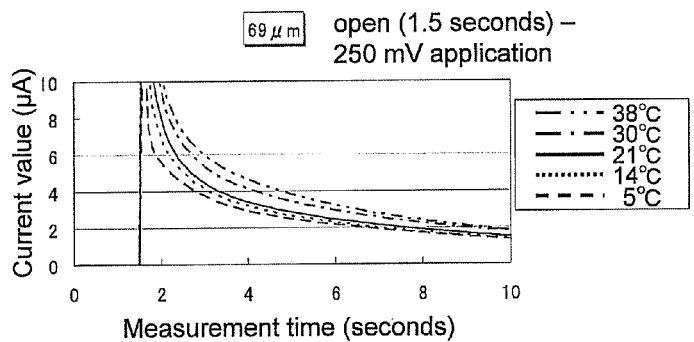
FIG. 38A is a graph of the response current value under the same conditions as in FIG. 37A, except that the height of the capillary is 69 μm.
Figure 38B:
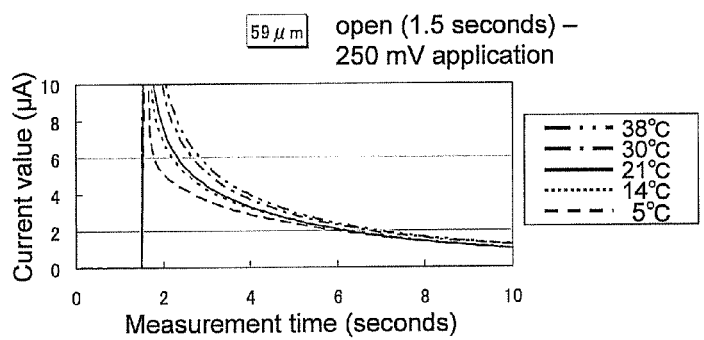
FIG. 38B is a graph of the response current value under the same conditions as in FIG. 37A, except that the height of the capillary is 59 μm.
Figure 38C:
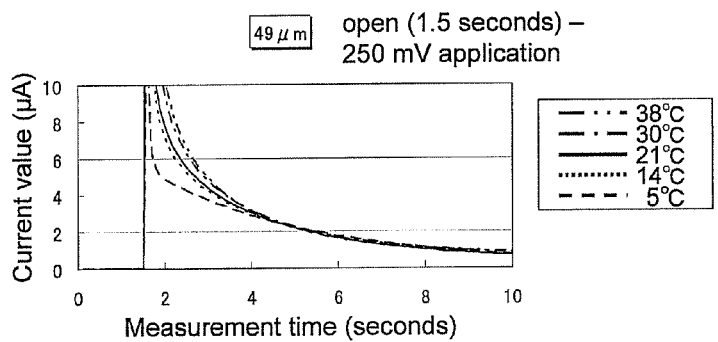
FIG. 38C is a graph of the response current value under the same conditions as in FIG. 37A, except that the height of the capillary is 49 μm.
Figure 38D:
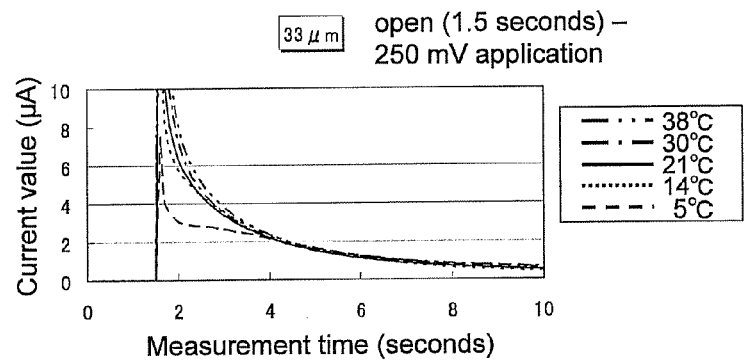
FIG. 38D is a graph of the response current value under the same conditions as in FIG. 37A, except that the height of the capillary is 33 μm.
Figure 39A:
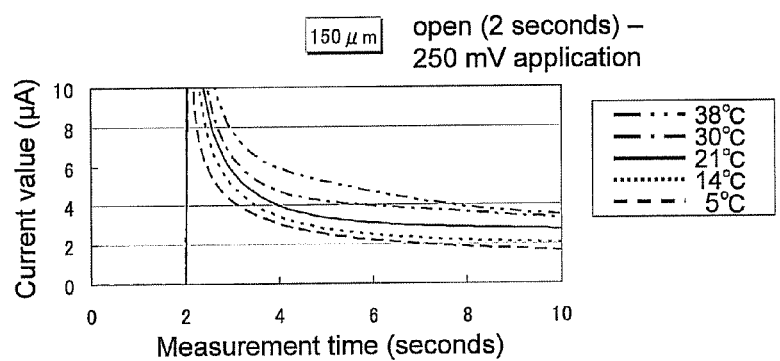
FIG. 39A is a graph of the response current value under the same conditions as in FIG. 33A, except that the voltage application conditions are open (2 seconds)—250 mV.
Figure 39B:
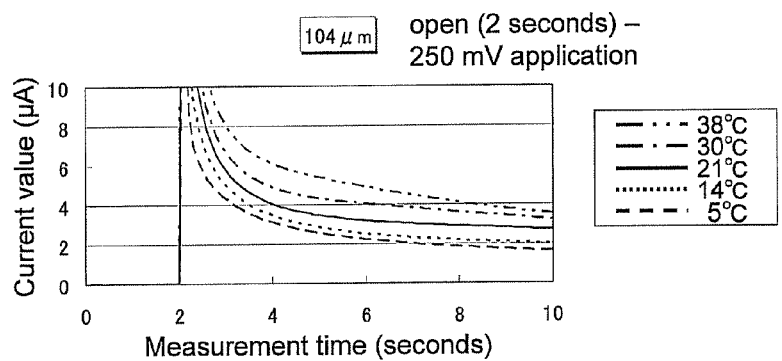
FIG. 39B is a graph of the response current value under the same conditions as in FIG. 39A, except that the height of the capillary is 104 μm.
Figure 39C:
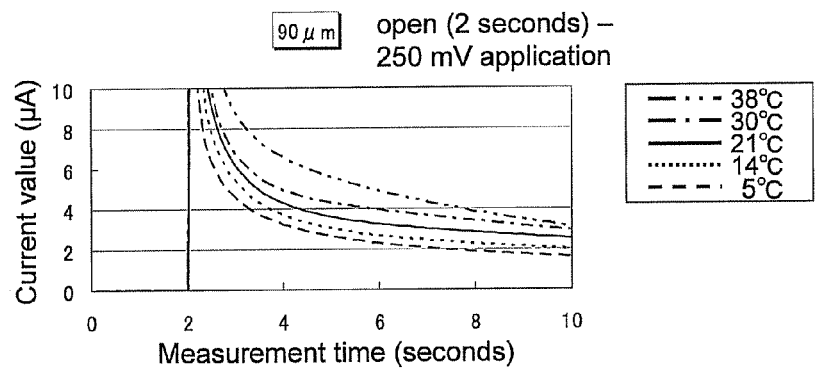
FIG. 39C is a graph of the response current value under the same conditions as in FIG. 39A, except that the height of the capillary is 90 μm.
Figure 39D:
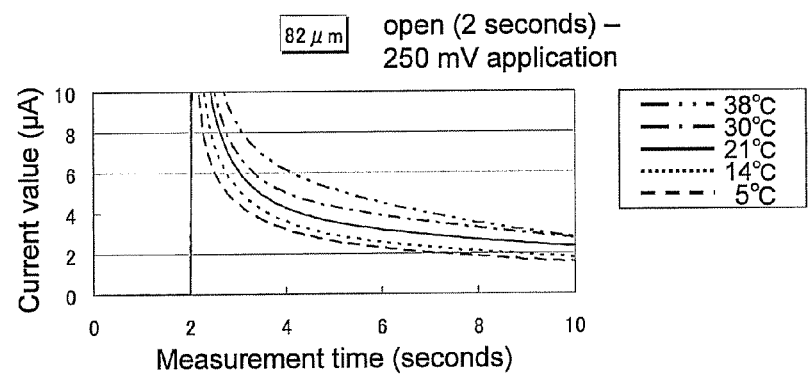
FIG. 39D is a graph of the response current value under the same conditions as in FIG. 39A, except that the height of the capillary is 82 μm.
Figure 40A:
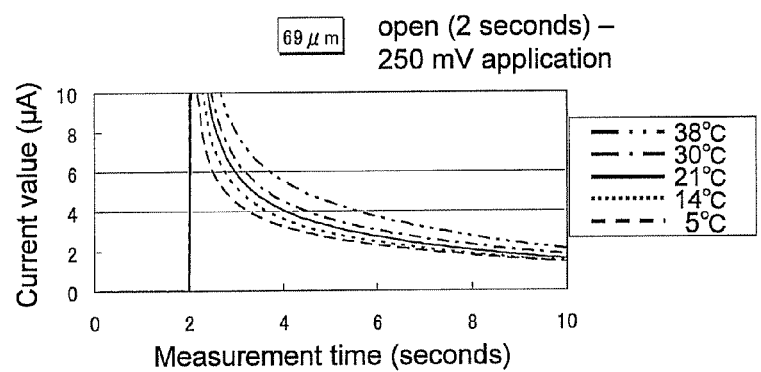
FIG. 40A is a graph of the response current value under the same conditions as in FIG. 39A, except that the height of the capillary is 69 μm.
Figure 40B:
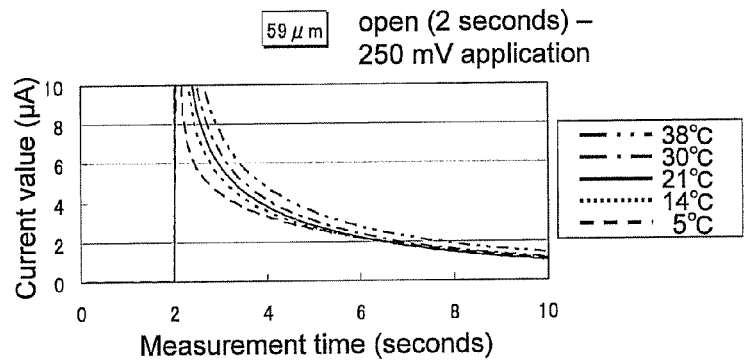
Figure 40C:
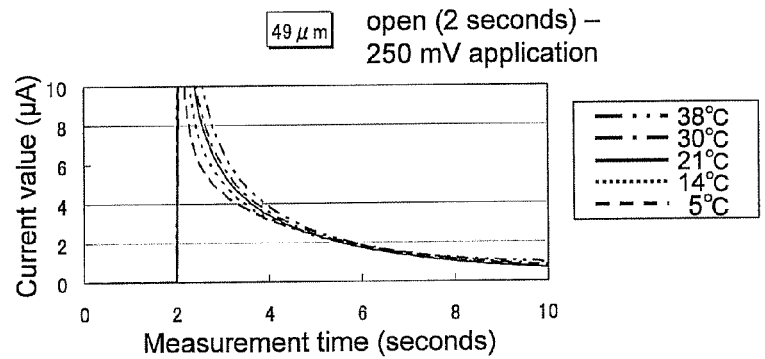
Figure 40D:
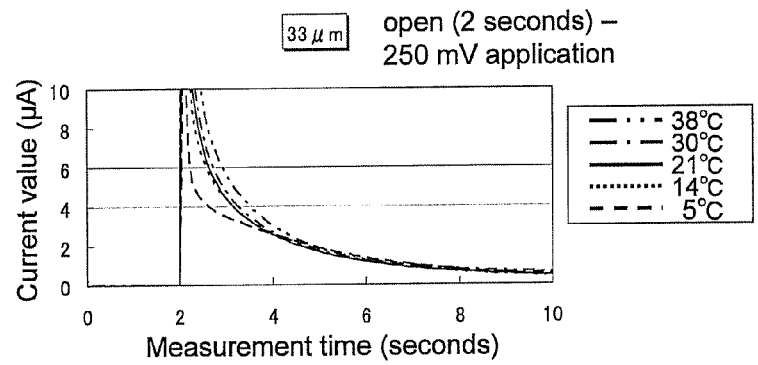
Figure 41A:
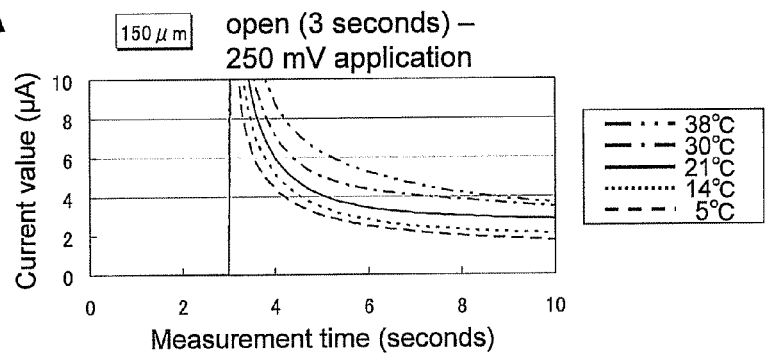
Figure 41B:
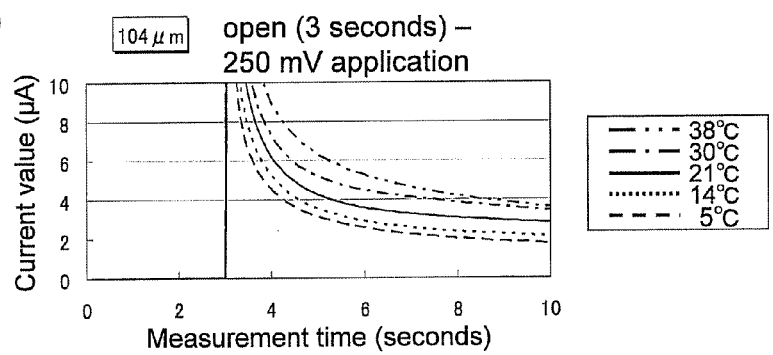
Figure 41C:
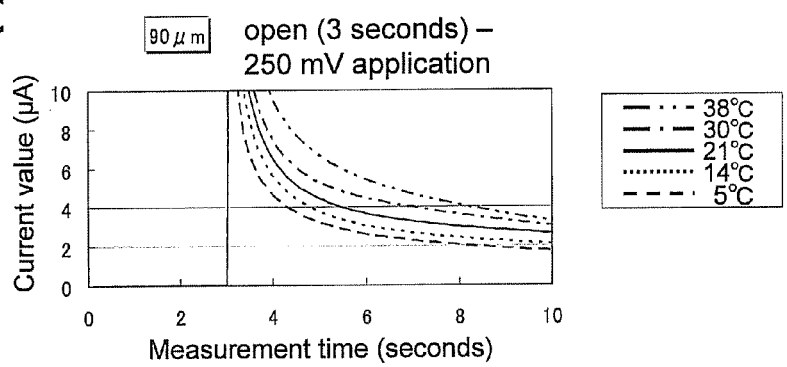
Figure 41D:
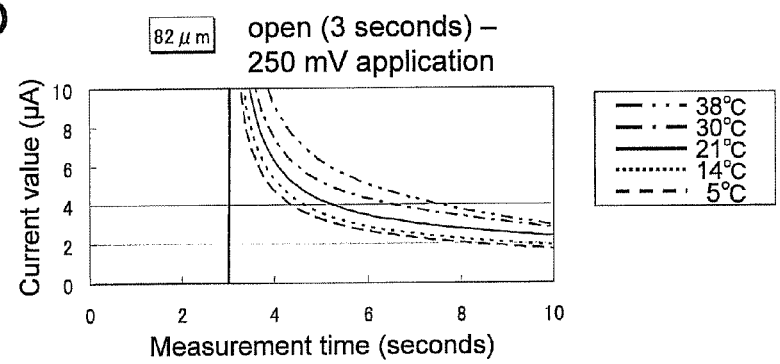
Figure 42A:
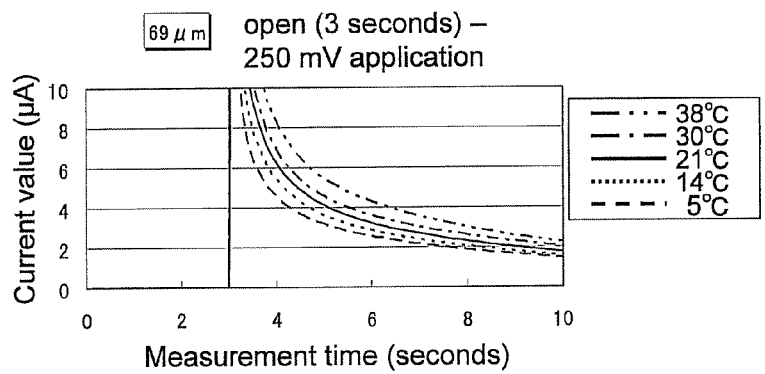
Figure 42B:
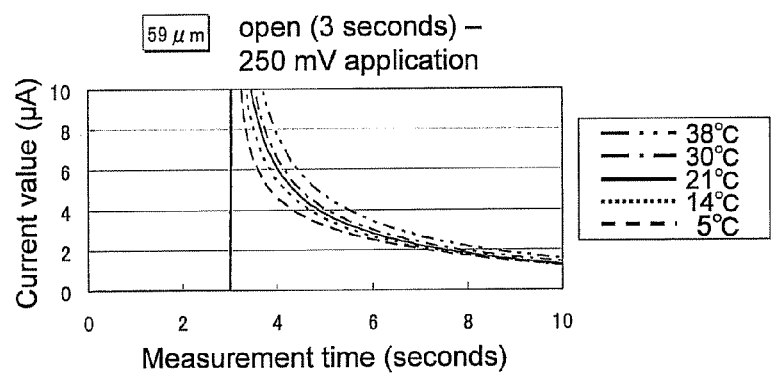
Figure 42C:
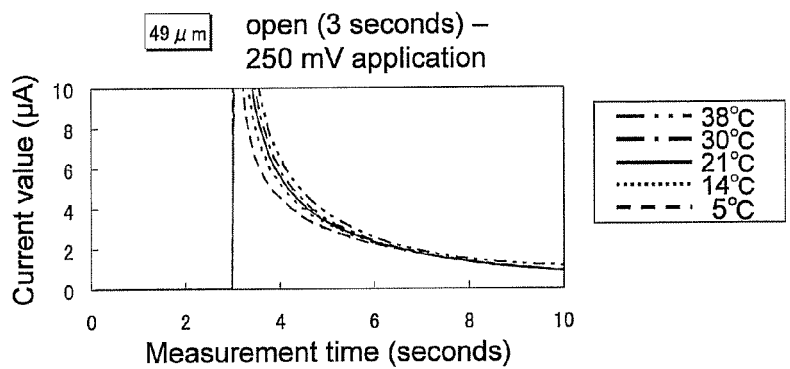
Figure 42D:
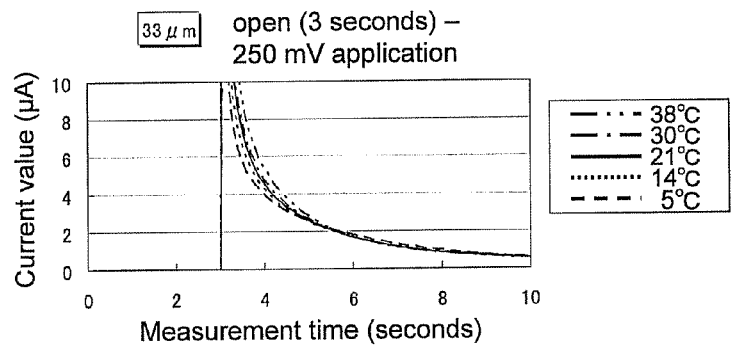
Figure 43A:
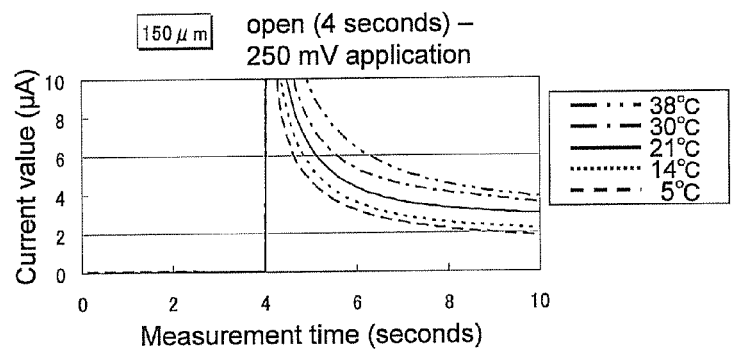
Figure 43B:
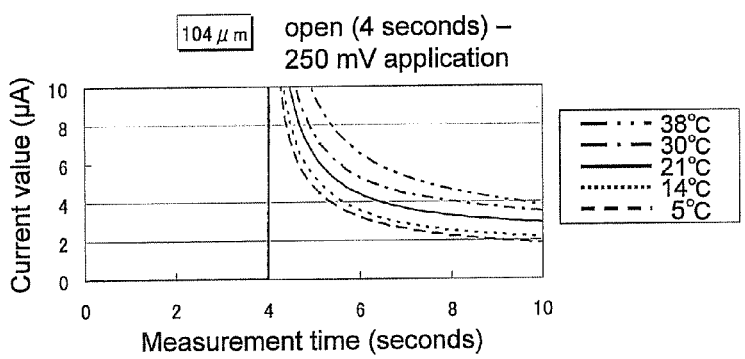
Figure 43C:
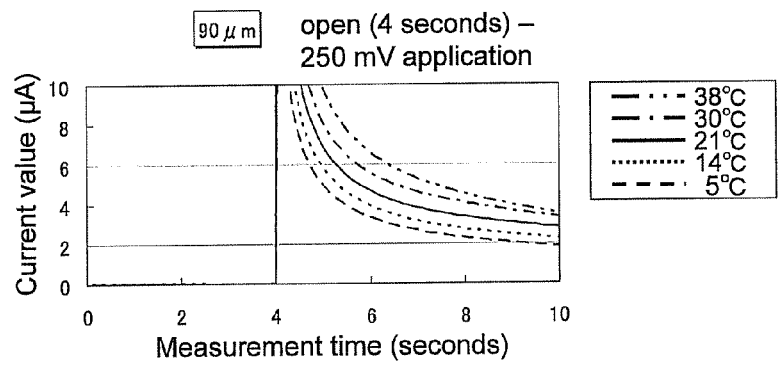
Figure 43D:
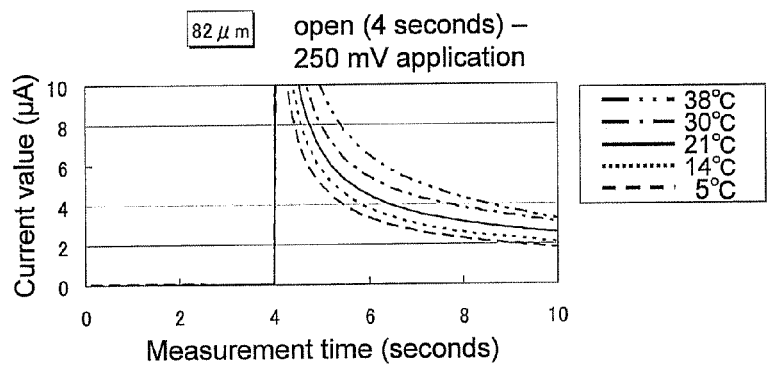
Figure 44A:
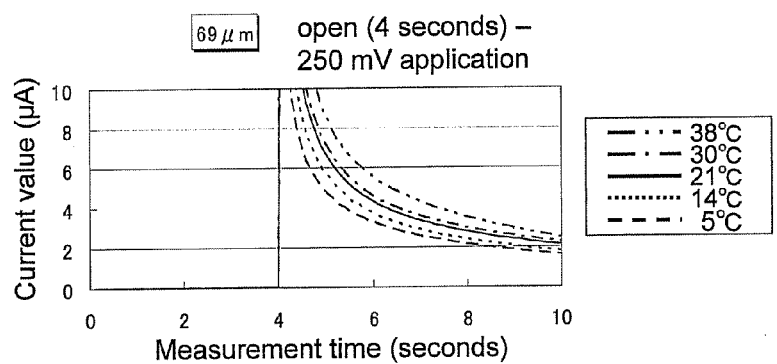
Figure 44B:
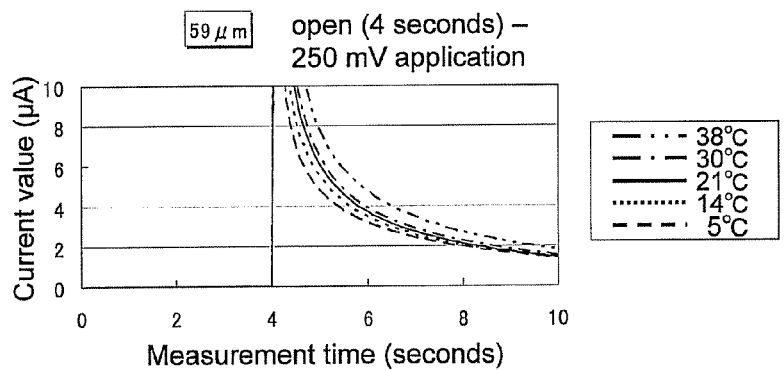
Figure 44C:
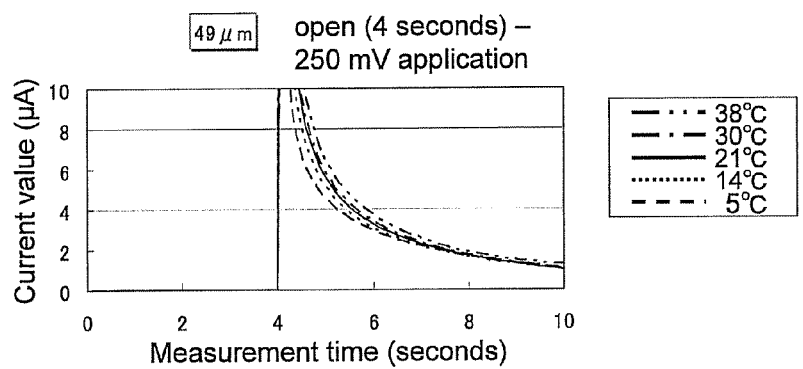
Figure 44D:
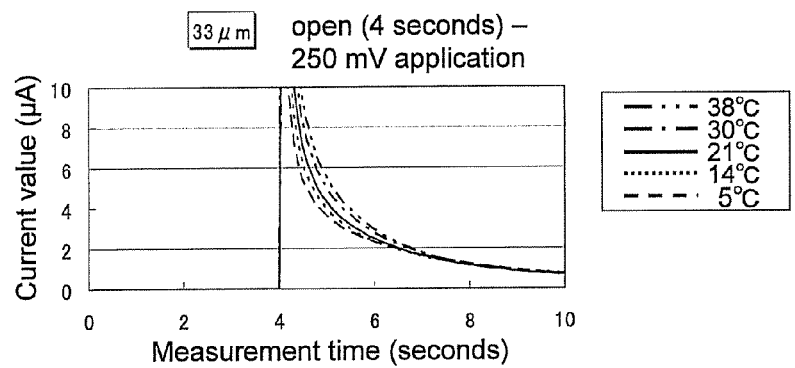
Figure 45A:
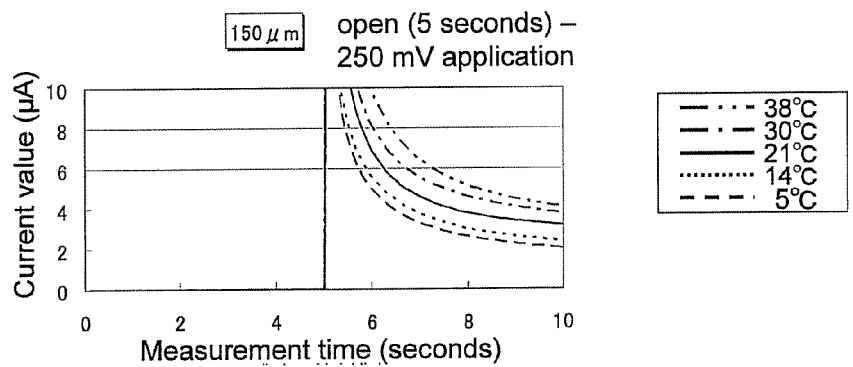
Figure 45B:
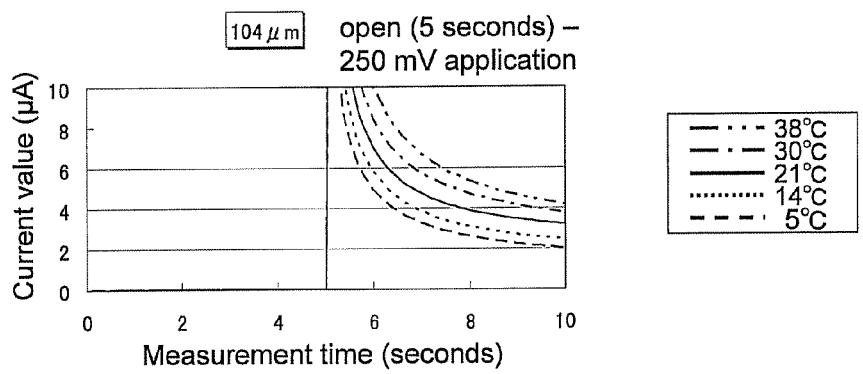
Figure 45C:
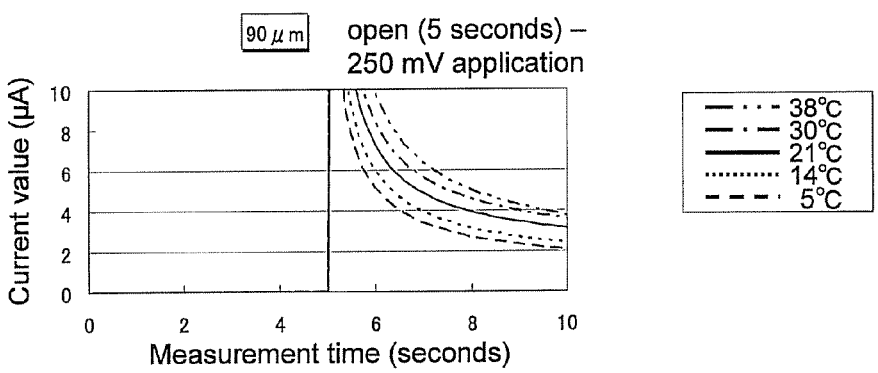
Figure 45D:
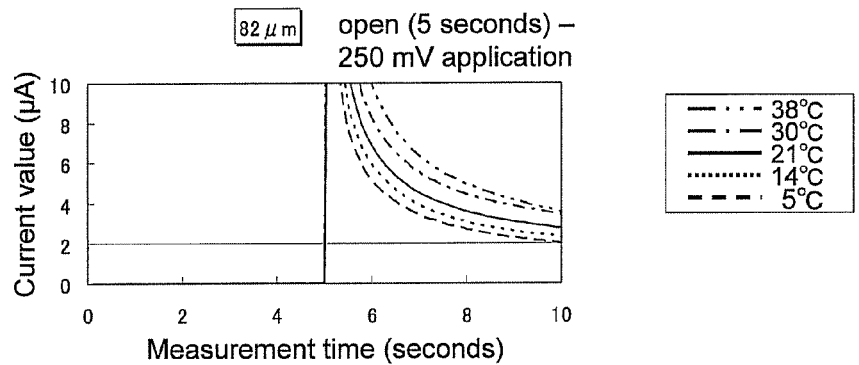
Figure 46A:
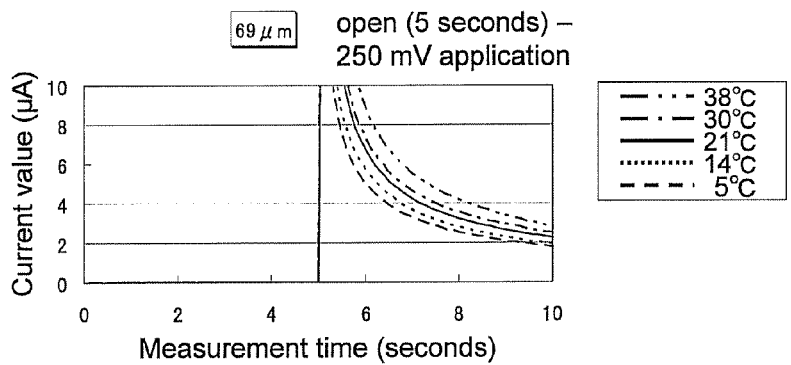
Figure 46B:
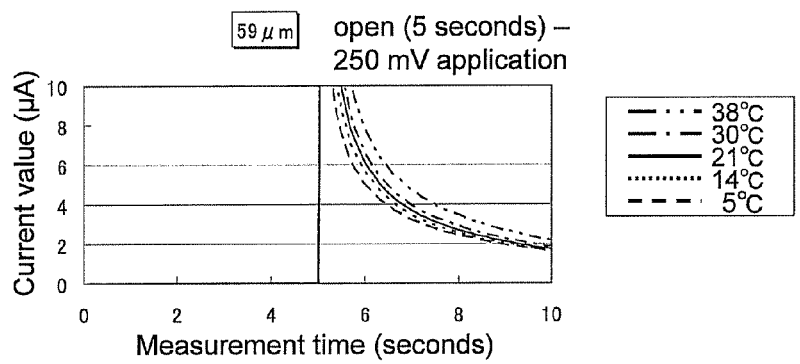
Figure 46C:
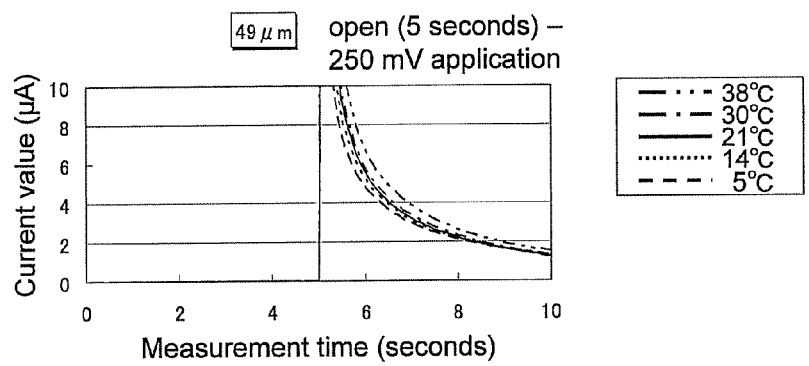
Figure 46D:
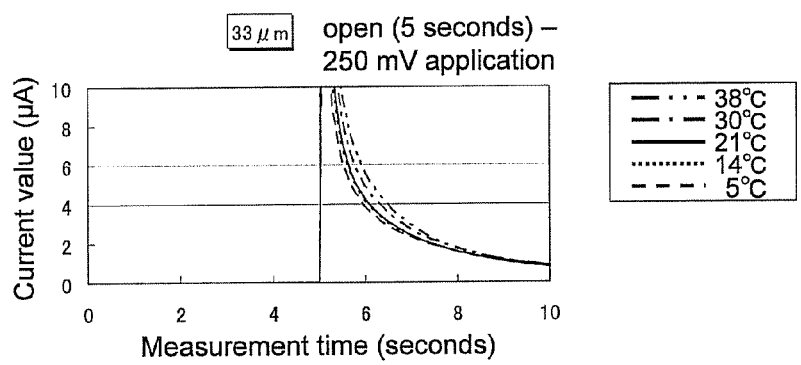
Figure 47A:
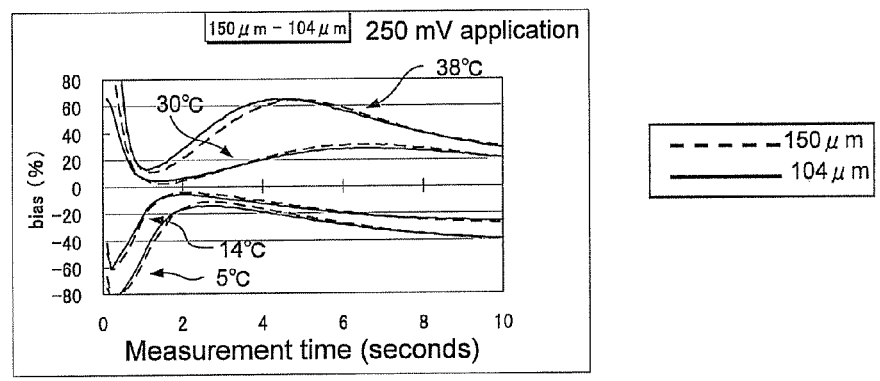
Figure 47B:
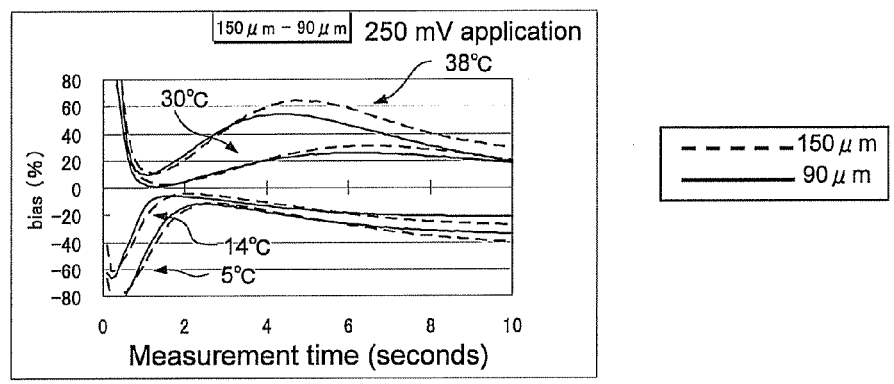
Figure 47C:
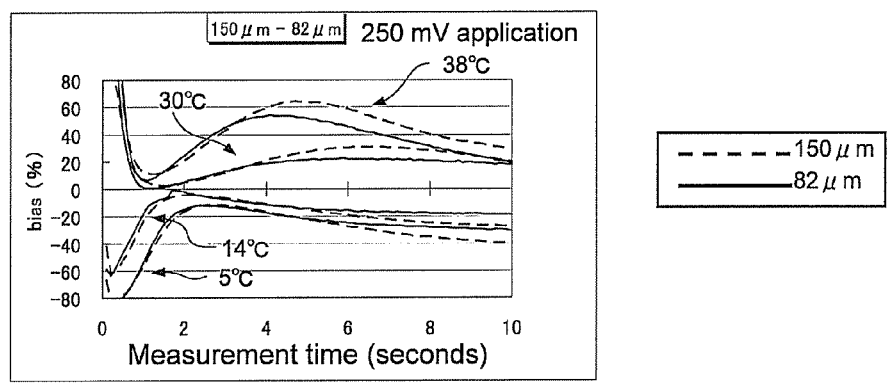

FIG. 43B is a graph of the response current value under the same conditions as in FIG. 43A, except that the height of the capillary is 104 μm;

FIG. 43C is a graph of the response current value under the same conditions as in FIG. 43A, except that the height of the capillary is 90 μm;

FIG. 43D is a graph of the response current value under the same conditions as in FIG. 43A, except that the height of the capillary is 82 μm;

FIG. 44A is a graph of the response current value under the same conditions as in FIG. 43A, except that the height of the capillary is 69 μm;

FIG. 44B is a graph of the response current value under the same conditions as in FIG. 43A, except that the height of the capillary is 59 μm;

FIG. 44C is a graph of the response current value under the same conditions as in FIG. 43A, except that the height of the capillary is 49 μm;

FIG. 44D is a graph of the response current value under the same conditions as in FIG. 43A, except that the height of the capillary is 33 μm;

FIG. 45A is a graph of the response current value under the same conditions as in FIG. 33A, except that the voltage application conditions are open (5 seconds)—250 mV;

FIG. 45B is a graph of the response current value under the same conditions as in FIG. 45A, except that the height of the capillary is 104 μm;

FIG. 45C is a graph of the response current value under the same conditions as in FIG. 45A, except that the height of the capillary is 90 μm;

FIG. 45D is a graph of the response current value under the same conditions as in FIG. 45A, except that the height of the capillary is 82 μm;

FIG. 46A is a graph of the response current value under the same conditions as in FIG. 45A, except that the height of the capillary is 69 μm;

FIG. 46B is a graph of the response current value under the same conditions as in FIG. 45A, except that the height of the capillary is 59 μm;

FIG. 46C is a graph of the response current value under the same conditions as in FIG. 45A, except that the height of the capillary is 49 μm;

FIG. 46D is a graph of the response current value under the same conditions as in FIG. 45A, except that the height of the capillary is 33 μm;

FIG. 47A is a graph of the variance in the response current values measured at 5° C., 14° C., 30° C., and 38° C. when the glucose concentration of the sample is 100 mg/dL, neither the application of open circuit voltage nor the application of low voltage is executed, the applied voltage is 250 mV, and the height of the capillary is 104 μm, using the response current value at 21° C. as a reference (the variance obtained under the same conditions, except that the height of the capillary is 150 μm, is shown for comparison);

FIG. 47B is a graph of the variance in the response current value under the same conditions as in FIG. 47A, except that the height of the capillary is 90 μm (the variance obtained under the same conditions, except that the height of the capillary is 150 μm, is shown for comparison);

FIG. 47C is a graph of the variance in the response current value under the same conditions as in FIG. 47A, except that the height of the capillary is 82 μm (the variance obtained under the same conditions, except that the height of the capillary is 150 μm, is shown for comparison)

Figure 47D:
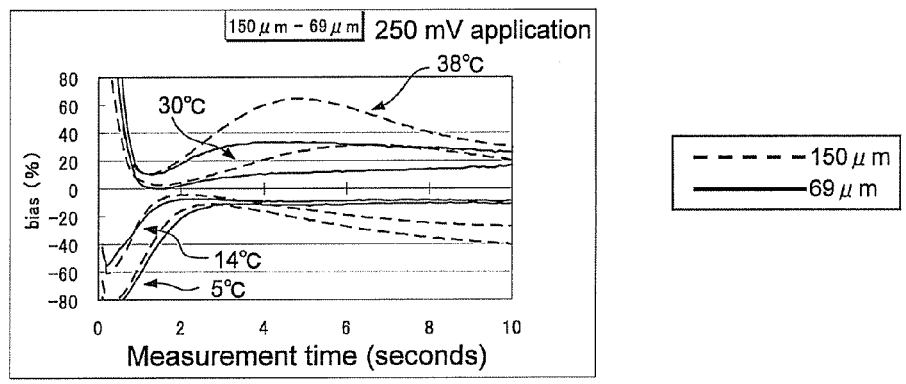

FIG. 47D is a graph of the variance in the response current value under the same conditions as in FIG. 47A, except that the height of the capillary is 69 μm (the variance obtained under the same conditions, except that the height of the capillary is 150 μm, is shown for comparison)

Figure 48A:
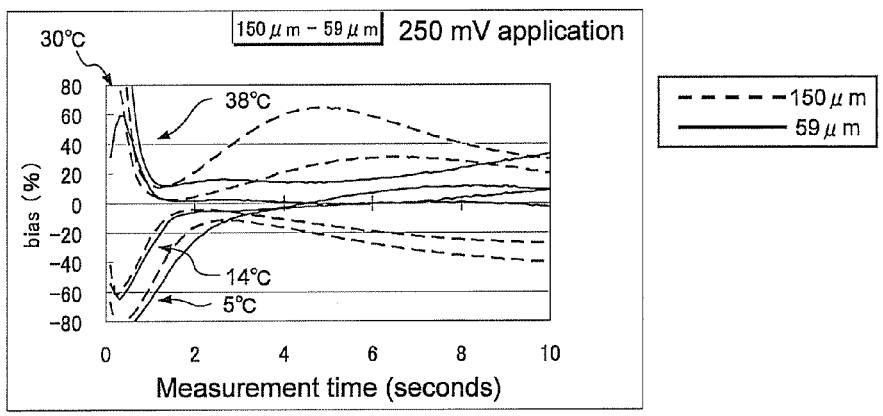
Figure 48B:
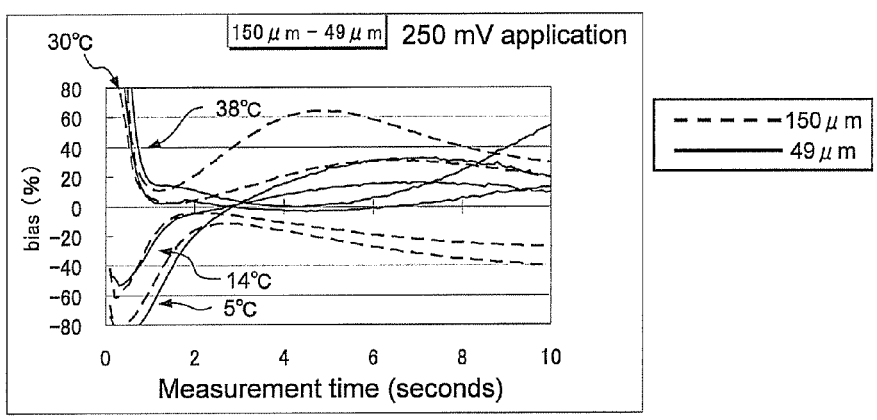
Figure 48C:
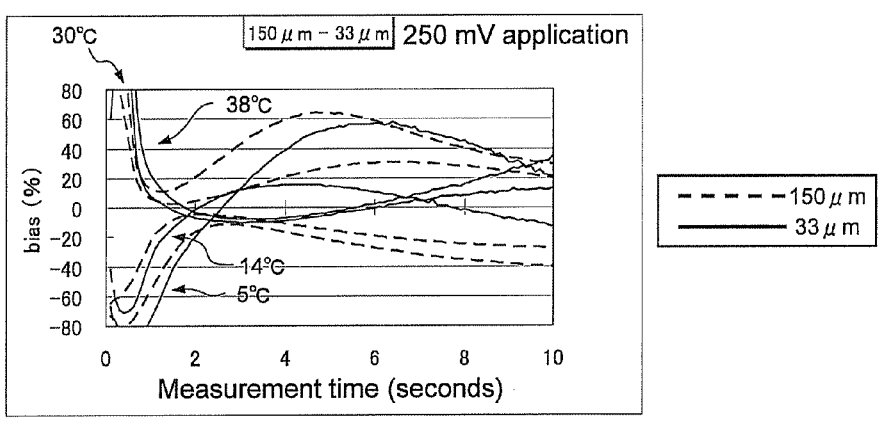
Figure 49A:
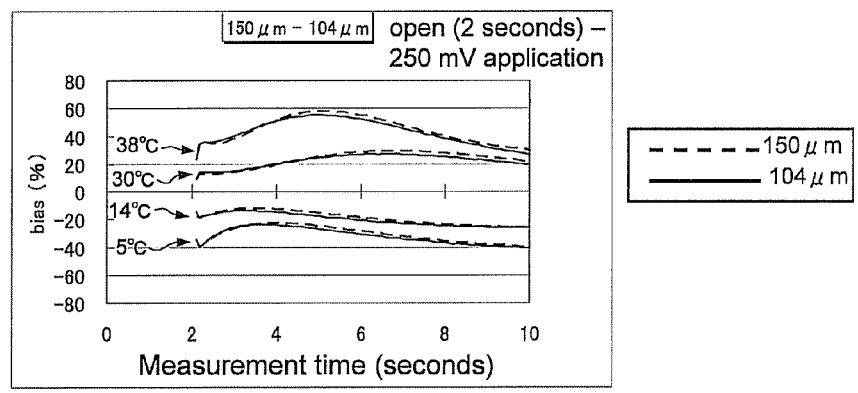
Figure 49B:
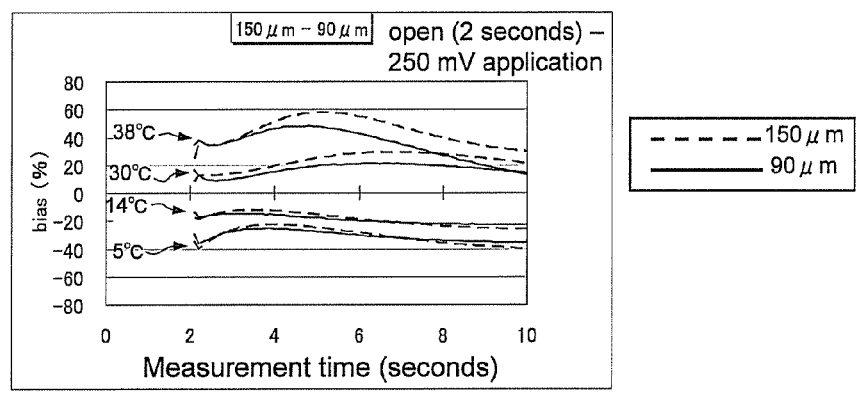
Figure 49C:
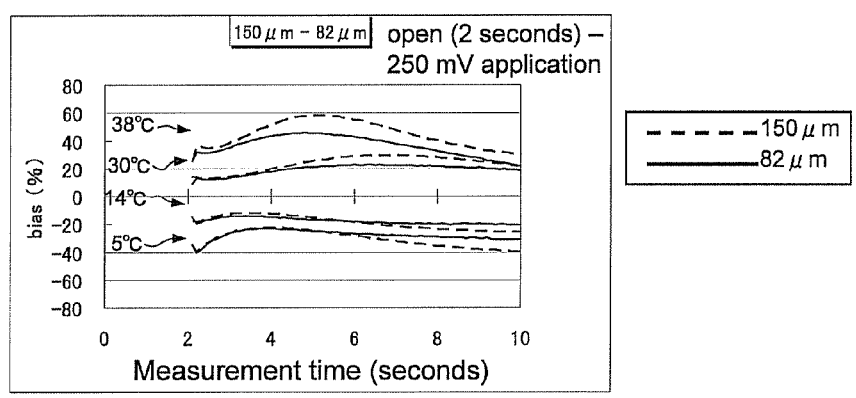
Figure 49D:
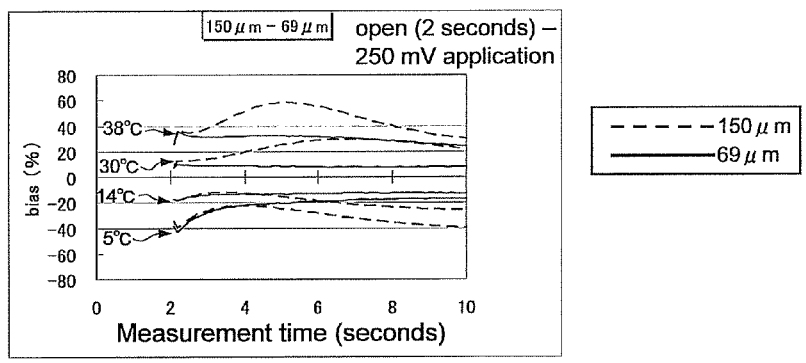
Figure 50A:
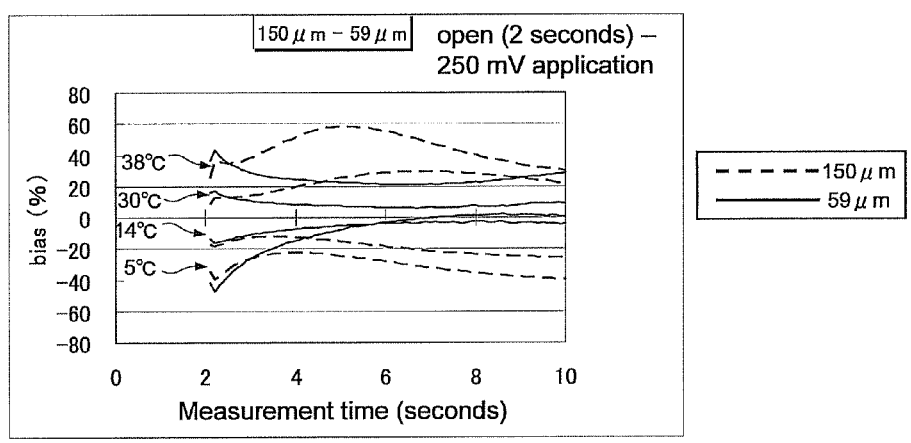
Figure 50B:
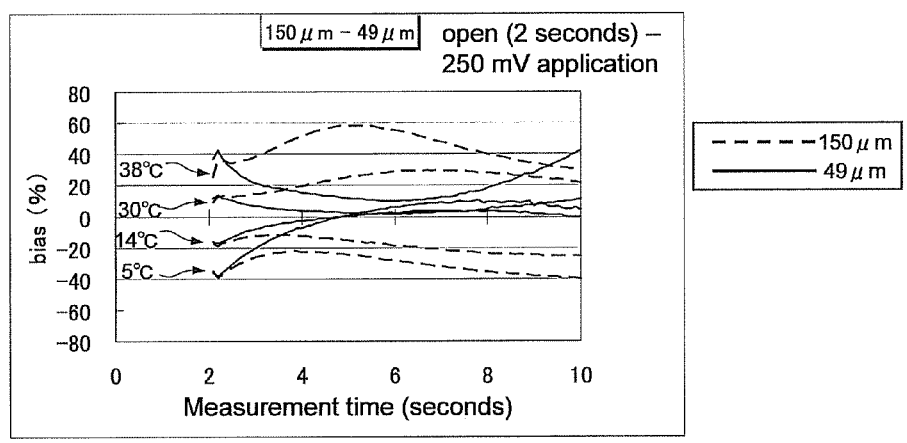
Figure 50C:
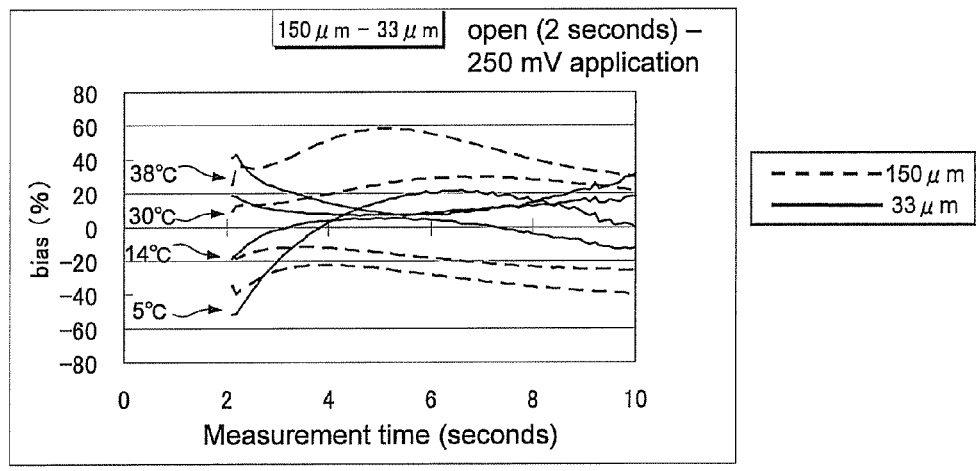
Figure 51A:
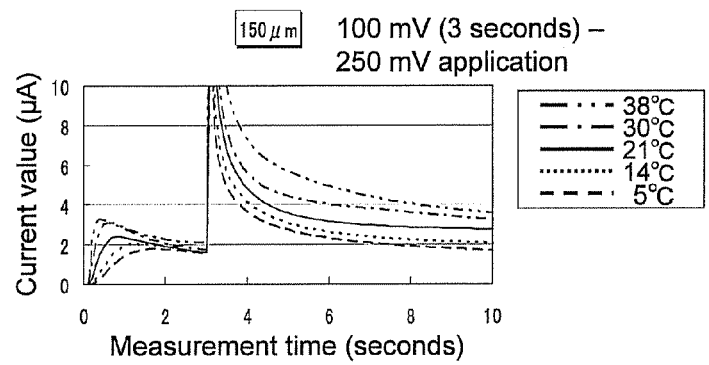
Figure 51B:
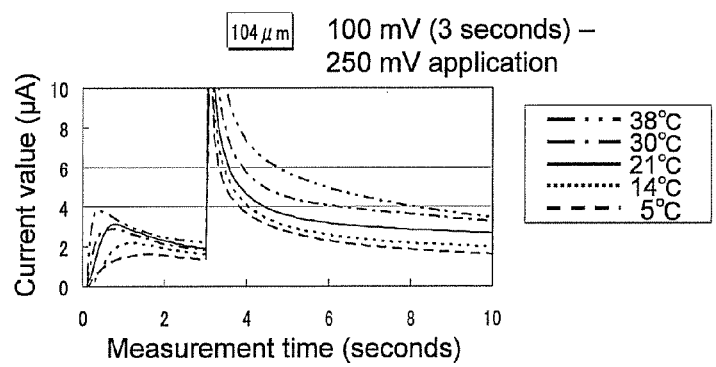
Figure 51C:
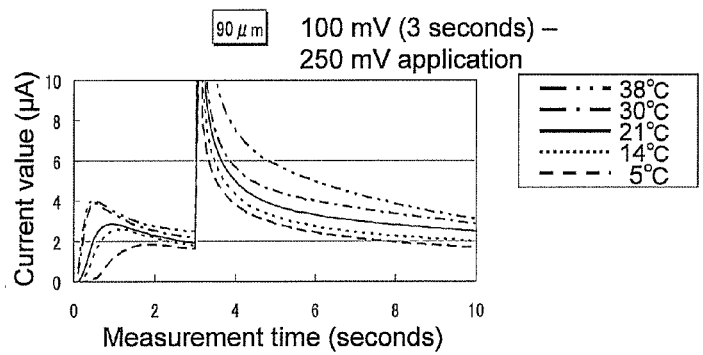
Figure 51D:
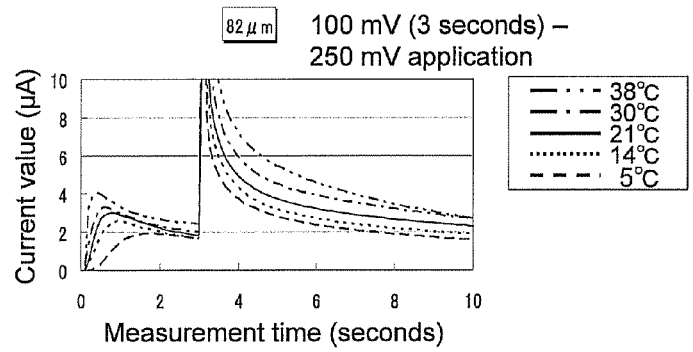
Figure 52A:
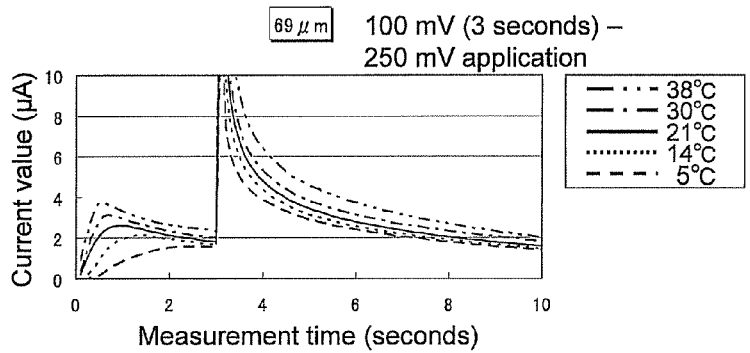
Figure 52B:
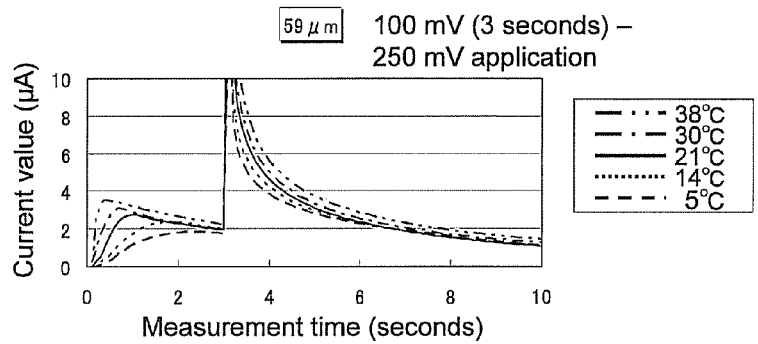
Figure 52C:
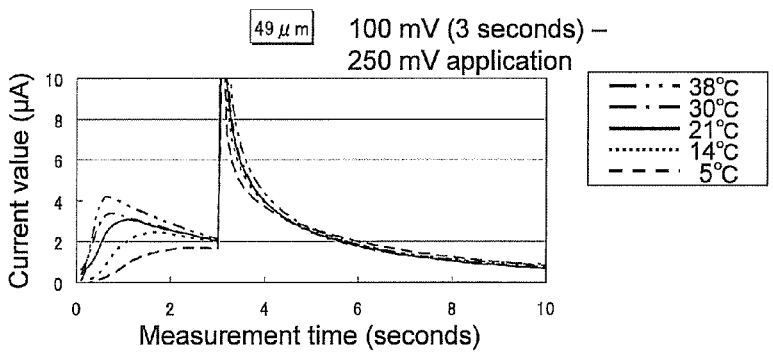
Figure 52D:
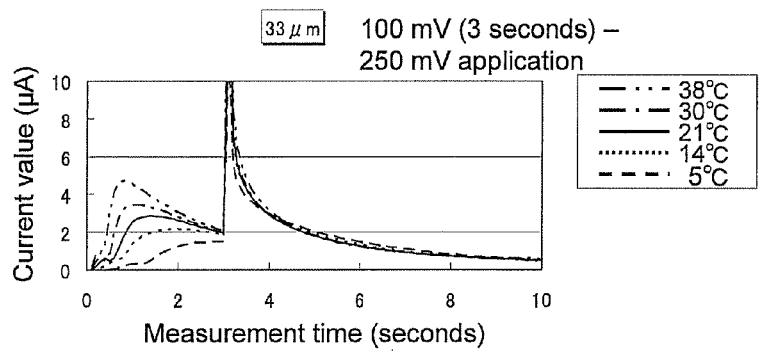
Figure 53A:
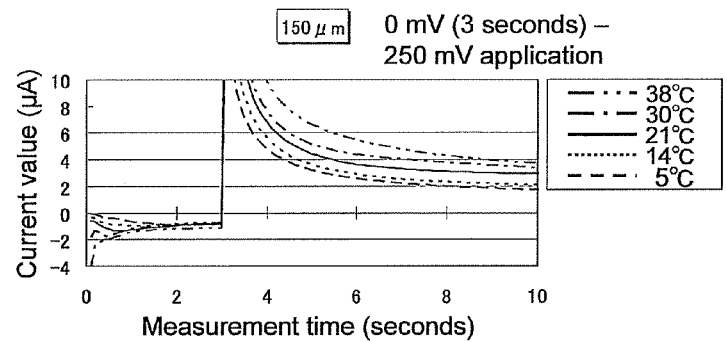
Figure 53B:
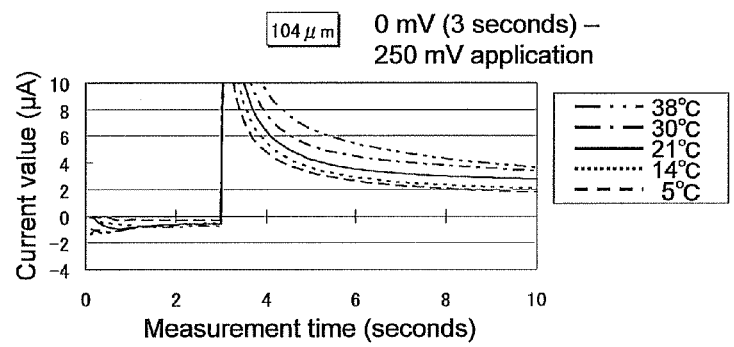
Figure 53C:
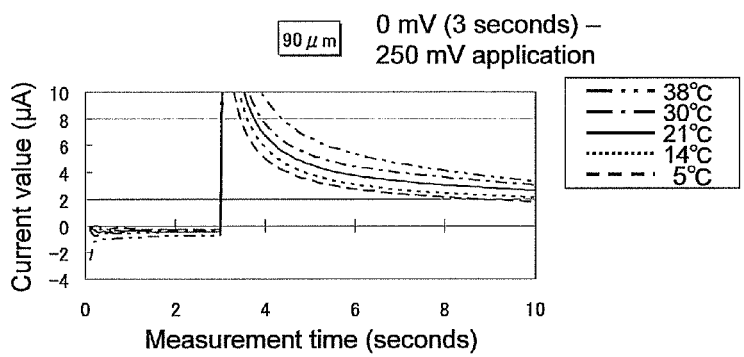
Figure 53D:
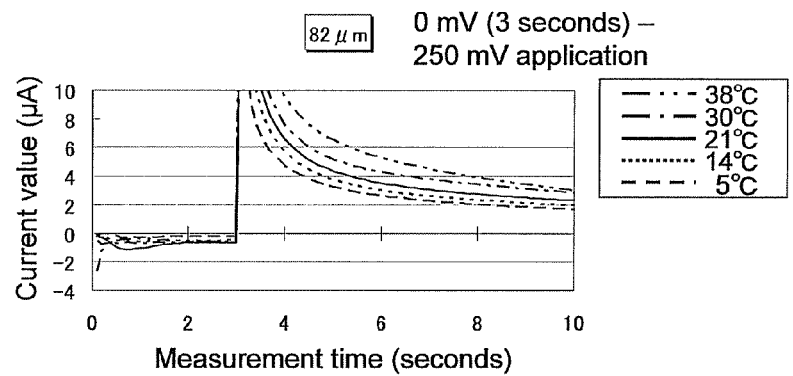
Figure 54A:
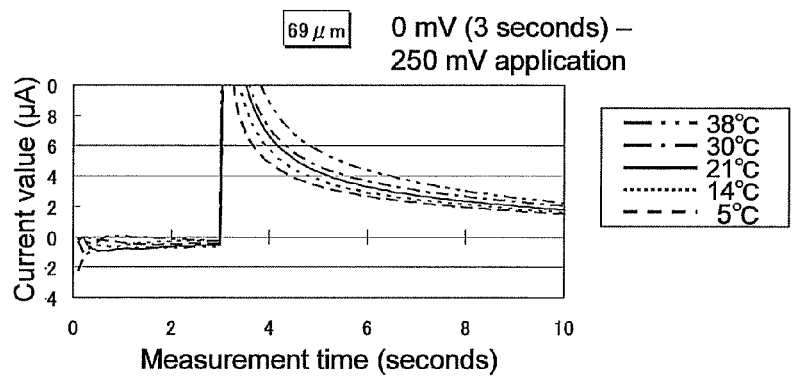
Figure 54B:
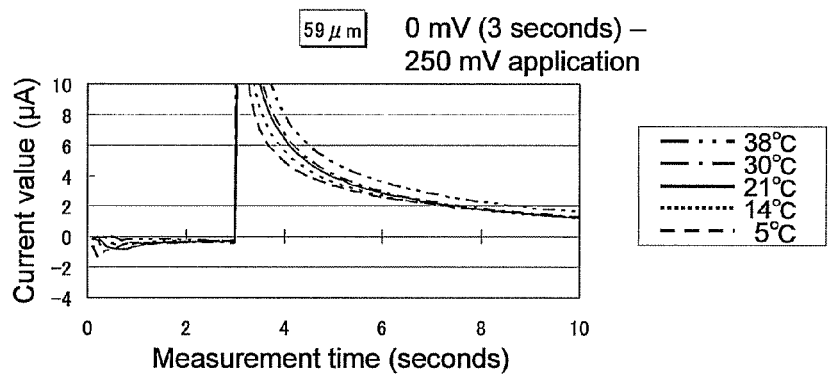
Figure 54C:
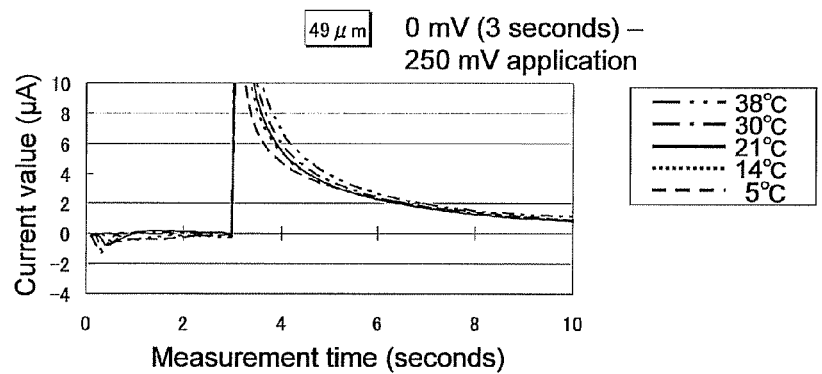
Figure 54D:
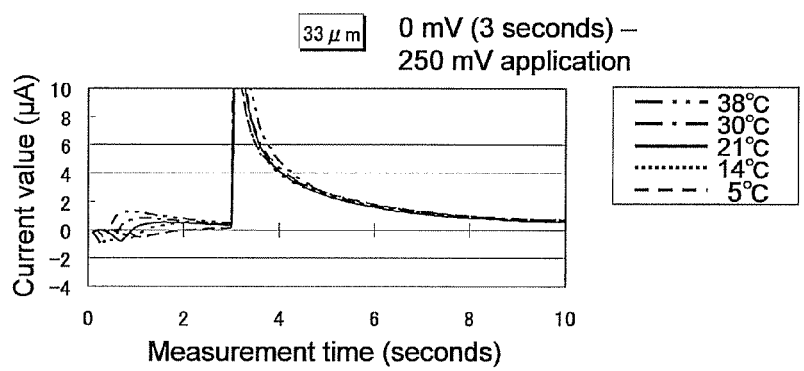
Figure 55A:
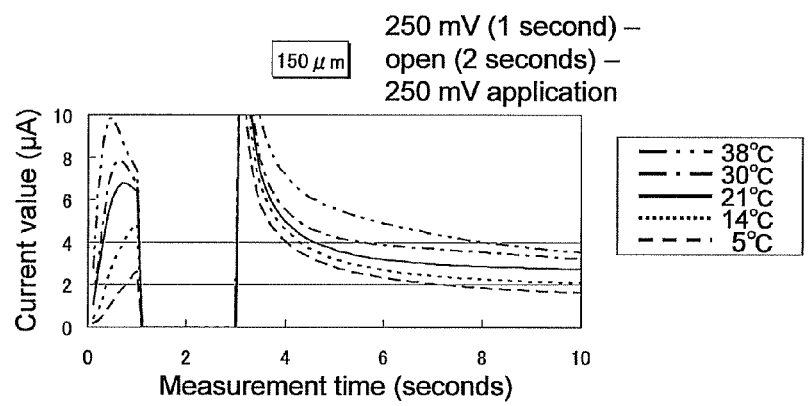
Figure 55B:
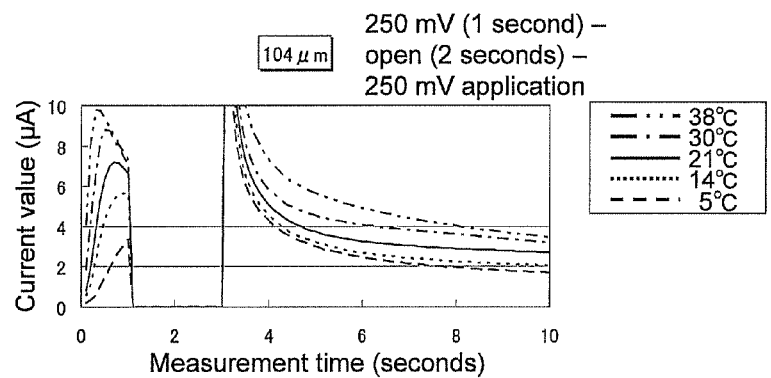
Figure 55C:
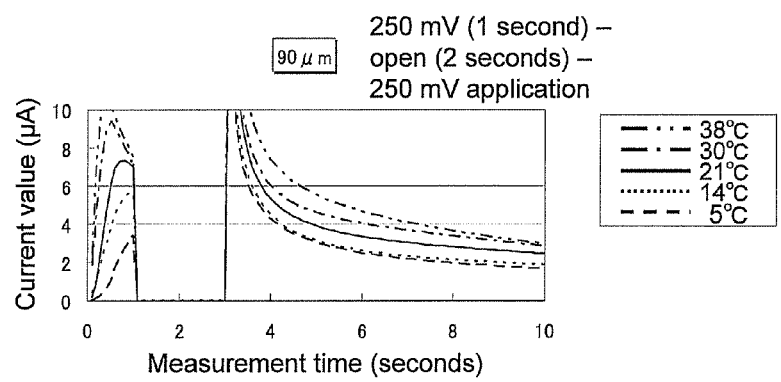
Figure 55D:
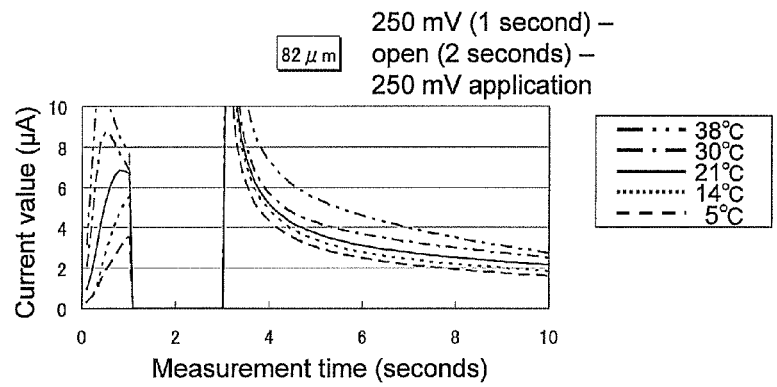
Figure 56A:
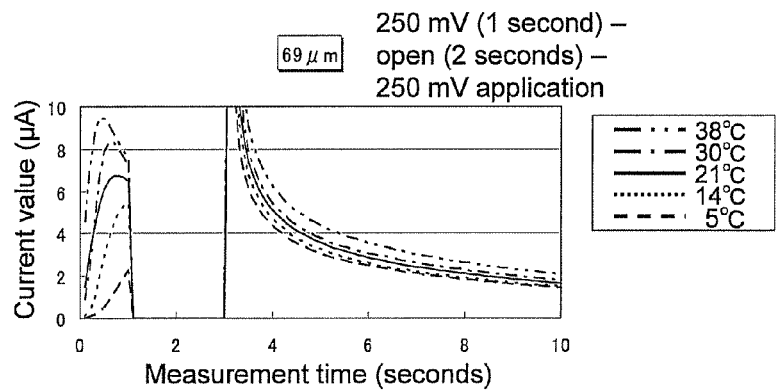
Figure 56B:
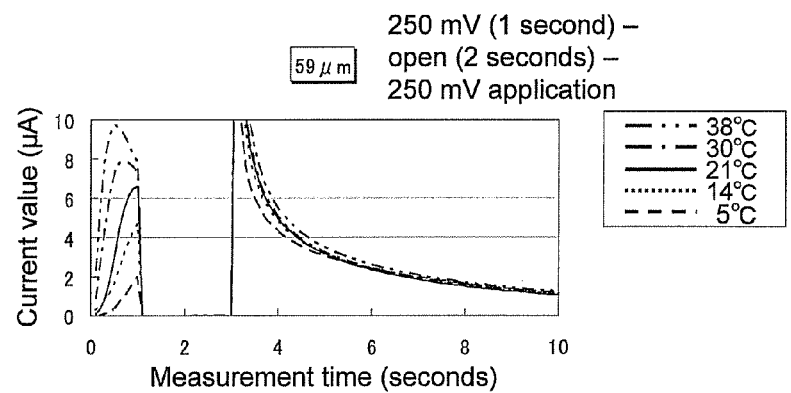
Figure 56C:
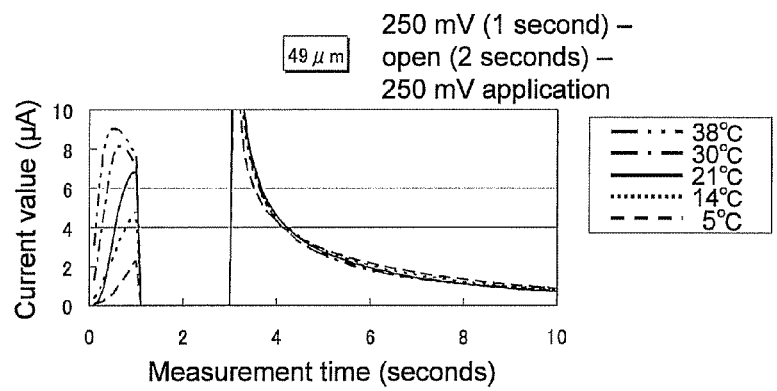
Figure 56D:
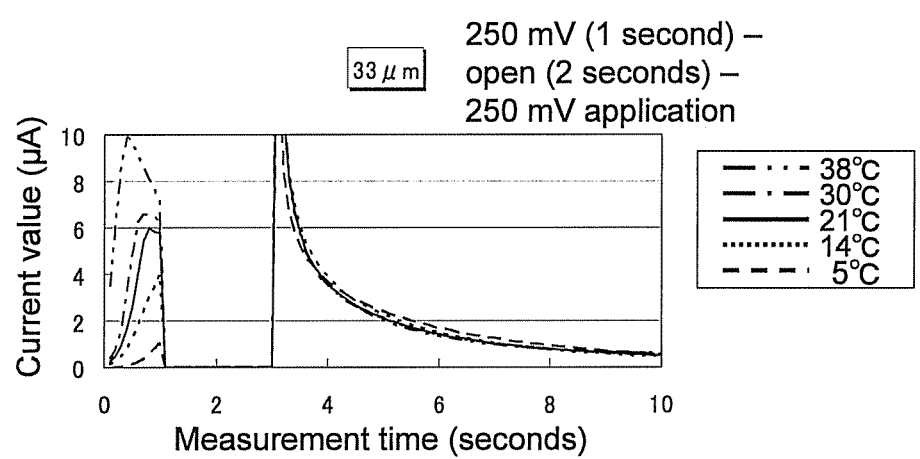

FIG. 48A is a graph of the variance in the response current value under the same conditions as in FIG. 47A, except that the height of the capillary is 59 μm (the variance obtained under the same conditions, except that the height of the capillary is 150 μm, is shown for comparison);

FIG. 48B is a graph of the variance in the response current value under the same conditions as in FIG. 47A, except that the height of the capillary is 49 μm (the variance obtained under the same conditions, except that the height of the capillary is 150 μm, is shown for comparison);

FIG. 48C is a graph of the variance in the response current value under the same conditions as in FIG. 47A, except that the height of the capillary is 33 μm (the variance obtained under the same conditions, except that the height of the capillary is 150 μm, is shown for comparison);

FIG. 49A is a graph of the variance in the response current values measured at 5° C., 14° C., 30° C., and 38° C. when the glucose concentration of the sample is 100 mg/dL, the voltage application conditions are open (2 seconds)—250 mV, and the height of the capillary is 104 μm, using the response current value at 21° C. as a reference (the variance obtained under the same conditions, except that the height of the capillary is 150 μm, is shown for comparison);

FIG. 49B is a graph of the variance in the response current value under the same conditions as in FIG. 49A, except that the height of the capillary is 90 μm (the variance obtained under the same conditions, except that the height of the capillary is 150 μm, is shown for comparison);

FIG. 49C is a graph of the variance in the response current value under the same conditions as in FIG. 49A, except that the height of the capillary is 82 μm (the variance obtained under the same conditions, except that the height of the capillary is 150 μm, is shown for comparison);

FIG. 49D is a graph of the variance in the response current value under the same conditions as in FIG. 49A, except that the height of the capillary is 69 μm (the variance obtained under the same conditions, except that the height of the capillary is 150 μm, is shown for comparison);

FIG. 50A is a graph of the variance in the response current value under the same conditions as in FIG. 49A, except that the height of the capillary is 59 μm (the variance obtained under the same conditions, except that the height of the capillary is 150 μm, is shown for comparison);

FIG. 50B is a graph of the variance in the response current value under the same conditions as in FIG. 49A, except that the height of the capillary is 49 μm (the variance obtained under the same conditions, except that the height of the capillary is 150 μm, is shown for comparison);

FIG. 50C is a graph of the variance in the response current value under the same conditions as in FIG. 49A, except that the height of the capillary is 33 μm (the variance obtained under the same conditions, except that the height of the capillary is 150 μm, is shown for comparison);

FIG. 51A is a graph of the variance in the response current values when the glucose concentration of the sample is 100 mg/dL, the voltage application conditions are open (3 seconds)—250 mV, and the height of the capillary is 150 μm;

FIG. 51B is a graph of the response current value under the same conditions as in FIG. 51A, except that the height of the capillary is 104 μm;

FIG. 51C is a graph of the response current value under the same conditions as in FIG. 51A, except that the height of the capillary is 90 μm;

FIG. 51D is a graph of the response current value under the same conditions as in FIG. 51A, except that the height of the capillary is 82 μm;

FIG. 52A is a graph of the response current value under the same conditions as in FIG. 51A, except that the height of the capillary is 69 μm;

FIG. 52B is a graph of the response current value under the same conditions as in FIG. 51A, except that the height of the capillary is 59 μm;

FIG. 52C is a graph of the response current value under the same conditions as in FIG. 51A, except that the height of the capillary is 49 µm;

FIG. 52D is a graph of the response current value under the same conditions as in FIG. 51A, except that the height of the capillary is 33 µm;

FIG. 53A is a graph of the response current value when the glucose concentration of the sample is 100 mg/dL, the voltage application conditions are 0 mV (3 seconds)—250 mV, and the height of the capillary is 150 µm;

FIG. 53B is a graph of the response current value under the same conditions as in FIG. 53A, except that the height of the capillary is 104 µm;

FIG. 53C is a graph of the response current value under the same conditions as in FIG. 53A, except that the height of the capillary is 90 µm;

FIG. 53D is a graph of the response current value under the same conditions as in FIG. 53A, except that the height of the capillary is 82 µm;

FIG. 54A is a graph of the response current value under the same conditions as in FIG. 53A, except that the height of the capillary is 69 µm;

FIG. 54B is a graph of the response current value under the same conditions as in FIG. 53A, except that the height of the capillary is 59 µm;

FIG. 54C is a graph of the response current value under the same conditions as in FIG. 53A, except that the height of the capillary is 49 µm;

FIG. 54D is a graph of the response current value under the same conditions as in FIG. 53A, except that the height of the capillary is 33 µm;

FIG. 55A is a graph of the response current value when the glucose concentration of the sample is 100 mg/dL, the voltage application conditions are 250 mV (1 second)—open (2 seconds)—250 mV, and the height of the capillary is 150 µm;

FIG. 55B is a graph of the response current value under the same conditions as in FIG. 55A, except that the height of the capillary is 104 µm;

FIG. 55C is a graph of the response current value under the same conditions as in FIG. 55A, except that the height of the capillary is 90 µm;

FIG. 55D is a graph of the response current value under the same conditions as in FIG. 55A, except that the height of the capillary is 82 µm;

FIG. 56A is a graph of the response current value under the same conditions as in FIG. 55A, except that the height of the capillary is 69 µm;

FIG. 56B is a graph of the response current value under the same conditions as in FIG. 55A, except that the height of the capillary is 59 µm;

FIG. 56C is a graph of the response current value under the same conditions as in FIG. 55A, except that the height of the capillary is 49 µm; and FIG. 56D is a graph of the response current value under the same conditions as in FIG. 55A, except that the height of the capillary is 33 µm.

DESCRIPTION OF EMBODIMENTS

A biosensor system 100 featuring a sensor chip 200 pertaining to an embodiment of the present invention will now be described.

1. Configuration of Biosensor System

Figure 1:
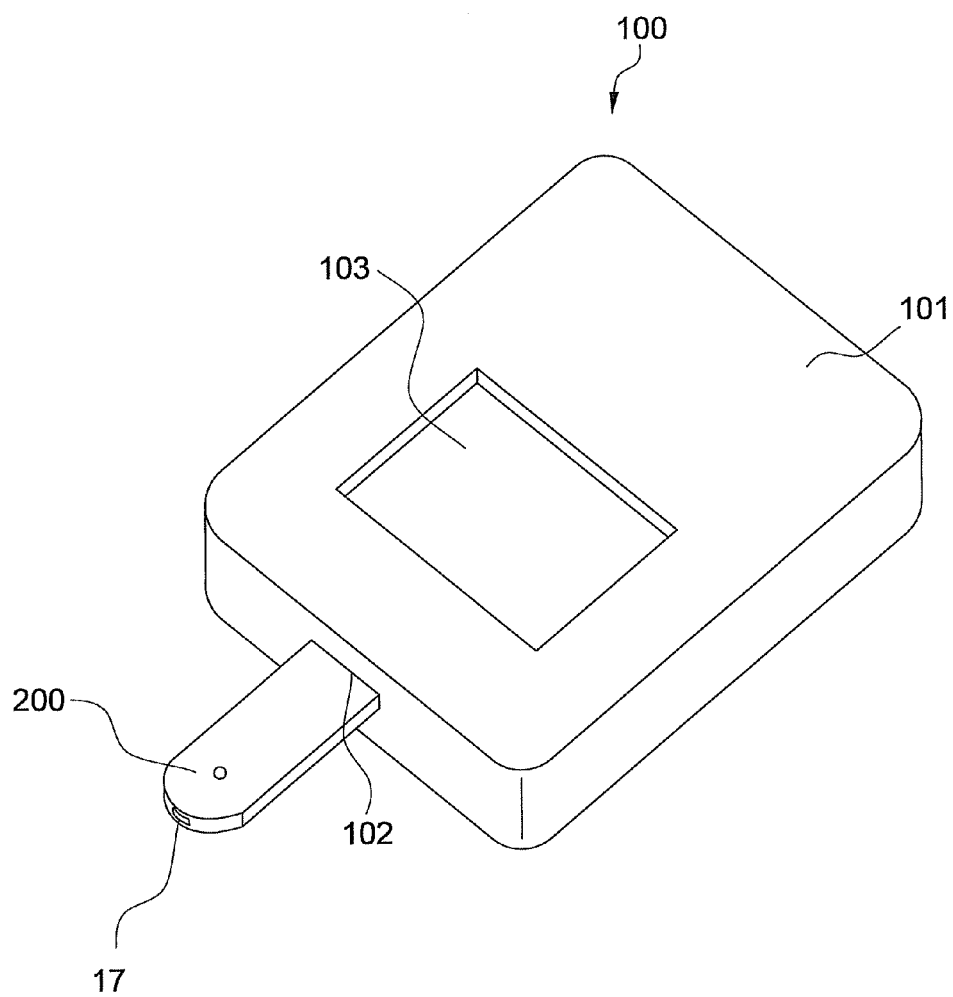
FIG. 1 is an perspective view of the configuration of a biosensor system pertaining to an embodiment of the present invention.

The biosensor system 100 pertaining to this embodiment is a system that includes a sensor for measuring the concentration of an analyte included in a liquid sample. As shown in FIG. 1, the biosensor system 100 has a measurement device 101 and the sensor chip 200.

The liquid sample is not limited to being any particular sample, and a variety of samples can be used, such as blood, perspiration, urine, and other such biologically derived liquid samples (biological samples); liquid samples that come from a river, the ocean, a lake, or another such environment; and liquid samples that come from food. The biosensor system 100 is preferably applied to a biological sample, and particularly to blood.

Nor is the analyte (the substance to be measured) limited to any particular substance, and the sensor chip 200 can accommodate any of a variety of substances, by changing the enzyme or the like in a reagent layer 20 (discussed below). Examples of analytes in a blood sample include substances excluding blood cells, such as glucose, albumin, lactic acid, bilirubin, and cholesterol.

The measurement device 101 has in its side wall a mounting opening 102, which is a rectangular hole. The sensor chip 200 can be connected in a removable state to the mounting opening 102. A display section 103 that displays measurement results is disposed in the approximate center of one main face of the measurement device 101. The configuration of the measurement device 101 will be discussed in detail below.

2. Sensor Chip

2-1. Configuration of Sensor Chip

Figure 2:
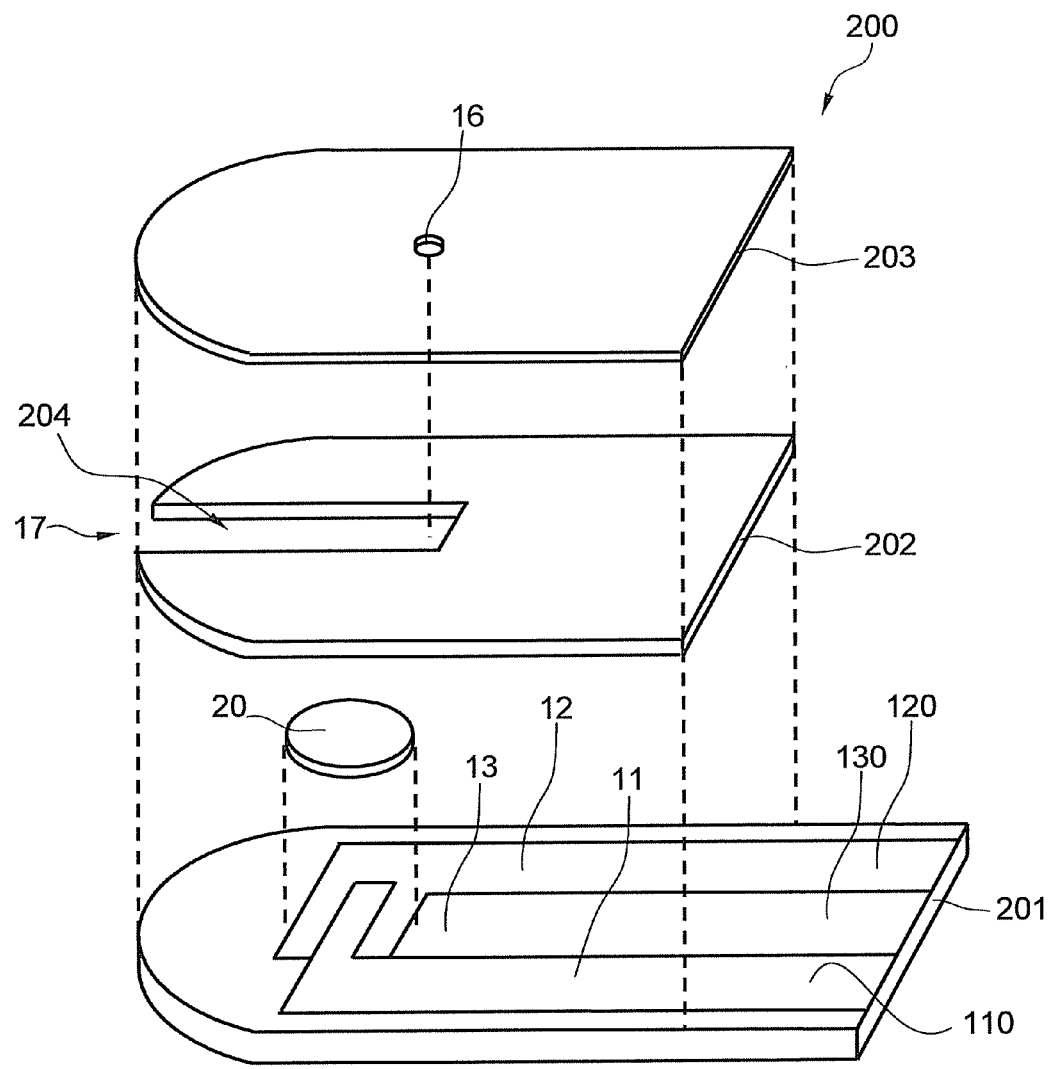
FIG. 2 is an exploded perspective view of a sensor chip included in the biosensor system in FIG. 1.
Figure 3:
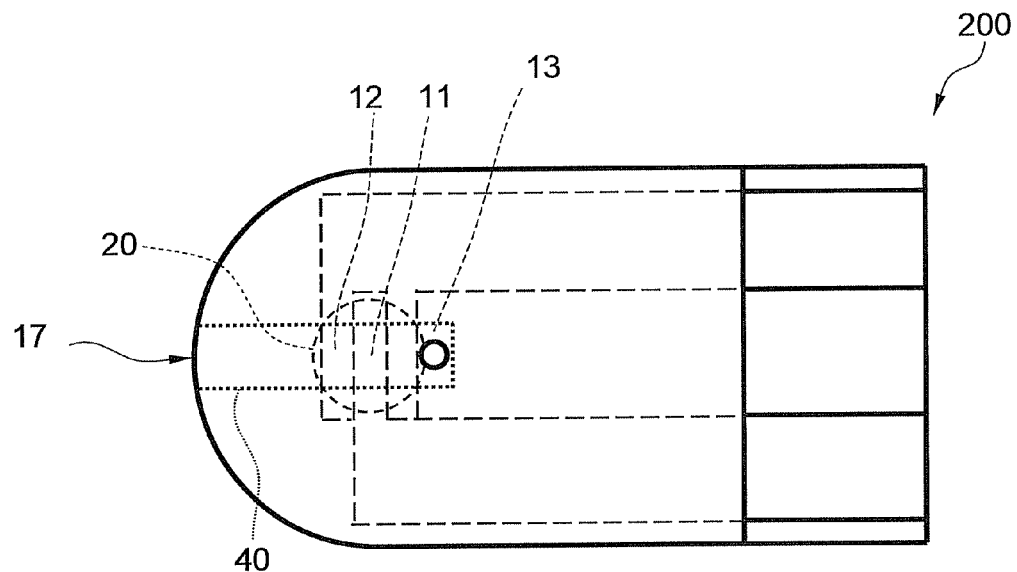
FIG. 3 is a plan view of the sensor chip in FIG. 2.

The sensor chip 200 is a disposable sensor chip that is discarded after a single use. As shown in FIGS. 2 and 3, the sensor chip 200 comprises an insulated board 201, a spacer 202, and a cover 203. The cover 203 is disposed on the insulated board 201 with the spacer 202 in between. The insulated board 201, the spacer 202, and the cover 203 are integrated adhesively, by heat fusion, or the like, for example.

The materials of the insulated board 201, the spacer 202, and the cover 203 can be polyethylene terephthalate, polycarbonate, polyimide, polyethylene, polypropylene, polystyrene, polyvinyl chloride, polyoxymethylene, monomer cast nylon, polybutylene terephthalate, methacrylic resin, ABS resin, and other such resins, and glass.

The sensor chip 200 further comprises a capillary 40 (FIG. 3). The capillary 40 holds a liquid sample. The capillary 40 is constituted by a cut-out 204 in the spacer 202. The capillary 40 has a shape that is longer in the long-side direction of the sensor chip 200. The capillary 40 leads to the outside of the sensor chip 200 at one end of the spacer 202 (the end on the left in FIGS. 2 and 3). In other words, the sensor chip 200 comprises an introduction port 17 that opens outward, and the capillary 40 is connected to and communicates with the introduction port 17. The volume of the liquid sample introduced into the capillary 40 is 1 µL or less, for example.

Three electrodes 11 to 13 are provided on the surface of the insulated board 201. The electrode 11 is sometimes called a working electrode, the electrode 12 a counter electrode, and the electrode 13 a detecting electrode. A portion of each of the electrodes 11 to 13 is disposed within the capillary 40. The electrodes 11 to 13 are disposed so as to be aligned in the order of the electrode 12, the electrode 11, the electrode 12, and the electrode 13, from the introduction port 17 toward the interior of the capillary 40. That is, in FIG. 5A, the electrodes are disposed so as to be opposite each other in the planar direction of the insulated board 201.

Figure 5A:
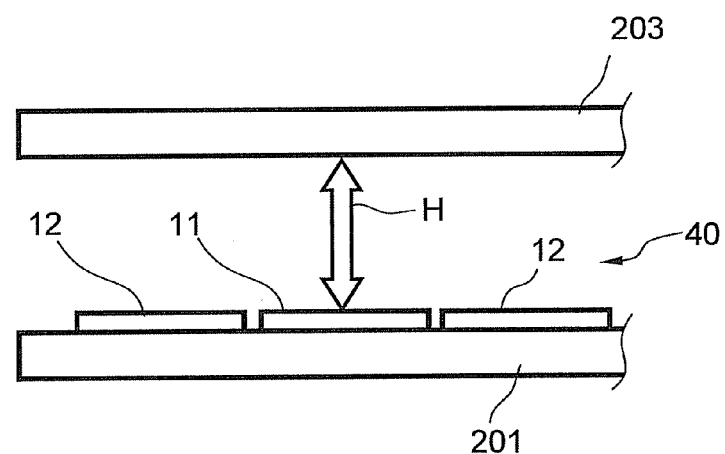
FIG. 5A is a diagram illustrating the height of a capillary in the sensor chip pertaining to an embodiment.
Figure 5B:
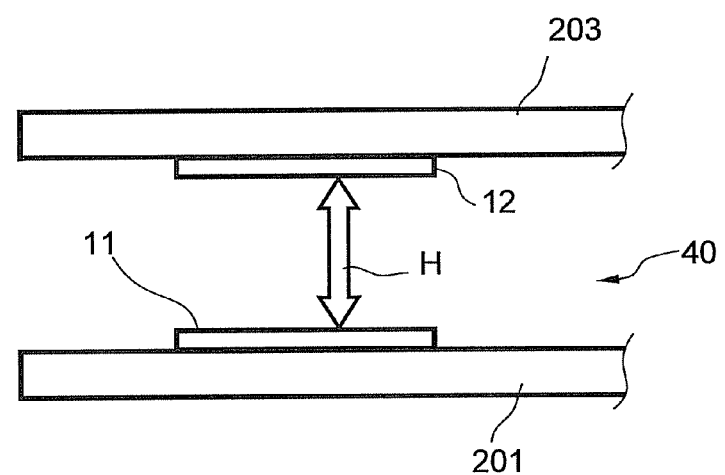
FIG. 5B is a diagram illustrating the height of a capillary in the sensor chip pertaining to another embodiment.

However, as shown in FIG. 5B, the electrode 11, the electrode 12, and the electrode 13 may be disposed three-dimensionally. For instance, the electrode 12 may be provided at a location opposite the capillary 40 on the lower face of the cover 203, and the electrode 11 and the electrode 13 may be provided on the insulated board 201.

There are no particular restrictions on the number of electrodes 11 to 13 used in the sensor chip 200. The number of each of the electrodes may be two or more.

The material of the electrodes 11 to 13 may be palladium, platinum, gold, silver, titanium, copper, nickel, carbon, or any other known conductive material.

Also, the electrodes 11 to 13 are lined to leads 110, 120, and 130, respectively. The leads 110, 120, and 130 are provided on the insulated board 201. One end of the insulated board 201 is not covered by the spacer 202 and the cover 203. One end of the leads 110, 120, and 130 is not covered on the insulated board 201, and is exposed outside the sensor chip 200. The measurement device 101 applies voltage to the electrodes 11 to 13 via the leads 110, 120, and 130.

An air vent 16 is provided to the cover 203 at a location facing the inner part of the cut-out 204 (the opposite side from the introduction port 17) that forms the capillary 40. Because the air vent 16 is provided, the liquid sample introduced into the capillary 40 flows under capillary action and in rate-limiting fashion to a detector constituted by the electrodes 11 to 13 and the reagent layer 20. Thus, the air vent 16 ensures the deposition of a blood sample (biological sample), and improves measurement stability.

Also, the faces on the inside the capillary 40 may be given a hydrophilic treatment or formed from a hydrophilic material. This facilitates the deposition (intake) of the liquid sample and improves reliability.

The reagent layer 20 is placed on the electrodes 11 to 13 between the insulated board 201 and the spacer 202.

The reagent layer 20 is formed by precoating the insulated board 201 with a reagent that includes an electrolyte. The reagent layer 20 is formed so as to cover the overlapping portion of the electrodes 11, 12, and 13 on the insulated board 201. The reagent layer 20 contains an electron-transfer mediator (hereinafter referred to simply as a "mediator") and a redox enzyme in which the analyte in the liquid sample serves as the substrate.

A redox enzyme in which the analyte serves as the substrate can be used favorably as the enzyme. Examples of this enzyme include glucose oxidase and glucose dehydrogenase when the analyte is glucose; lactic acid oxidase and lactic acid dehydrogenase when the analyte is lactic acid; cholesterol esterase and cholesterol oxidase when the analyte is cholesterol; and bilirubin oxidase when the analyte is bilirubin. Other examples of analyte include triglyceride and uric acid.

The mediator is a substance having the function of transferring electrons produced by an enzyme reaction to the electrodes. One or more types of mediator selected from the group consisting of potassium ferricyanide, p-benzoquinone, p-benzoquinone derivatives, oxide-type phenazine methosulfate, methylene blue, ferricinium, and ferricinium derivatives can be used favorably, for example.

The amount of redox enzyme in the reagent layer will vary with the type of enzyme and so forth, in general, 0.01 to 100 units (U) is favorable, with 0.05 to 10 U being preferable, and 0.1 to 5 U being even better.

The reagent layer 20 may contain a water-soluble polymer compound in order to improve the moldability of the reagent layer. This water-soluble polymer compound may be one or more types selected from among carboxymethyl cellulose and salts thereof; hydroxyethyl cellulose, hydroxypropyl cellulose, methyl cellulose, ethyl cellulose, ethyl hydroxyethyl cellulose, carboxyethyl cellulose, and salts thereof; polyvinyl alcohol, polyvinylpyrrolidone, polylysine, and other such polyamino acids; polystyrenesulfonic acid and salts thereof; gelatin and derivatives thereof; polyacrylic acid and salts thereof; polymethacrylic acid and salts thereof; starch and derivatives thereof; maleic anhydride polymers and salts thereof; and agarose gel and derivatives thereof.

2-2. Height of Capillary 40

The system inside the capillary 40 into which the liquid sample is introduced is a diffusion system including a liquid and a diffusant (analyte and mediator, etc.) The liquid here could also be called a diffusion medium or a dispersion medium.

The diffusion distance d of the various diffusants in the liquid is expressed by the following formula (1).

[First Mathematical Formula]

$$d = \sqrt{zDt} \quad (1)$$

z: a constant
D: diffusion coefficient
t: time

The constant z is an arbitrarily selected value. The constant z can vary with the experiment conditions, and can vary according to the definition of the distribution of the distance over which a diffusant is diffused. The constant z is generally set to a range of $1 \leq z \leq 4$. More specifically, the constant z may be defined as 1, 2, $\pi$, or 4. In the field of electrochemistry, $z = \pi$ is sometimes used as an example, so we will use $z = \pi$ in the following description.

The diffusion coefficient D is expressed by a Stokes-Einstein relation (the following formula (2)).

[Second Mathematical Formula]

$$D = \frac{kT}{6\pi\mu r} \quad (2)$$

k: Boltzmann constant
T: absolute temperature
μ: viscosity
r: radius of diffused molecules Thus, based on Formulas 1 and 2, the diffusion distance d is expressed by the following formula (3).

[Third Mathematical Formula]

$$d = \sqrt{\frac{tkT}{6\mu r}} \quad (3)$$

That is, in general, when the temperature rises, the diffusion distance increases.

Furthermore, in a system in which the viscosity μ is dependent on temperature, the viscosity μ is expressed by an Andrade formula (4).

[Fourth Mathematical Formula]

$$\mu = A\exp\left(\frac{E}{RT}\right) \quad (4)$$

A: proportional constant
E: fluid activation energy
R: gas constant
T: absolute temperature If we plug the above-mentioned Formula 3 into the above-mentioned Formula 4, we obtain the following formula (5).

[Fifth Mathematical Formula]

$$d = \sqrt{\frac{tkT}{6\mu r}} \quad (5)$$

$$= \sqrt{\frac{tkT}{6rA\exp\left(\frac{E}{RT}\right)}}$$

Here, if we assume that:

[Sixth Mathematical Formula]

$$\sqrt{\frac{k}{6rA}} = B \quad (6)$$

B: constant term then the diffusion distance d is expressed by the following formula (7).

[Seventh Mathematical Formula]

$$d = B\sqrt{\frac{tT}{\exp\left(\frac{E}{RT}\right)}} \quad (7)$$

In the above-mentioned Formula 7, when the temperature T rises, the exp(E/RT) of the denominator decreases, so there is a further increase in the diffusion distance d.

In general, the fluid activation energy E is large in a high-viscosity liquid, so the viscosity μ is susceptible to the effect of the temperature T. As a result, the higher is the viscosity of the liquid sample, the more susceptible are the diffusion coefficient D and the diffusion distance d to the effect of the temperature T. For example, when the temperature T rises, the viscosity μ decreases and the diffusion coefficient D and the diffusion distance d increase.

Figure 4:
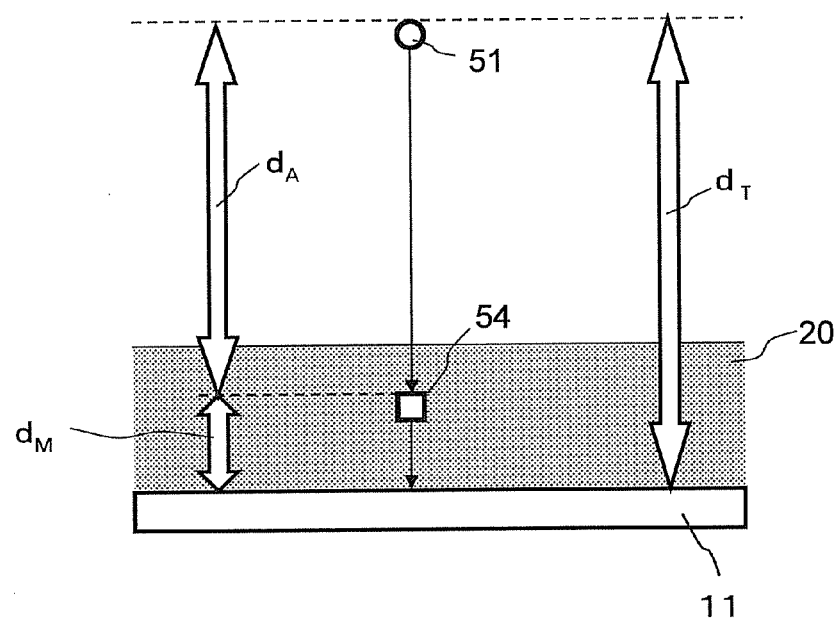
FIG. 4 is a schematic diagram of the diffusion distance of an analyte and a mediator.

As shown in FIG. 4, an analyte 51 diffuses into the interior of the reagent layer 20, and transfers electrons through an enzyme reaction to a mediator 54. The mediator 54 diffuses to the working electrode 11.

If we let $D_A$ be the diffusion constant of the analyte 51, and let $t_A$ be the diffusion time it takes for the analyte to transfer electrons to the mediator, then the diffusion distance $d_A$ of the analyte 51 is expressed by the following formula (8). The diffusion time $t_A$ is an arbitrarily set numerical value.

[Eighth Mathematical Formula]

$$d_A = \sqrt{\pi D_A t_A} \quad (8)$$

Similarly, if we let $D_M$ be the diffusion constant of the mediator 54, and let $t_M$ be the diffusion time it takes for the mediator 54 to transfer electrons to the working electrode 11, then the diffusion distance $d_M$ of the mediator 54 is expressed by the following formula (9). The diffusion time $t_M$ is also an arbitrarily set numerical value.

[Ninth Mathematical Formula]

$$d_M = \sqrt{\pi D_M t_M} \quad (9)$$

Based on the above-mentioned Formulas 8 and 9, the total diffusion distance $d_T$ until the analyte 51 is detected as a current response is expressed by the following formula (10).

[Tenth Mathematical Formula]

$$d_T = \sqrt{\pi D_A t_A} + \sqrt{\pi D_M t_M} \quad (10)$$

The time until the analyte 51 is detected as a current response can also be expressed by $(t_A + t_M)$. Thus, if we let $t_{mes}$ be the measurement time, the analyte 51 will be detected within the measurement time $t_{mes}$ if the measurement time $t_{mes}$ satisfies the relation $t_{mes} \geq t_A + t_M$. That is, in this case the maximum value of $(t_A + t_M)$ is $t_{mes}$.

If the diffusion time $t_M$ of the mediator 54 is sufficiently short with respect to the diffusion time $t_A$ of the analyte 51, the system can be considered to be one in which only the analyte 51 moves one phase. Here, the maximum value $d_L$ of the total diffusion distance $d_T$ is expressed by the following formula (11).

[Eleventh Mathematical Formula]

$$d_L = \sqrt{\pi D_A t_A} \quad (11)$$

$$= \sqrt{\pi D_A t_{mes}}$$

Since an enzyme is necessary for electron acceptance between the analyte 51 and the mediator 54, the diffusion distance $d_M$ of the mediator 54 that has taken electrons is equal to the distance that the enzyme has diffused from the working electrode 11. In general, the diffusion constant of an enzyme is far smaller than the diffusion coefficient $D_A$ of the analyte 51 and the diffusion coefficient $D_M$ of the mediator 54. Accordingly, the enzyme can be considered to be in a state of having stopped near the working electrode 11. Also, since the diffusion coefficient $D_M$ of the mediator 54 is extremely short, the diffusion time $t_M$ of the mediator can generally be ignored.

On the other hand, when the diffusion time $t_M$ of the mediator is long, the diffusion system is considered to be one in which two kinds of diffusant move one phase. The maximum value $d_L$ of the total diffusion distance $d_T$ is derived when the formula $t_{mes} = t_A + t_M$ is satisfied in the above-mentioned Formula 10.

Furthermore, when the liquid sample is separated into a plurality of phases, such as when a membrane filter is provided over the reagent layer 20, the diffusion system inside the capillary 40 will be a system in which the diffusant moves a plurality of phases (n number of phases). Thus, if the diffusion time $t_M$ of the mediator 54 is sufficiently short with respect to the diffusion time $t_A$ of the analyte 51, the diffusion constant and diffusion time of the analyte 51 are defined for each phase, and the total diffusion distance $d_T$ is expressed by the following formula (12).

[Twelfth Mathematical Formula]

$$d_T = \sum_{k=1}^{n} \sqrt{\pi D_k t_k} \tag{12}$$

(where n is an integer of 2 or more)

Here, if the following formula (13) is satisfied, the maximum value $d_L$ of the total diffusion distance $d_T$ can be derived.

[Thirteenth Mathematical Formula]

$$t_{mes} = \sum_{k=1}^{n} t_k \tag{13}$$

On the other hand, if the diffusion time $t_M$ of the mediator is long, the diffusion system can be considered to be one in which two kinds of diffusant move a plurality of phases (n number of phases), the diffusion constant and diffusion time of the analyte 51 and the mediator 54 are defined for each phase, and the total diffusion distance $d_T$ is expressed by the following formula (14).

[Fourteenth Mathematical Formula]

$$d_T = \sum_{k=1}^{n} \sqrt{\pi D_k t_k} + \sum_{j=1}^{n} \sqrt{\pi D_j t_j} \tag{14}$$

(where n is an integer of 2 or more)

Here, if the following formula (15) is satisfied, the maximum value $d_L$ of the total diffusion distance $d_T$ can be derived.

[Fifteenth Mathematical Formula]

$$t_{mes} = \sum_{k=1}^{n} t_k + \sum_{j=1}^{n} t_j \tag{15}$$

The formulas given above are formulas applied to systems of infinite diffusion. A system of infinite diffusion corresponds to when the height H of the capillary 40 is set high. On the other hand, when the height H is set low, the diffusion system inside the capillary 40 becomes a system of finite diffusion. In this case, the range over which the analyte 51 can diffuse is limited by the height H.

Whether or not the height H is greater than the maximum value $d_L$ of the total diffusion distance $d_T$ becomes a boundary for the diffusion system inside the capillary 40 will be of finite diffusion or infinite diffusion. Specifically, when the diffusion time $t_M$ of the mediator 54 is sufficiently short with respect to the diffusion time $t_A$ of the analyte 51, the inside of the capillary 40 becomes a system of finite diffusion when the height H satisfies the following formula (16).

[Sixteenth Mathematical Formula]

$$\sqrt{\pi D_A t_A} = \sqrt{\pi D_A t_{mes}} > H \tag{16}$$

On the other hand, when the diffusion time $t_M$ of the mediator 54 is long, and the diffusion system inside the capillary 40 is one in which two kinds of diffusant move one phase, then the diffusion system inside the capillary 40 will be a system of finite diffusion when the height H satisfies the following formula (17) under a condition of $t_{mes}=t_A+t_M$.

[Seventeenth Mathematical Formula]

$$\sqrt{\pi D_A t_A} + \sqrt{\pi D_M t_M} > H \tag{17}$$

Also, when the system inside the capillary 40 is one in which the diffusion time $t_M$ of the mediator 54 is sufficiently short with respect to the diffusion time $t_A$ of the analyte 51, and the analyte 51 moves a plurality of phases (n number of phases), then the diffusion system inside the capillary 40 will be a system of finite diffusion when the height H satisfies the following formula (18) under the condition of the above-mentioned Formula 13.

[Eighteenth Mathematical Formula]

$$\sum_{k=1}^{n} \sqrt{\pi D_k t_k} > H \tag{18}$$

Furthermore, when the system inside the capillary 40 is one in which the diffusion time $t_M$ of the mediator 54 is long, and two kinds of diffusant move a plurality of phases (n number of phases), then the diffusion system inside the capillary 40 will be a system of finite diffusion when the height H satisfies the following formula (19) under the condition of the above-mentioned Formula 15.

[Nineteenth Mathematical Formula]

$$\sum_{k=1}^{n} \sqrt{\pi D_k t_k} + \sum_{j=1}^{n} \sqrt{\pi D_j t_j} > H \tag{19}$$

The diffusion coefficient D is found using experiment variables and current values and using polarography, a rotating disk electrode method, a potential sweep method, a potential step method, or another such method in the field of electrochemistry. The diffusion coefficient D is also found by a measurement method based on something other than electrochemistry, such as a Taylor dispersion method, a nuclear magnetic resonance-oblique magnetic field method, or the like. In general, the diffusion coefficient of the analyte is $1 \times 10^{-5}$ cm$^2 \cdot$s$^{-1}$ or less, and the diffusion coefficient of the mediator is also $1 \times 10^{-5}$ cm$^2 \cdot$s$^{-1}$ or less.

As shown in FIG. 5A, the height H of the capillary 40 is, in more specific terms, the distance from the working electrode 11 to the inner face of the cover 203 (the opposite face from the working electrode 11). That is, the height H may be the thickness of the spacer 202, or may be a value obtained by adding the thickness of the reagent layer 20 to the thickness of the spacer 202.

The height H is set so that the diffusion system inside the capillary 40 will be a system of finite diffusion. The range of the height H here is as described through reference to Formulas 16 to 19 above. As discussed above, the diffusion distance d is a function of temperature. Thus, the height H is preferably set to be less than the maximum value $d_L$ of the total diffusion distance $d_T$ found at the upper limit of the measurement guaranteed temperature of the biosensor system 100. Thus setting the height H has the effect of minimizing the variance in the measurement results at high temperature with the biosensor system 100. More preferably, the height H is set to be less than the maximum value $d_L$ of the total diffusion distance $d_T$ found at the lower limit of the measurement guaranteed temperature of the biosensor system 100. Thus setting the height H has the advantage that concentration can be measured over a wide range of temperatures using a single calibration curve with the biosensor system 100.

The layout of the working electrode 11 and the counter electrode 12 is not limited to one in which they are opposite each other in the planar direction of the insulated board 201 as in FIG. 5A. For instance, the working electrode 11 and the counter electrode 12 may be disposed opposite each other in the height H direction of the capillary 40. A specific configuration is shown in FIG. 5B. In the example shown in FIG. 5B, the working electrode 11 is disposed on the insulated board 201, and the counter electrode 12 is disposed on the face of the cover 203 that is opposite the insulated board 201. With this layout, the height H is the distance between the working electrode 11 and the counter electrode 12. Again with the layout in FIG. 5B, the height H is preferably within the range discussed above.

With the configurations in both FIG. 5A and FIG. 5B, the overall height of the capillary 40 does not have to be within the above-mentioned range, as long as the distance from the working electrode 11 to the portion opposite the working electrode 11 (the cover 203 in FIG. 5A, and the counter electrode 12 in FIG. 5B) is within the above-mentioned range.

3. Measurement Device 101

Figure 6:
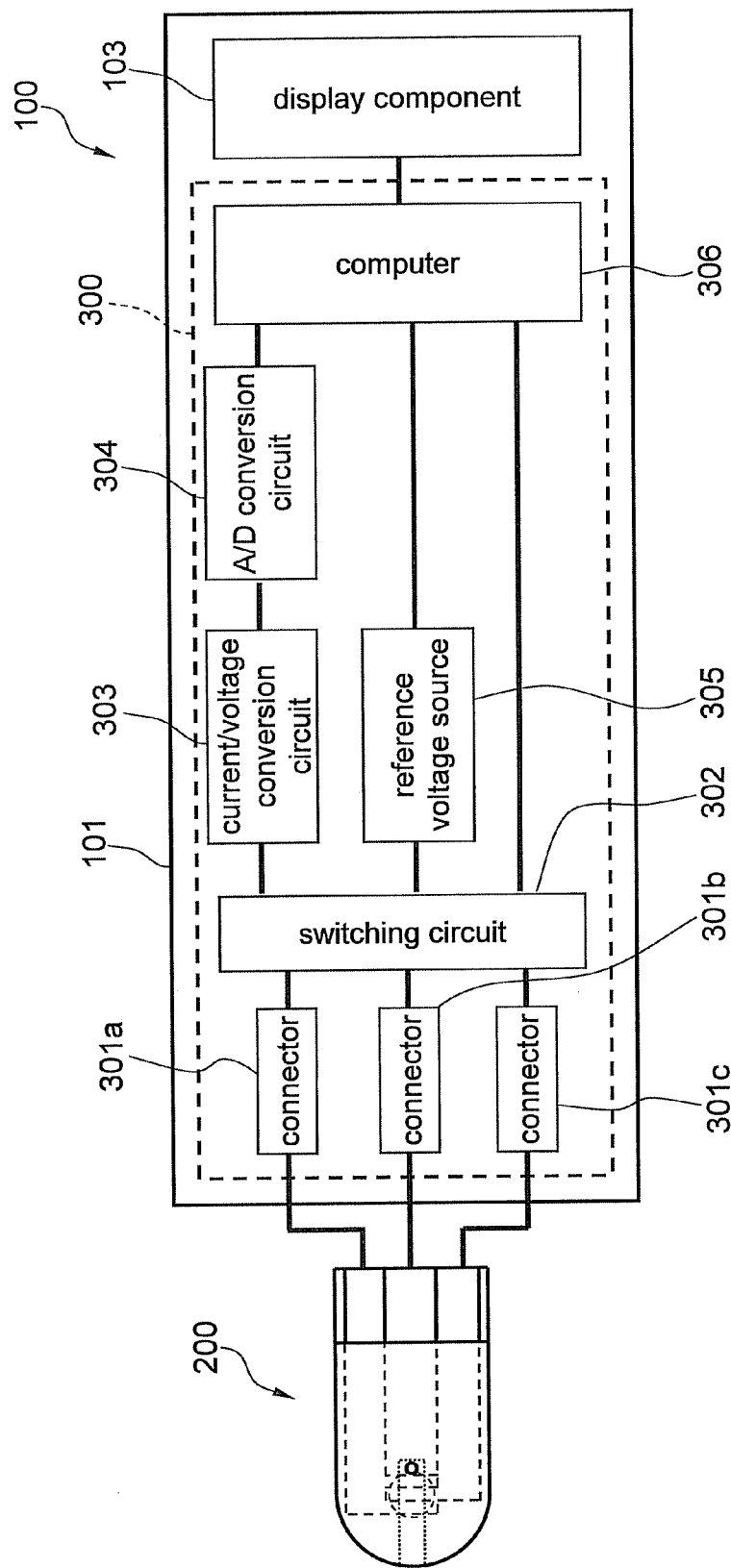
FIG. 6 is a diagram of the internal configuration of a measurement device 101 in the biosensor system in FIG. 1.

As shown in FIG. 6, the measurement device 101 has a control circuit 300 in addition to the constitution discussed above. The control circuit 300 applies voltage between at least two electrodes selected from among the electrodes 11 to 13 of the sensor chip 200 (see FIGS. 2 and 3).

More specifically, as shown in FIG. 6, the control circuit 300 has three connectors 301a, 301b, and 301c, a switching circuit 302, a current/voltage conversion circuit 303, an analog/digital conversion circuit (hereinafter referred to as an A/D conversion circuit) 304, a reference voltage source 305, and a computer 306. The control circuit 300 can switch the voltage applied to one electrode, via the switching circuit 302, so that this electrode can be used as a positive or negative pole.

As shown in FIG. 6, the connectors 301a, 301b, and 301c are connected to the counter electrode 12, the detection electrode 13, and the working electrode 11, respectively, in a state in which the sensor chip 200 is inserted into the mounting opening 102.

The switching circuit 302 can switch the electrode connected to the reference voltage source 305, and can switch the amount of voltage applied to the electrodes.

The current/voltage conversion circuit 303 receives from the computer 306 a signal directing the acquisition of a current value, and thereby converts the amount of current flowing between two electrodes connected to the current/voltage conversion circuit 303 into a voltage value. The converted voltage value is converted by the A/D conversion circuit 304 into a digital value, inputted to the computer 306, and stored in the memory of the computer 306.

The computer 306 comprises a known central processing unit (CPU) and a storage unit. Examples of the storage unit include a HDD (hard disk drive), ROM (read only memory), and RAM (random access memory). The storage unit stores a calibration curve that correlates the analyte concentration in a blood sample with the current value between the working electrode 11 and the counter electrode 12. The computer 306 can refer to the calibration curve to compute the concentration of the analyte in the blood sample.

Also, in addition to having a function of calculating the concentration of analyte as mentioned above, the computer 306 also controls the switching circuit 302, takes input from the A/D conversion circuit 304, controls the voltage of the reference voltage source 305, controls the timing of voltage application during concentration measurement, measures the application duration, etc. (timer function), outputs display data to the display section 103, and communicates with external devices, and therefore controls the entire measurement device.

The various functions of the computer 306 can be realized by the CPU by reading and executing programs held in the storage unit.

4. Measurement of Analyte Concentration

When the sensor chip 200 is used, the user deposits a liquid sample at the introduction port 17. For example, when the biosensor system 100 is used to measure a glucose value, the user pricks his finger, hand, arm, or the like, squeezes out a small amount of blood, and deposits this blood as a liquid sample for measurement.

The liquid sample deposited at the introduction port 17 moves by capillary action through the capillary 40 toward the back of the sensor chip 200, and reach the electrodes 11 to 13.

The measurement of analyte concentration performed by the biosensor system 100 will be described.

Figure 7:
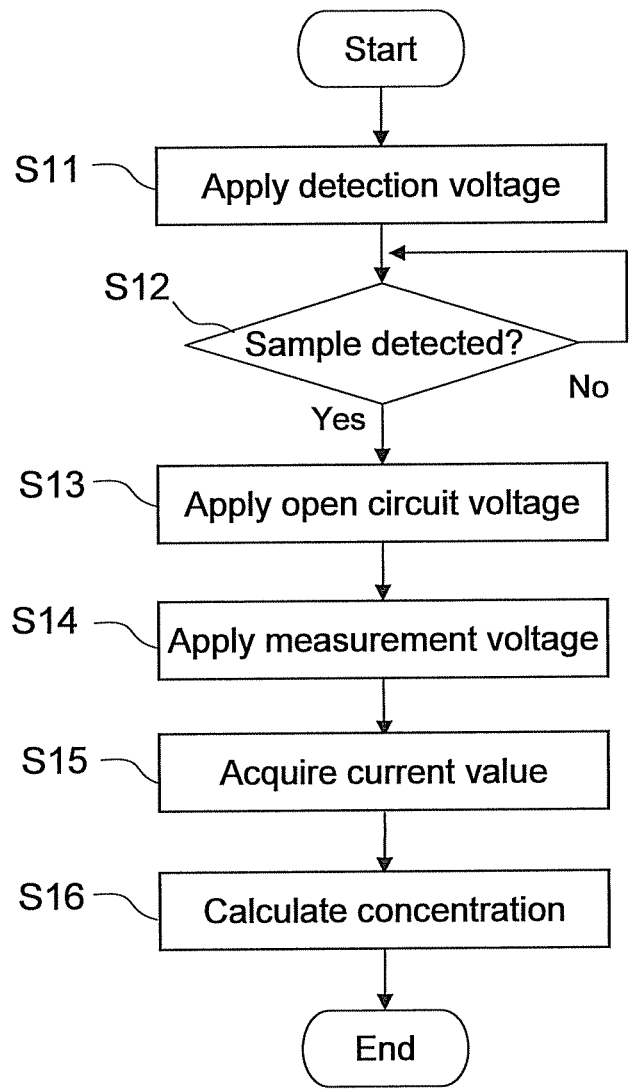
FIG. 7 is a flowchart showing an example of the flow in a method for measuring the concentration of a blood sample with the biosensor system in FIG. 1.

The operation shown in FIG. 7 begins when the sensor chip 200 is mounted in the mounting opening 102 of the measurement device 101. First, the detection electrode 13 is connected to the current/voltage conversion circuit 303 via the connector 301b by the switching circuit 302 at a command from the CPU of the computer 306, and the counter electrode 12 is connected to the reference voltage source 305 via the connector 301a. After this, a specific voltage is applied between the two electrodes at a command from the CPU (step S11). This voltage is preferably 0.01 to 2.0 V, and more preferably 0.1 to 1.0 V, and even more preferably 0.2 to 0.5 V, when the detection electrode 13 is a positive pole and the counter electrode 12 is a negative pole. This voltage is applied from the point when the sensor chip is inserted into the measurement device 101 until the blood sample is introduced deep into the capillary 40.

When the blood sample is introduced from the introduction port 17 of the sensor chip 200 into the capillary 40, current flows between the detection electrode 13 and the counter electrode 12. The CPU identifies the amount of increase in current per unit of time before and after the blood sample is introduced, and thereby detects that the capillary 40 has been filled with the blood sample. The value of this current is converted into a voltage value by the current/voltage conversion circuit 303, after which it is converted into a digital value by the A/D conversion circuit 304, and inputted to the CPU. The CPU detects that the blood sample has been introduced deep into the capillary on the basis of this digital value.

When a sample is thus detected (Yes in step S12), step S13 is executed. Specifically, at a command from the CPU of the computer 306, the switching circuit 302 disconnects the detection electrode 13 from the current/voltage conversion circuit 303, connects the working electrode 11 and the reference voltage source 305, and connects the counter electrode 12 and the current/voltage conversion circuit 303.

More specifically, the working electrode 11 is connected to the current/voltage conversion circuit 303 via the connector 301c, and the counter electrode 12 is connected to the reference voltage source 305 via the connector 301a. An open circuit voltage is then applied between the working electrode 11 and the counter electrode 12. The phrase "open circuit voltage is applied" may be restated as "the voltage application is switched off."

Figure 10A:
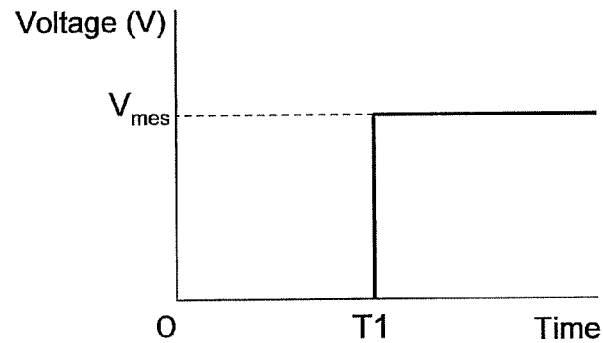
FIG. 10A is a graph of an example of the pattern of voltage application to a sensor chip.

As shown in FIG. 10A, the application time $T_1$ of the open circuit voltage in step S13 is not limited to any specific value, as long as the effect of temperature on the concentration measurement results can be reduced. The time $T_1$ is set to 0.5 to 15 seconds, for example, and preferably 1 to 10 seconds, and more preferably 1 to 5 seconds, and even more preferably about 2 to 3 seconds.

Next, a measurement voltage $V_{mes}$ is applied between the working electrode 11 and the counter electrode 12 under the control of the computer 306 (step S14). The amount of measurement voltage $V_{mes}$ applied here can be varied according to the type of mediator and the type of analyte being measured.

When the measurement voltage $V_{mes}$ is applied, the value of the current flowing between the working electrode 11 and the counter electrode 12 is acquired (step S15). A signal directing the acquisition of a current value is sent from the CPU of the computer 306 to the current/voltage conversion circuit 303. The value of the current that flows between the electrodes as a result of the application of the measurement voltage $V_{mes}$ is converted by the current/voltage conversion circuit 303 into a voltage value. After this, the converted voltage value is converted by the A/D conversion circuit 304 into a digital value and inputted to the CPU, then held in the memory of the computer 306. In this way, the current value at the time of measurement voltage $V_{mes}$ application is acquired in a state of having been converted into a digital voltage value.

The computer 306 calculates the concentration of analyte on the basis of the above-mentioned calibration curve and the digital value thus stored (step S16).

The effect of thus applying open circuit voltage prior to the application of the measurement voltage $V_{mes}$ is that the concentration measurement results are less likely to be affected by temperature.

In the above embodiment, a calibration curve was used for concentration calculation, but a table in which voltage values and concentration are correlated may be used in place of a calibration curve.

5. Other Embodiments—1

Step S13 in FIG. 7 is merely an example of processing that reduces the effect of temperature on concentration measurement results. Thus, step S13 can be replaced by some other processing. The open circuit voltage is an example of voltage that allows electrons to be accumulated in a mediator, but any other voltage with which the effect of electron accumulation can be obtained may be applied instead of an open circuit voltage.

Figure 8:
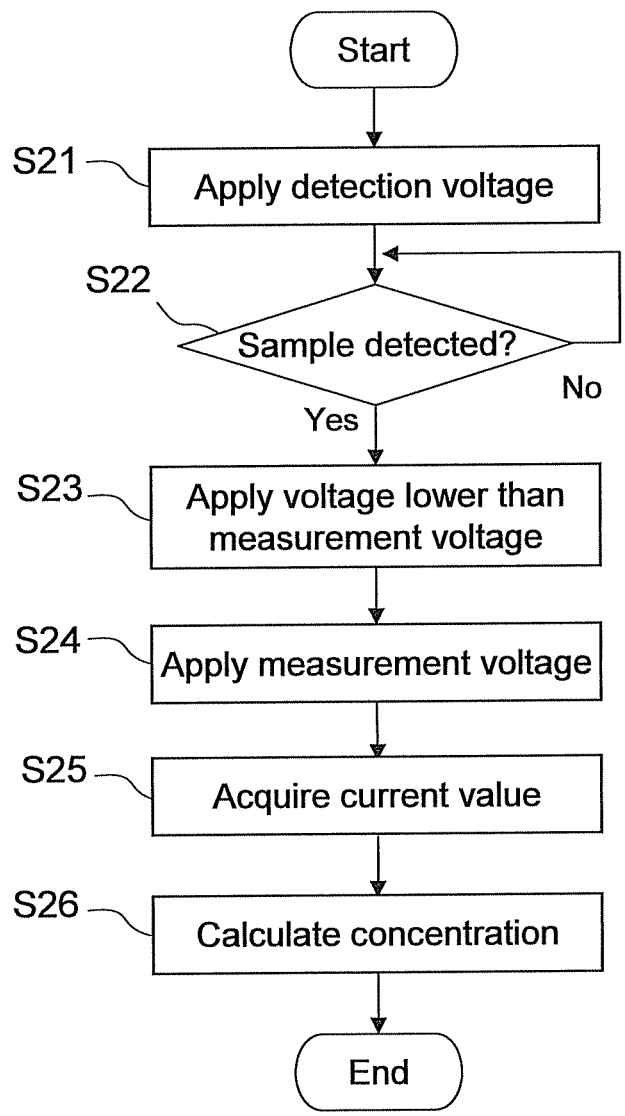
FIG. 8 is a flowchart showing another example of the flow in a method for measuring the concentration of a blood sample.

For example, as shown in FIG. 8, a step S23 may be executed instead of step S13. In step S23, a voltage that is lower than the measurement voltage $V_{mes}$ is applied between the working electrode 11 and the counter electrode 12.

Figure 10B:
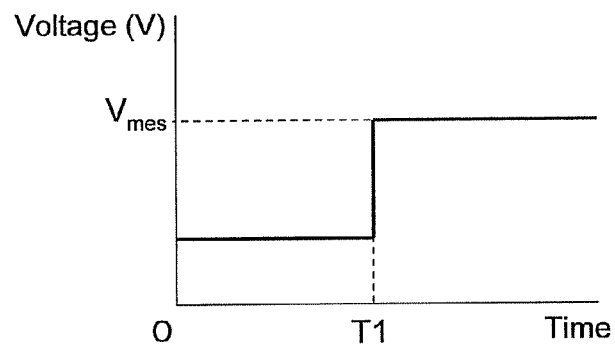
FIG. 10B is a graph of another example of the pattern of voltage application to a sensor chip.
Figure 10C:
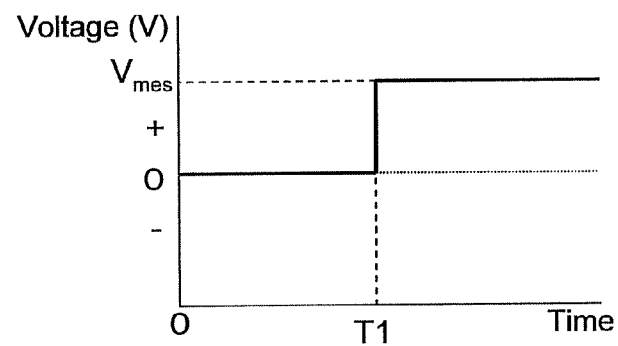
FIG. 10C is a graph of yet another example of the pattern of voltage application to a sensor chip.
Figure 10D:
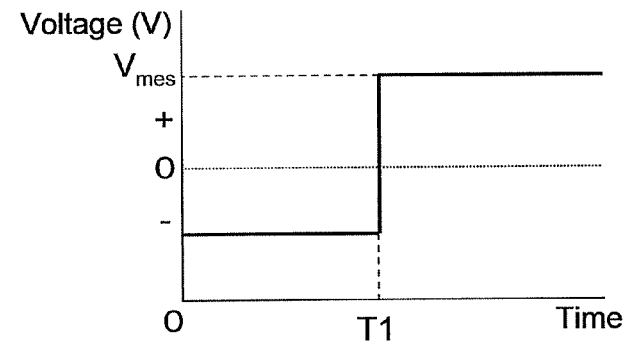
FIG. 10D is a graph of yet another example of the pattern of voltage application to a sensor chip.
Figure 11A:
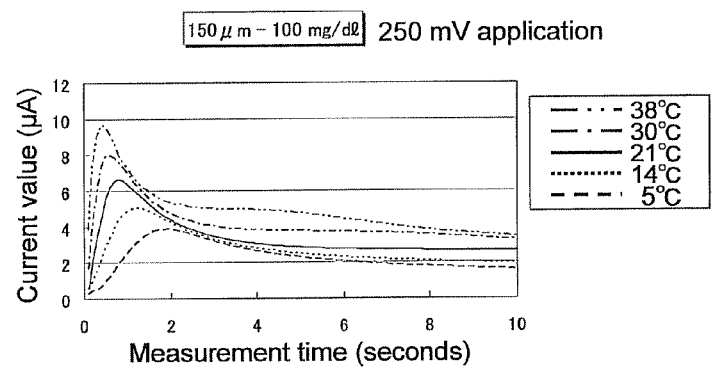
FIG. 11A is a graph of the response current value when the glucose concentration of the sample is 100 mg/dL (milligrams per deciliter), neither the application of open circuit voltage nor the application of low voltage is executed, the applied voltage is 250 mV, and the height of the capillary is 150 μm.
Figure 11B:
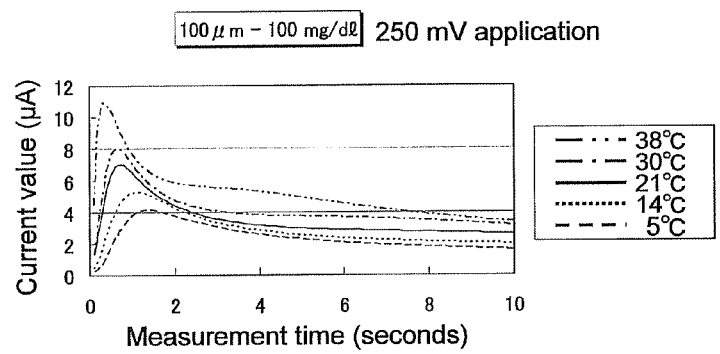
FIG. 11B is a graph of the response current value under the same conditions as in FIG. 11A, except that the height of the capillary is 100 μm.
Figure 11C:
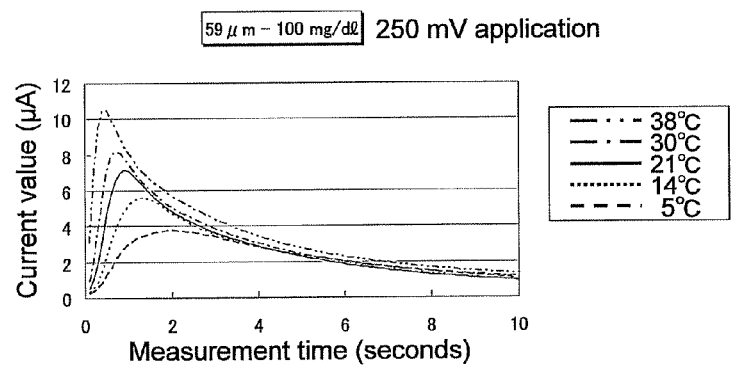
FIG. 11C is a graph of the response current value under the same conditions as in FIG. 11A, except that the height of the capillary is 59 μm.
Figure 11D:
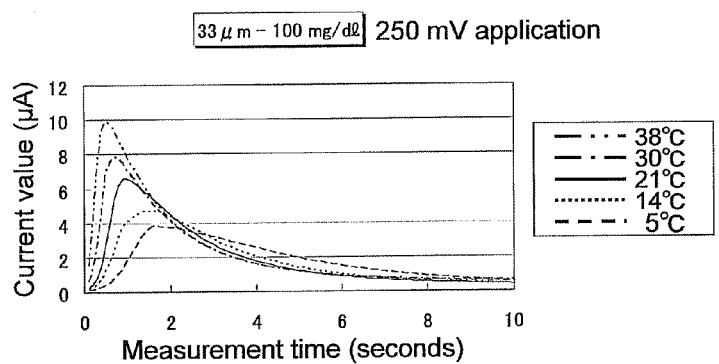
FIG. 11D is a graph of the response current value under the same conditions as in FIG. 11A, except that the height of the capillary is 33 μm.

The "voltage that is lower than the measurement voltage $V_{mes}$" may be any voltage with which electrons can be accumulated in a mediator. For instance, when the measurement voltage $V_{mes}$ is a voltage with positive polarity, the voltage applied in step S23 may be voltage with positive polarity (FIG. 10B), or may be 0 V (FIG. 10C), or may be voltage with an inverse polarity, that is, a negative polarity (FIG. 10D). More specifically, when the measurement voltage $V_{mes}$ is 250 mV, the voltage applied in step S23 may be set to about −200 to 150 mV.

A state in which "electrons are accumulated in a mediator" means a state in which no electrons are transferred from the mediator to the electrodes, or very few are transferred.

6. Other Embodiments—2

Steps S13 and S23 should be executed prior to the acquisition of a current value (steps S15 and S25). Another voltage application step may be executed before or after steps S13 and S23.

Figure 9:
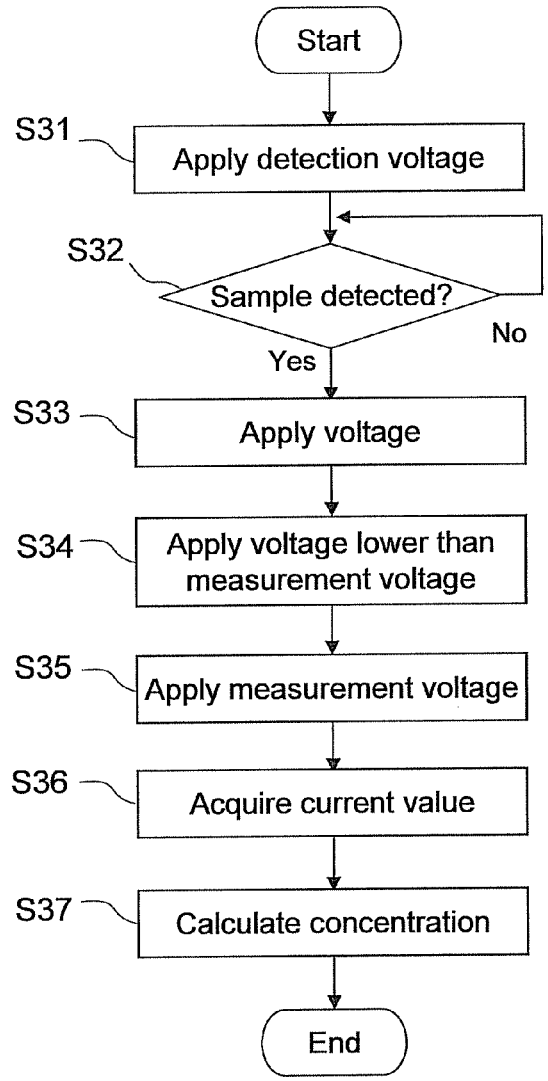
FIG. 9 is a flowchart showing yet another example of the flow in a method for measuring the concentration of a blood sample.

For example, as shown in FIG. 9, another open circuit voltage application step S33 may be executed prior to a step S34 that corresponds to the above-mentioned step S23. There are no particular restrictions on the amount of applied voltage in this step S33 (which could be called a third voltage application step), and may be larger than the measurement voltage $V_{mes}$.

In addition to the embodiment shown in FIG. 9, voltage may be applied in the following combinations and orders.

(1) Third voltage application step/open circuit voltage application step/measurement voltage application step (2) Third voltage application step/open circuit voltage application step/low voltage application step/measurement voltage application step (3) Open circuit voltage application step/low voltage application step/measurement voltage application step In all of these combinations, the low voltage application step may include two or more voltage application steps of mutually different voltage values. Also, in all of these combinations, the open circuit voltage application step and the low voltage application step may be switched around.

The time "0" in FIGS. 10A to 10D may the point at which the introduction of a sample is detected, or may be the point at which a specific length of time has elapsed since this detection. Also, the duration of applying the open circuit voltage, the duration of applying the low voltage, or the combined duration thereof is preferably 0.5 to 10 seconds. For example, it may be set to about 2 to 5 seconds.

As is clear from the description of the above embodiments, the computer 306 and the reference voltage source 305 function as a first voltage applicator for applying the measurement voltage $V_{mes}$ (first voltage) between the working electrode 11 and the counter electrode 12, and a second voltage applicator for applying a second voltage (open circuit voltage, low voltage) prior to the application of the first voltage.

Furthermore, in the above embodiments, a single reference voltage source 305 applies different voltages to the electrodes under the control of the computer 306, but in another constitution, the measurement device 101 may have two or more voltage sources.

Also, the computer 306 functions as a concentration measurement section for measuring the concentration of analyte.

7. Summary

The constitutions discussed in the different sections above can be variously combined. Specifically, the embodiments given above can be rephrased as follows.

1)
A biosensor system with which the concentration of an analyte in a liquid sample is measured using a redox enzyme and an electron-transfer mediator, said biosensor system comprising a sensor chip comprising a capillary into which a liquid sample is introduced, whose height is less than the maximum value of the sum of the diffusion distance of the electron-transfer mediator and the diffusion distance of the analyte at the upper limit of the measurement guaranteed temperature of the biosensor system, a plurality of electrodes disposed within the capillary, and a reagent layer that is disposed within the capillary and includes the electron-transfer mediator; a first voltage applicator that applies a first voltage to the electrodes; a concentration measurement section that measures the concentration of the analyte on the basis of the value of the current flowing through the liquid sample during the first voltage application; and a second voltage applicator that applies a second voltage to the electrodes prior to the application of the first voltage, so that the effect of the temperature of the liquid sample on the measurement results of the concentration measurement section will be diminished.

2)
The biosensor system according to 1) above, wherein the height of the capillary of the sensor chip is less than the maximum value of the sum of the diffusion distance of the electron-transfer mediator and the diffusion distance of the analyte, found from the lower limit of the measurement guaranteed temperature of the biosensor system.

3)
The biosensor system according to 1) or 2) above, wherein the height of the capillary of the sensor chip is set on the basis of the diffusion distances of the electron-transfer mediator and the analyte, each expressed by the following formula (i):

[First Mathematical Formula]

$$d=\sqrt{zDt} \qquad (i)$$

(where d is the diffusion distance, z is an arbitrarily selected constant, D is a diffusion coefficient, and t is time).

4)
The biosensor system according to 3) above,
wherein the constant z in the above Formula (i) satisfies $1 \leq z \leq 4$.

5)
The biosensor system according to any of 1) to 4) above, wherein the second voltage applicator accumulates electrons in the electron-transfer mediator by applying the second voltage.

6)
The biosensor system according to any of 1) to 5) above, wherein the second voltage applicator applies an open circuit voltage as the second voltage.

7)
The biosensor system according to any of 1) to 6) above, wherein the first voltage applicator applies voltage of positive polarity as the first voltage, and the second voltage applicator applies voltage that is lower than the first voltage as the second voltage.

8)
The biosensor system according to any of 1) to 7) above, wherein the concentration measurement section has a calibration curve or table that correlates the current value and the analyte concentration, and calculates the analyte concentration on the basis of the same calibration curve or table even if the temperature of the liquid sample should fluctuate.

9)
The biosensor system according to any of 1) to 8) above, wherein the concentration measurement section measures the analyte concentration on the basis of the current value at a point when no more than 10 seconds have elapsed since the start of the application of the second voltage, and the height of the capillary of the sensor chip is no more than 90 μm.

10)
The biosensor system according to any of 1) to 9), wherein the electrodes are disposed on two faces that are mutually opposite in the height direction of the capillary.

11)
A method for measuring the concentration of an analyte in a liquid sample using a redox enzyme or an electron-transfer mediator, which is executed by a biosensor system having a sensor chip comprising a capillary into which a liquid sample is introduced, whose height is less than the maximum value of the sum of the diffusion distance of the electron-transfer mediator and the diffusion distance of the analyte at the upper limit of the measurement guaranteed temperature of the biosensor system, a plurality of electrodes disposed within the capillary, and a reagent layer that is disposed within the capillary and includes the electron-transfer mediator, said measurement method comprising a first voltage application step of applying a first voltage to the electrodes, a current detection step of detecting the value of current flowing through the liquid sample during the application of the first voltage, a concentration measurement step of measuring the concentration of the analyte on the basis of the current value, and a second voltage application step of applying a second voltage to the electrodes prior to the detection of the current value, so that the temperature of the liquid sample will have less effect on the measurement results of the concentration measurement section.

12)
The measurement method according to 11) above, wherein the second voltage is set such that electrons will be accumulated in the electron-transfer mediator by the application of the second voltage.

13)
The measurement method according to 11) or 12), wherein the average molecular weight is an open circuit voltage.

14)
The measurement method according to any of 11) to 13) above, wherein the first voltage is a voltage of positive polarity, and the second voltage is a voltage that is lower than the first voltage.

15)
The measurement method according to any of 11) to 14) above, wherein the concentration measurement step includes a calculation step of using a calibration curve or table that correlates the current value and the analyte concentration, and calculating the analyte concentration on the basis of the same calibration curve or table even if the temperature of the liquid sample should fluctuate.

16)
The measurement method according to any of 11) to 15) above, wherein the height of the capillary of the sensor chip is no more than 90 μm, and in the concentration measurement step, the concentration of the analyte is measured on the basis of the current value at a point when no more than 10 seconds have elapsed since the start of the application of the second voltage.

EXPERIMENT EXAMPLES

The present invention will now be described in more specific terms through experiment examples.

The above-mentioned biosensor system 100 was used in the following experiment examples. The sensor chip 200 shown in FIGS. 2, 3, and 5A was used as the sensor chip. The sensor chip 200 is constituted as follows.

The capillary 40 was designed so that it was 1.2 mm wide, 4.0 mm long (deep), and 33 to 150 μm high. The height H was confirmed by slicing the sensor chip 200 and using a microscope of measure the distance from the working electrode 11 to the ceiling of the capillary 40 (the inner face of the cover 203).

Polyethylene terephthalate was used for the insulated board 201. The electrodes 11 to 13 were each formed by vapor depositing palladium on the insulated board 201, and making slits with a laser so that the surface area of the working electrode 11 inside the capillary 40 was 1.0 mm$^2$, and the surface area of the counter electrode 12 inside the capillary 40 was 1.2 mm$^2$.

The reagent layer 20 was formed as follows. Glucose dehydrogenase, potassium ferricyanide (made by Kanto Chemical), and taurine (made by Nakalai Tesque) were used. An aqueous solution was prepared by dissolving glucose dehydrogenase so that the glucose dehydrogenase concentration in the reagent layer 20 would be 2.0 U/sensor chip. The potassium ferricyanide and the taurine were dissolved in this aqueous solution in amounts of 1.7 wt % and 1.0 wt %, respectively, to obtain a reagent solution. This reagent solution was applied over the insulated board 201, and the coating was dried in an atmosphere with a humidity of 45% and a temperature of 21° C.

In the following experiment examples, unless otherwise specified, a time of "0" on the graph is the point when the introduction of a sample was detected. Also, the temperature in the following experiment examples is the air temperature of the measurement environment. Blood adjusted to a specific glucose value was used as the sample to be measured.

Experiment Example 1

In this experiment example, the same processing as in FIG. 7 was performed with the above-mentioned biosensor system 100, except that step S13 was omitted. That is, steps S11, S12, and S14 to S16 in FIG. 7 were performed. More specifically, after step S12, a constant voltage of 250 mV was applied, and the response current value (sometimes referred to simply as "current value") was measured. The current value for each sensor chip was measured using sensor chips with different heights H of the capillary 40. More specifically, the height H of the capillary 40 was either 150 μm, 100 μm, 59 μm, or 33 μm.

Figure 12A:
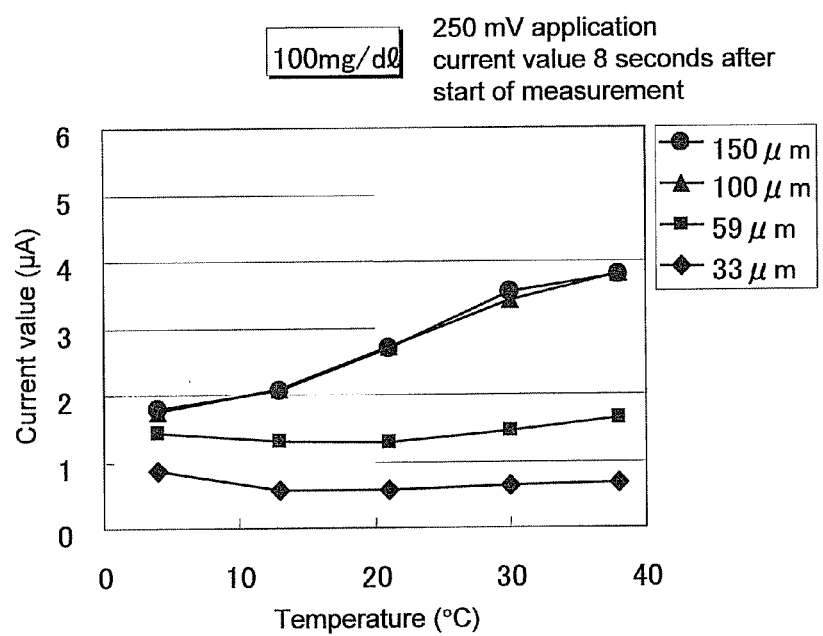
FIG. 12A is a graph of the response current value when 8 seconds have elapsed in FIGS. 11A to 11D.
Figure 12B:
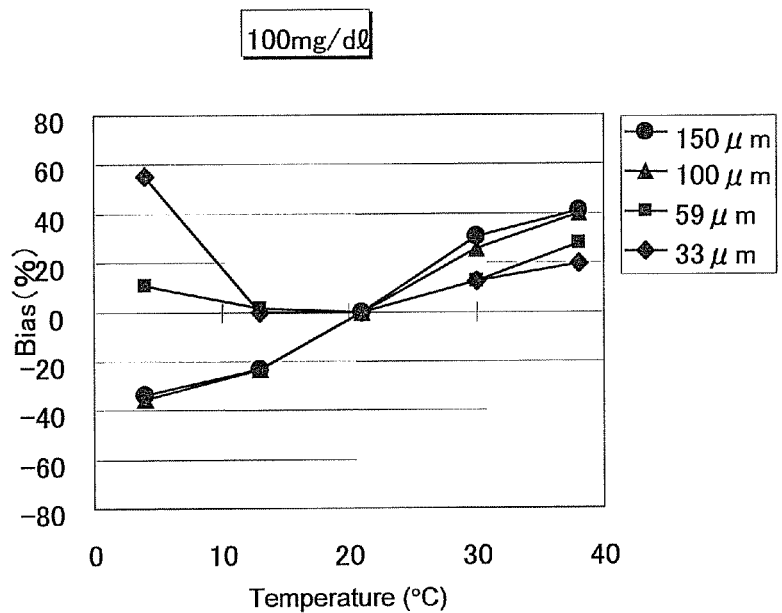
FIG. 12B is a graph of the variance in the response current value under the various temperature conditions in FIG. 12A, using the response current value at 21° C. as a reference.
Figure 13A:
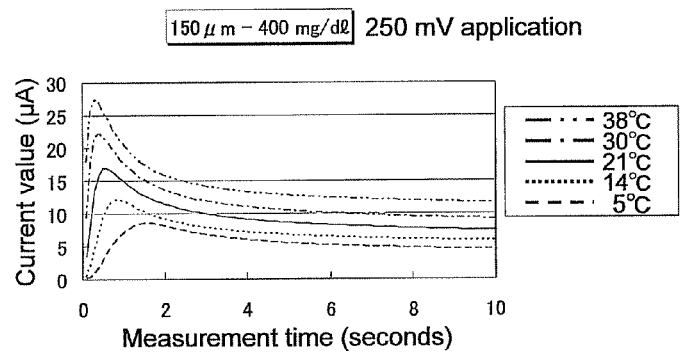
FIG. 13A is a graph of the response current value when the glucose concentration of the sample is 400 mg/dL, neither the application of open circuit voltage nor the application of low voltage is executed, the applied voltage is 250 mV, and the height of the capillary is 150 μm.
Figure 13B:
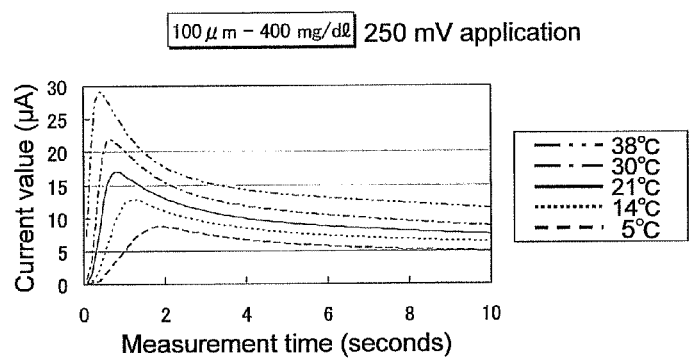
FIG. 13B is a graph of the response current value under the same conditions as in FIG. 13A, except that the height of the capillary is 100 μm.
Figure 13C:
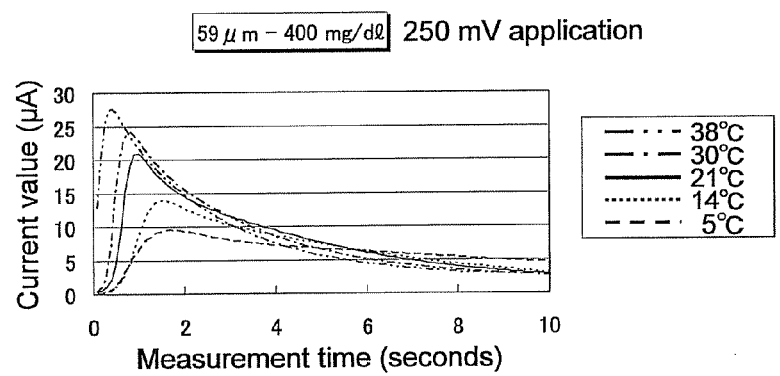
FIG. 13C is a graph of the response current value under the same conditions as in FIG. 13A, except that the height of the capillary is 59 μm.
Figure 13D:
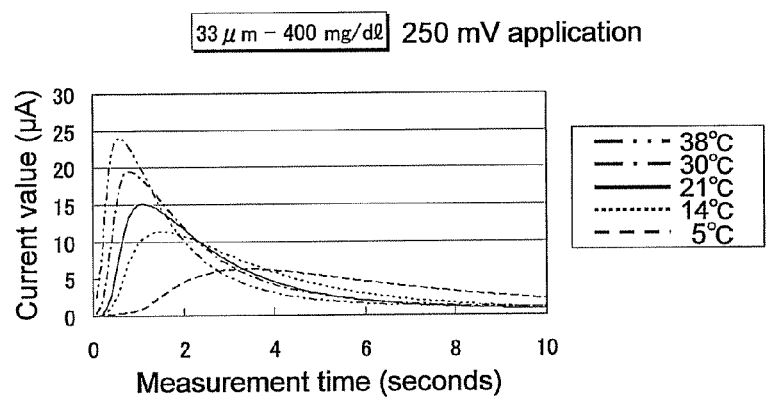
FIG. 13D is a graph of the response current value under the same conditions as in FIG. 13A, except that the height of the capillary is 33 μm.
Figure 14A:
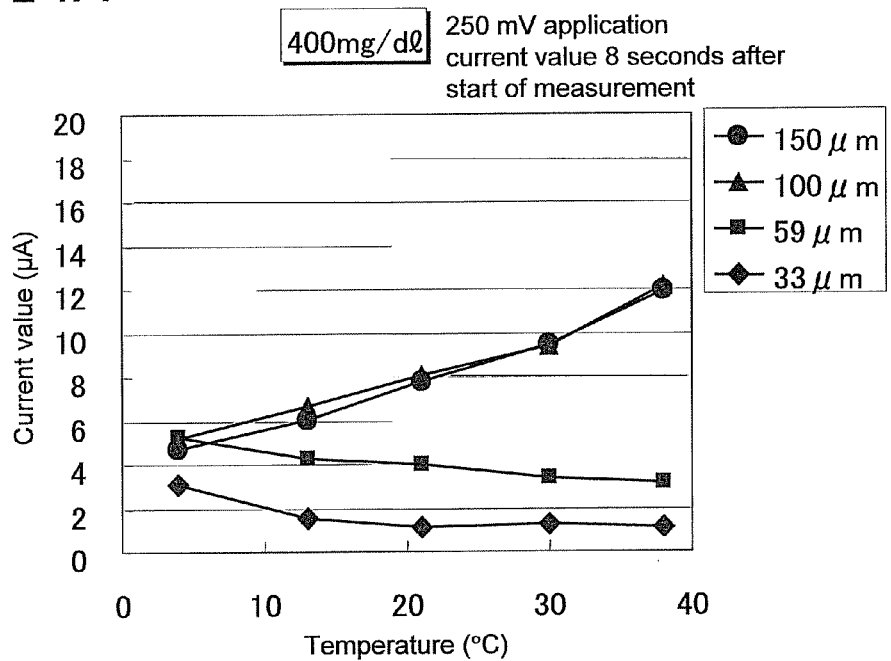
FIG. 14A is a graph of the response current value when 8 seconds have elapsed in FIGS. 13A to 13D.
Figure 14B:
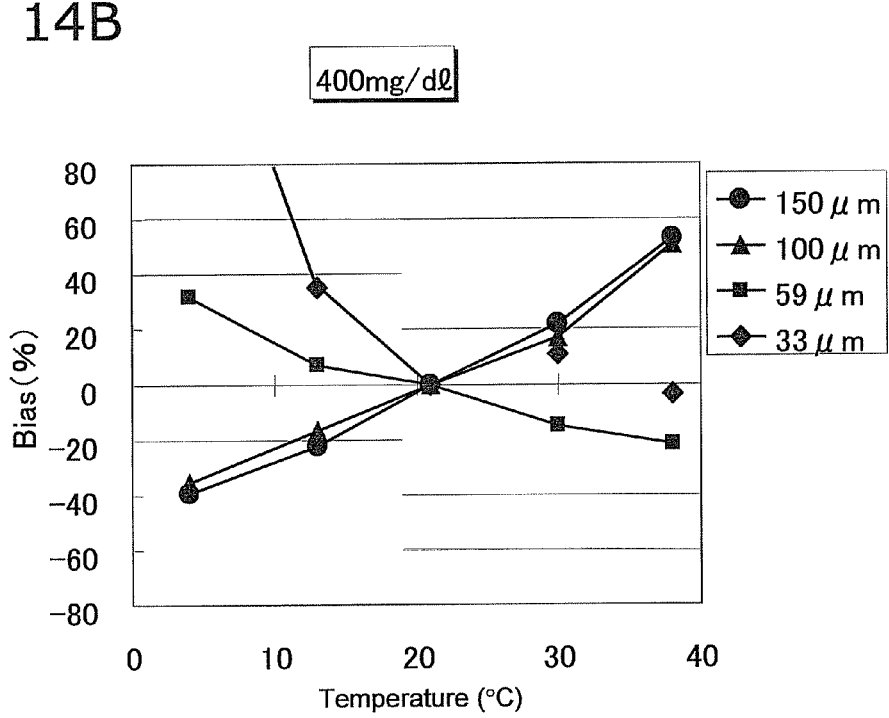
FIG. 14B is a graph of the variance in the response current value under the various temperature conditions in FIG. 14A, using the response current value at 21° C. as a reference.
Figure 15A:
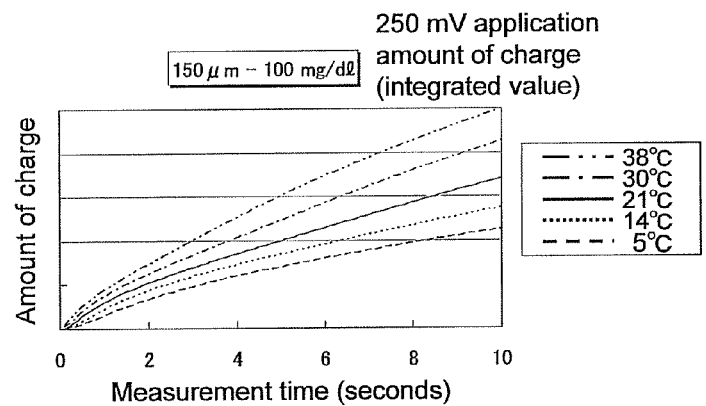
FIG. 15A is a graph of the amount of charge obtained by adding up the measurement results for response current value in FIG. 11A every 0.1 second.
Figure 15B:
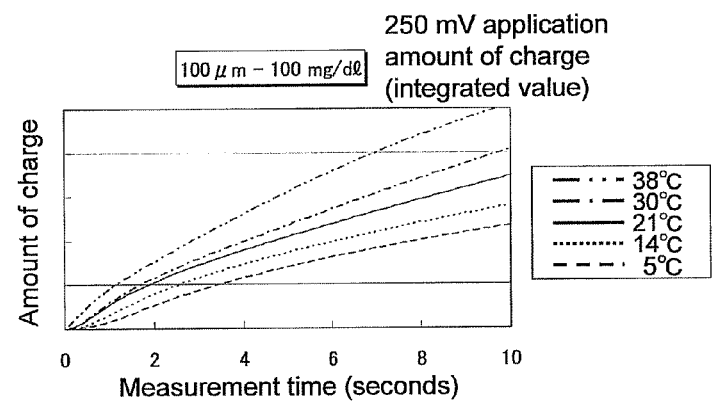
FIG. 15B is a graph of the amount of charge obtained by adding up the measurement results for response current value in FIG. 11B every 0.1 second.
Figure 15C:
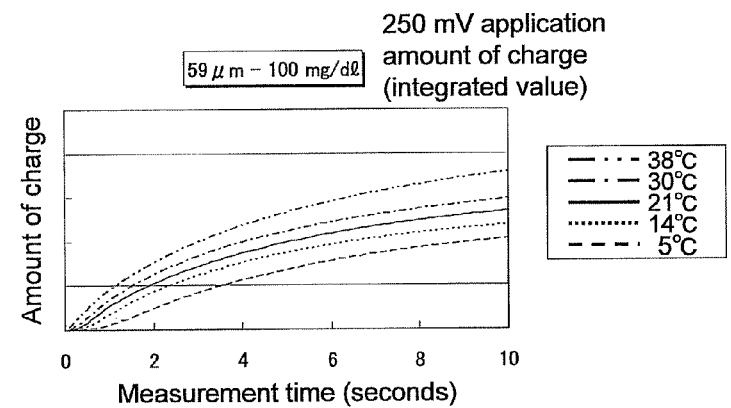
FIG. 15C is a graph of the amount of charge obtained by adding up the measurement results for response current value in FIG. 11C every 0.1 second.
Figure 15D:
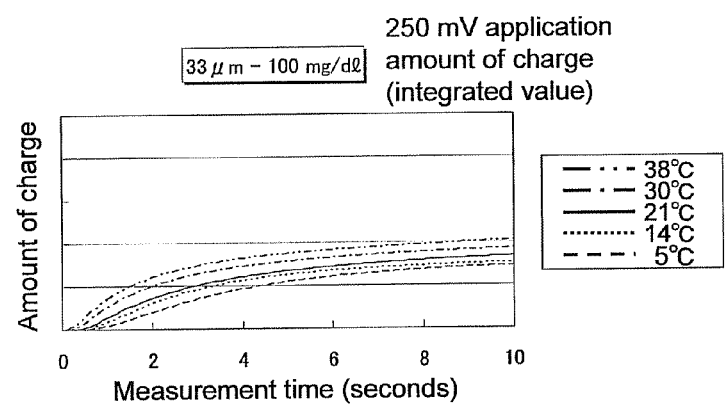
FIG. 15D is a graph of the amount of charge obtained by adding up the measurement results for response current value in FIG. 11D every 0.1 second.

FIGS. 11A to 11D show the results of measuring current value using blood with a glucose concentration of 100 mg/dL (deciliter). FIGS. 13A to 13D show the results of measuring current value using blood with a glucose concentration of 400 mg/dL (deciliter). FIG. 12A and FIGS. 11A to 11D are graphs of the current value at a point when 8 seconds have elapsed. FIG. 12B is a graph of the variance in the current value at various temperatures, when the current value at 21° C. in FIG. 12A was 0%.

As shown in FIGS. 11A and 11B and FIGS. 13A and 13B, when the height H is high, the current value will be large under high temperature conditions and will be small under low temperature conditions regardless of the measurement time (the elapsed time after the start of the reaction).

Meanwhile, as shown in FIGS. 11C and 11D and FIGS. 13C and 13D, when the height H is low (59 μm or 33 μm), a larger current value was measured under high temperature conditions than under low temperature conditions while the measurement time was short, but when the measurement time was longer, the a larger current value was measured under low temperature conditions than under high temperature conditions. The reason for this inversion seems to be that with a finite diffusion system, under high temperature conditions more of the substrate (glucose) is consumed in a short period, so the substrate is used up over time, but under low temperature conditions there is substrate left over.

Because this inversion occurs, as shown in FIGS. 12A and 12B and FIGS. 14A and 14B, in this experiment example there was a large variance in the current value when the temperature changed even when the height H was 33 μm, that is, when the height H was low.

Experiment Example 2

Figure 16A:
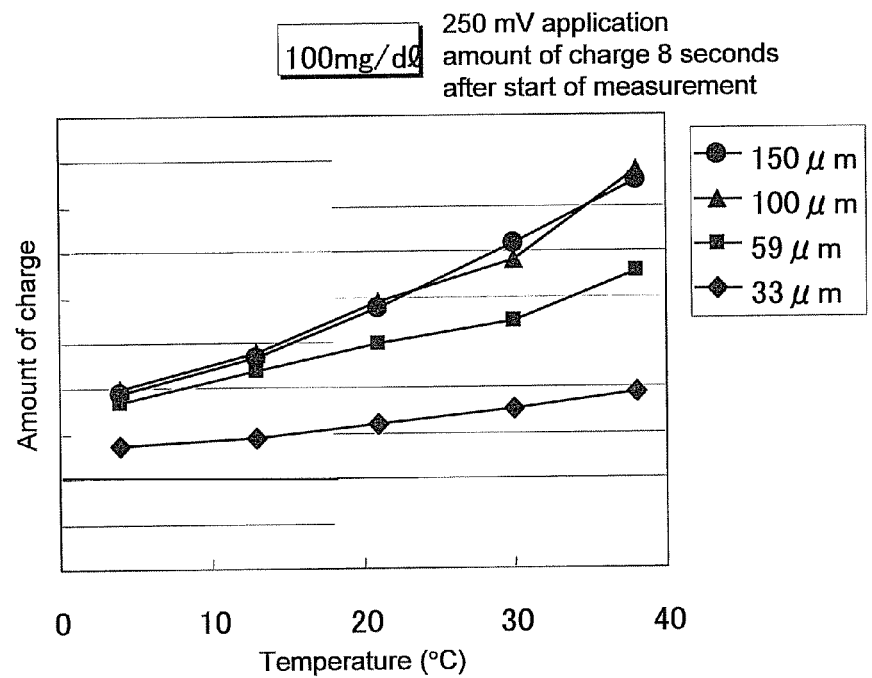
FIG. 16A is a graph of the amount of charge when 8 seconds have elapsed in FIGS. 15A to 15D.
Figure 16B:
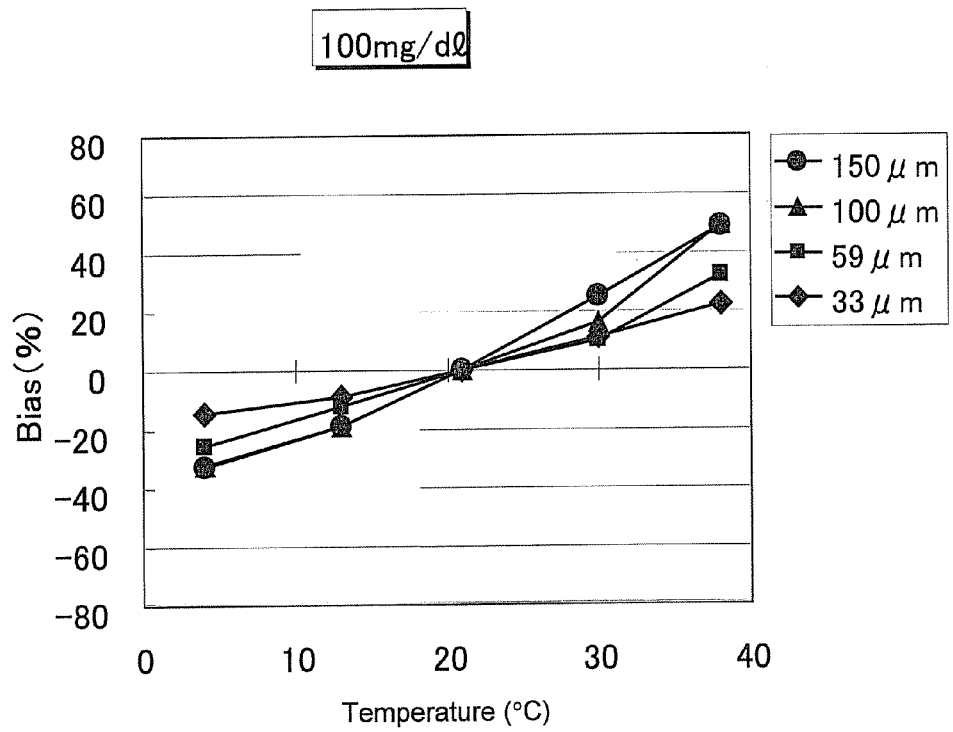
FIG. 16B is a graph of the variance in the amount of charge under the various temperature conditions in FIG. 16A, using the amount of charge at 21° C. as a reference.
Figure 17A:
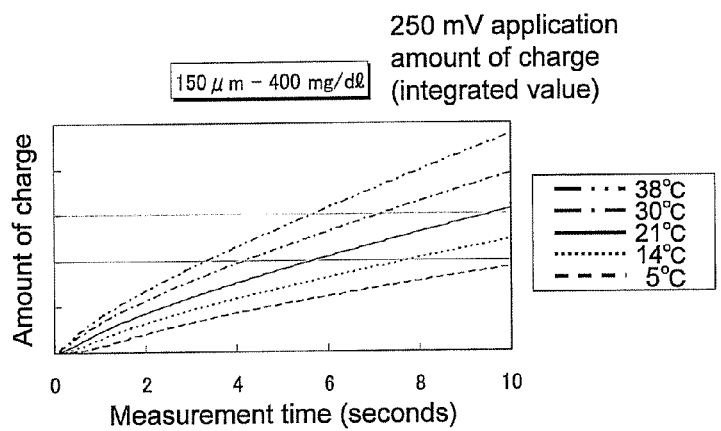
FIG. 17A is a graph of the amount of charge obtained by adding up the measurement results for response current value in FIG. 13A every 0.1 second.
Figure 17B:
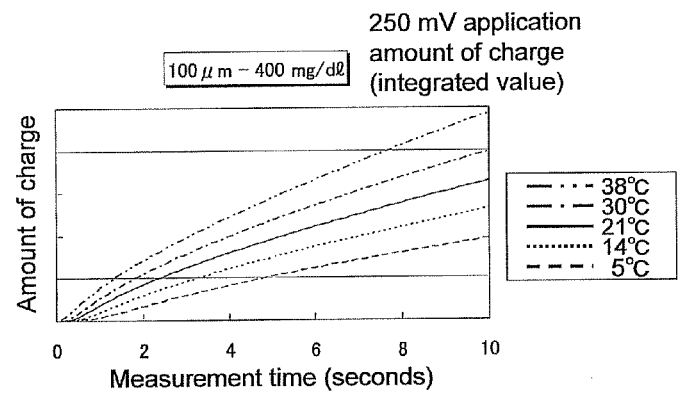
FIG. 17B is a graph of the amount of charge obtained by adding up the measurement results for response current value in FIG. 13B every 0.1 second.
Figure 17C:
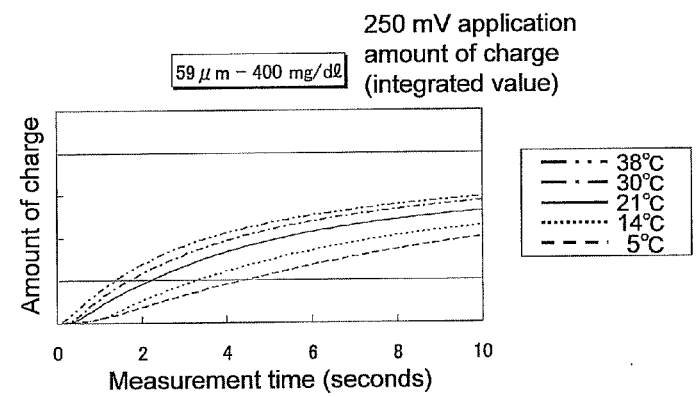
FIG. 17C is a graph of the amount of charge obtained by adding up the measurement results for response current value in FIG. 13C every 0.1 second.
Figure 17D:
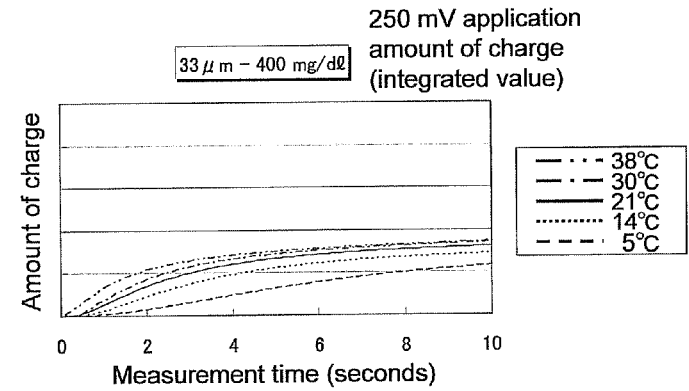
FIG. 17D is a graph of the amount of charge obtained by adding up the measurement results for response current value in FIG. 13D every 0.1 second.
Figure 18A:
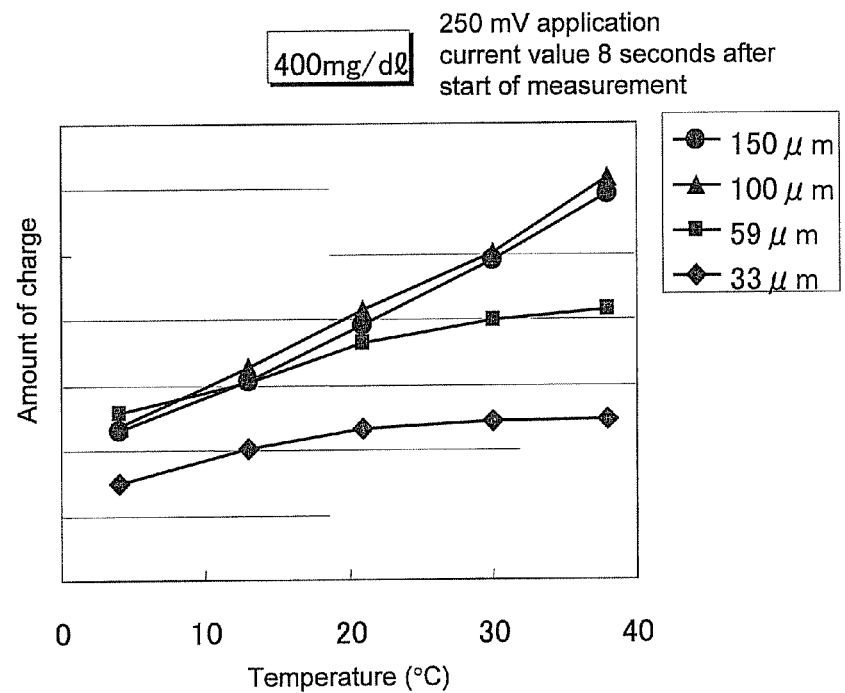
FIG. 18A is a graph of the amount of charge when 8 seconds have elapsed in FIGS. 17A to 17D.
Figure 18B:
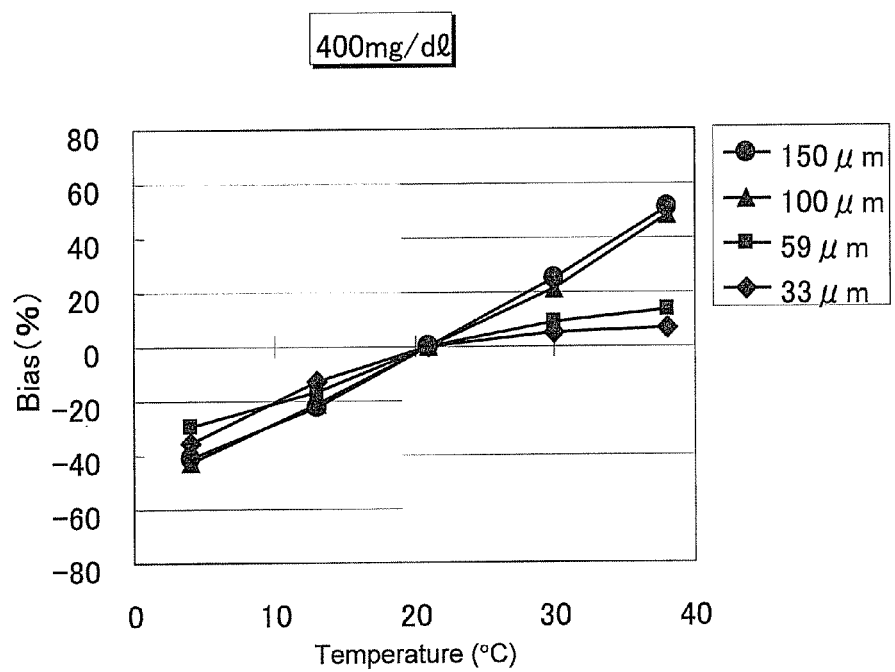
FIG. 18B is a graph of the variance in the amount of charge under the various temperature conditions in FIG. 18A, using the amount of charge at 21° C. as a reference.
Figure 19A:
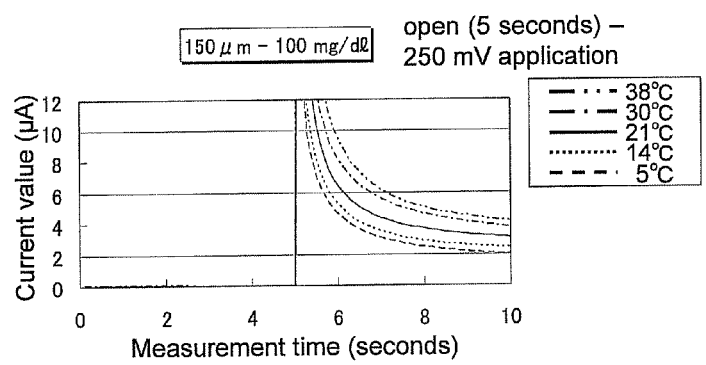
FIG. 19A is a graph of the response current value when the glucose concentration of the sample is 100 mg/dL (milligrams per deciliter), the voltage application conditions are open (5 seconds)—250 mV, and the height of the capillary is 150 μm.
Figure 19B:
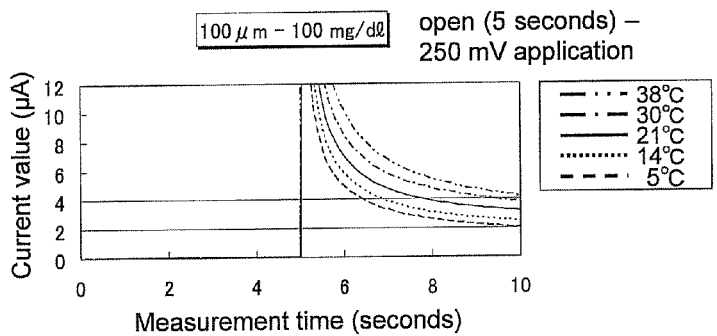
FIG. 19B is a graph of the response current value under the same conditions as in FIG. 19A, except that the height of the capillary is 100 μm.
Figure 19C:
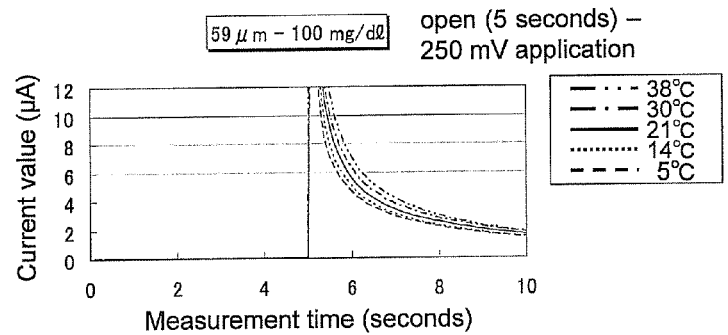
FIG. 19C is a graph of the response current value under the same conditions as in FIG. 19A, except that the height of the capillary is 59 μm.
Figure 19D:
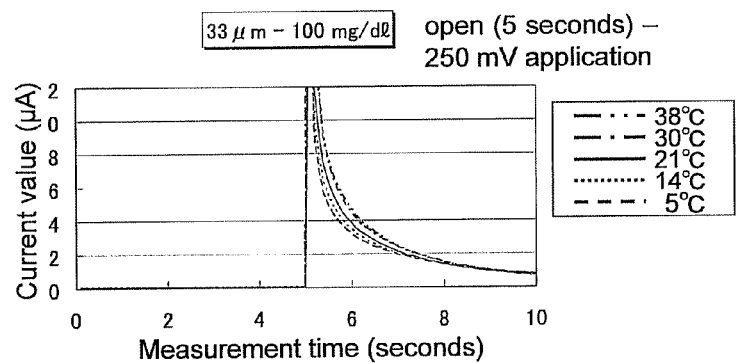
FIG. 19D is a graph of the response current value under the same conditions as in FIG. 19A, except that the height of the capillary is 33 μm.

The measurement results for current value in Experiment Example 1 were integrated every 0.1 second to calculate the amount of charge. The results are shown in FIGS. 15A to 15D and FIGS. 17A to 17D. FIGS. 15A to 15D correspond to FIGS. 11A to 11D, and FIGS. 17A to 17D correspond to FIGS. 13A to 13D. FIGS. 16A and 18A are graphs of the amount of charge after 8 seconds have elapsed in FIGS. 15A to 15D and FIGS. 17A to 17D, respectively, and FIGS. 16B and 18B are graphs of the variance in the amount of charge due to temperature in FIGS. 16A and 18A, respectively.

As shown in these graphs, even if the height H was low, there was a large amount of variance in the amount of charge when a constant voltage was applied.

Experiment Example 3

The response current value was measured with the measurement voltage in step S14 set at 250 mV and the period in which the applied voltage in step S13 in FIG. 7 was an open circuit voltage (open). The conditions other than voltage, namely, the height H of the capillary, the temperature conditions, the glucose concentration of the sample, and so forth, were the same as the conditions in Experiment Example 1.

FIGS. 19A to 19D show the measurement results for current value when blood with a glucose concentration of 100 mg/dL (deciliter) was used as the sample. As shown in FIGS. 11A to 11D, the lower was the height of the capillary 40, the less variance there was in the measurement results due to environment temperature. In particular, there was little variance when the height H was 59 μm or less, and variance was least at 33 μm.

Figure 20A:
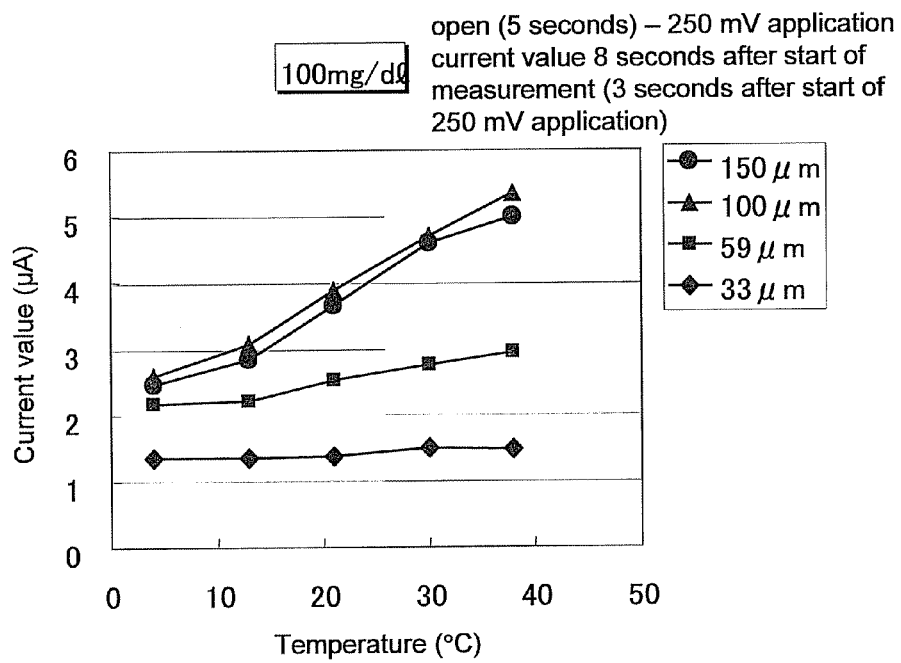
FIG. 20A is a graph of the response current value when 8 seconds have elapsed in FIGS. 19A to 19D.
Figure 20B:
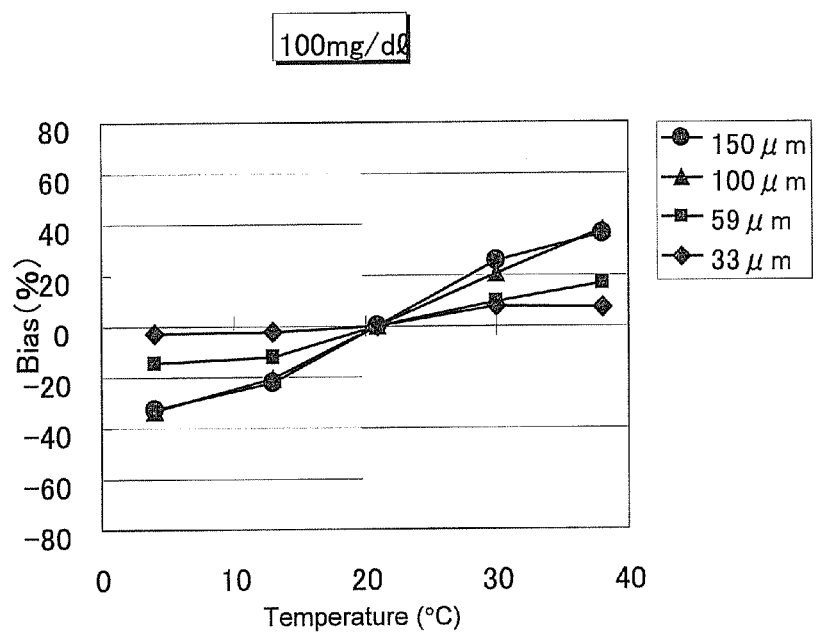
FIG. 20B is a graph of the variance in the response current value under the various temperature conditions in FIG. 20A, using the response current value at 21° C. as a reference.
Figure 21A:
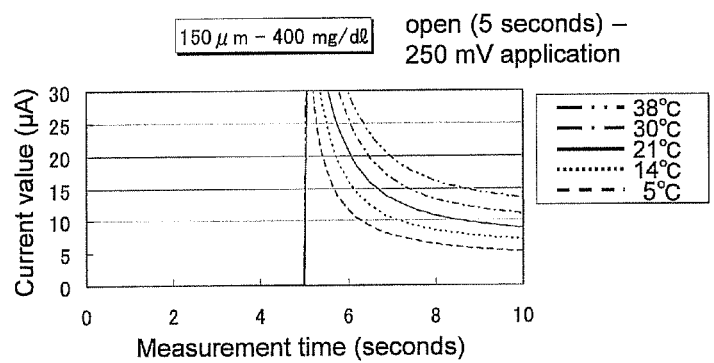
FIG. 21A is a graph of the response current value when the glucose concentration of the sample is 400 mg/dL (milligrams per deciliter), the voltage application conditions are open (5 seconds)—250 mV, and the height of the capillary is 150 μm.
Figure 21B:
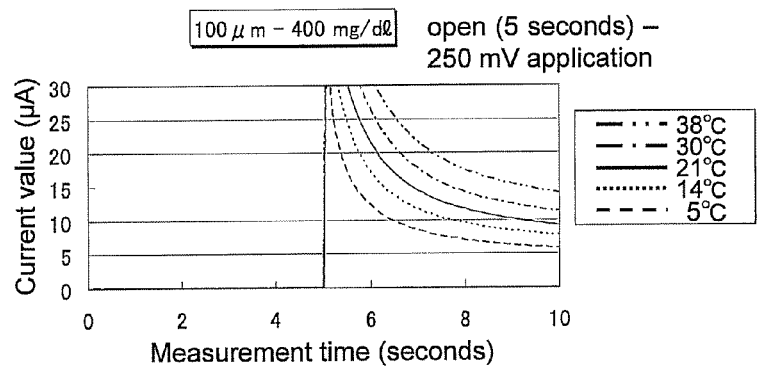
FIG. 21B is a graph of the response current value under the same conditions as in FIG. 21A, except that the height of the capillary is 100 μm.
Figure 21C:
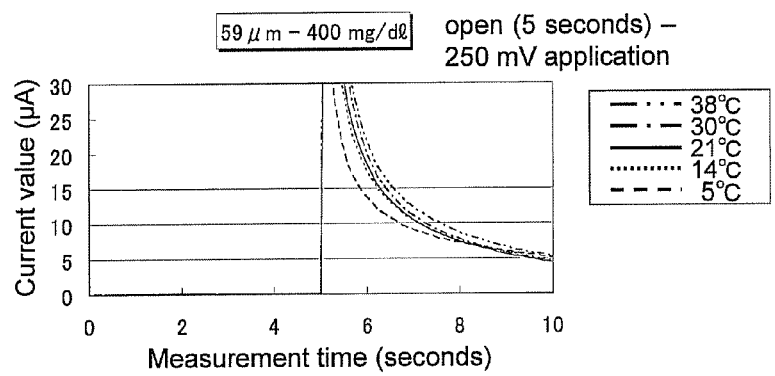
FIG. 21C is a graph of the response current value under the same conditions as in FIG. 21A, except that the height of the capillary is 59 μm.
Figure 21D:
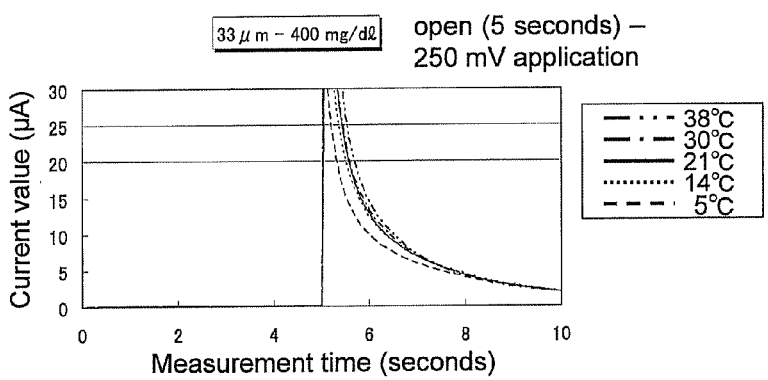
FIG. 21D is a graph of the response current value under the same conditions as in FIG. 21A, except that the height of the capillary is 33 μm.
Figure 22A:
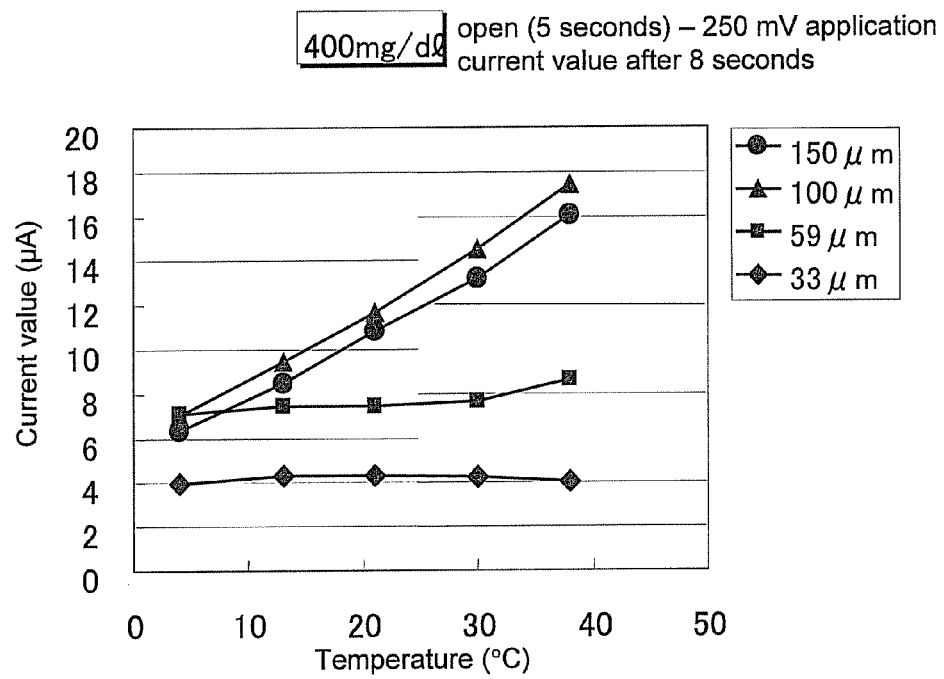
FIG. 22A is a graph of the response current value when 8 seconds have elapsed in FIGS. 21A to 21D.
Figure 22B:
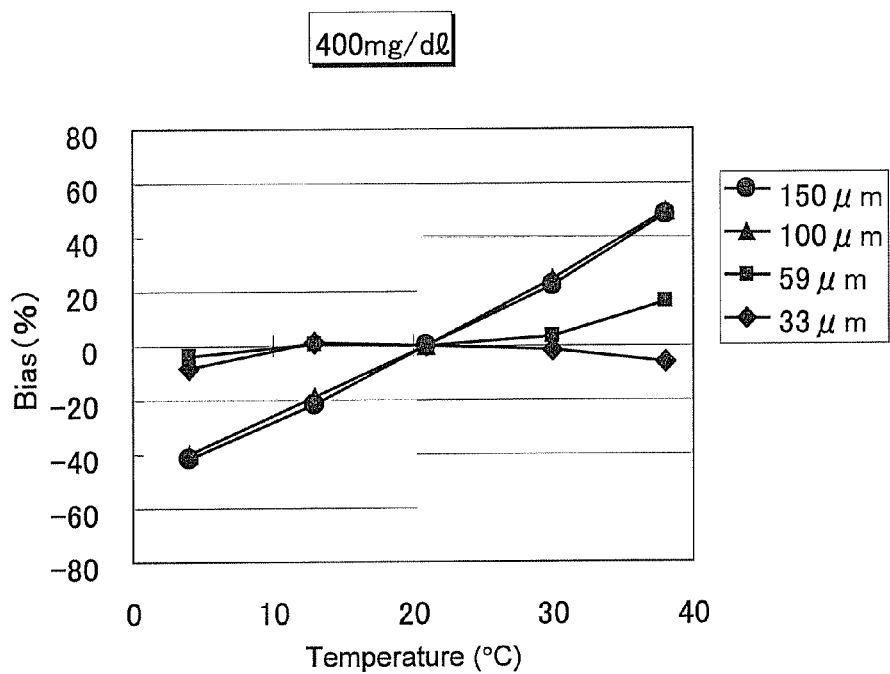
FIG. 22B is a graph of the variance in the response current value under the various temperature conditions in FIG. 22A, using the response current value at 21° C. as a reference.
Figure 23A:
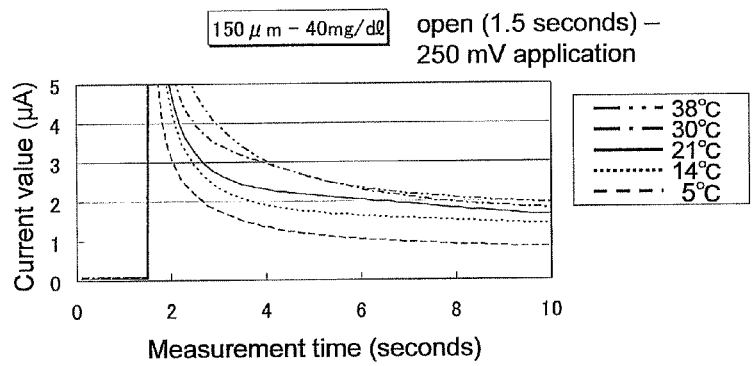
FIG. 23A is a graph of the response current value when the glucose concentration of the sample is 40 mg/dL (milligrams per deciliter), the voltage application conditions are open (1.5 seconds)—250 mV, and the height of the capillary is 150 μm.
Figure 23B:
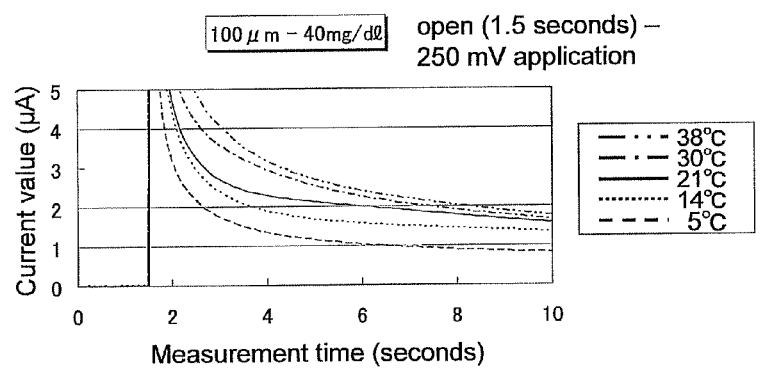
FIG. 23B is a graph of the response current value under the same conditions as in FIG. 23A, except that the height of the capillary is 100 μm.
Figure 23C:
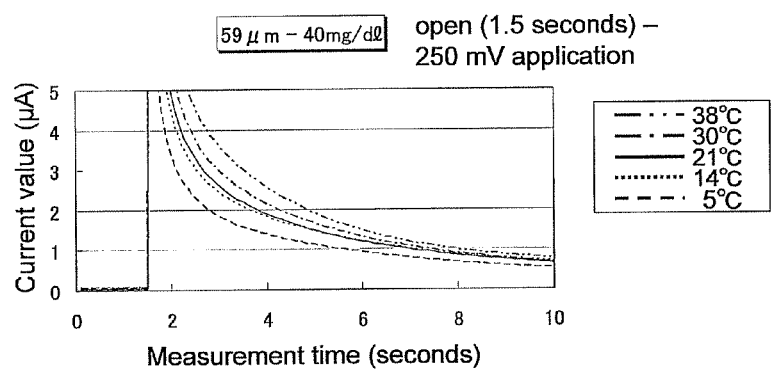
FIG. 23C is a graph of the response current value under the same conditions as in FIG. 23A, except that the height of the capillary is 59 μm.
Figure 23D:
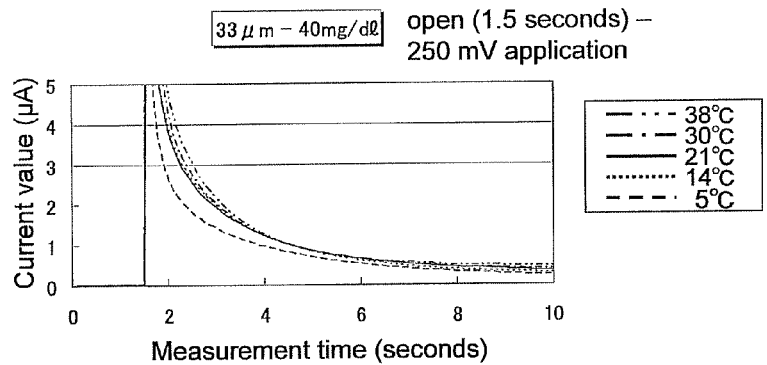
FIG. 23D is a graph of the response current value under the same conditions as in FIG. 23A, except that the height of the capillary is 33 μm.
Figure 24A:
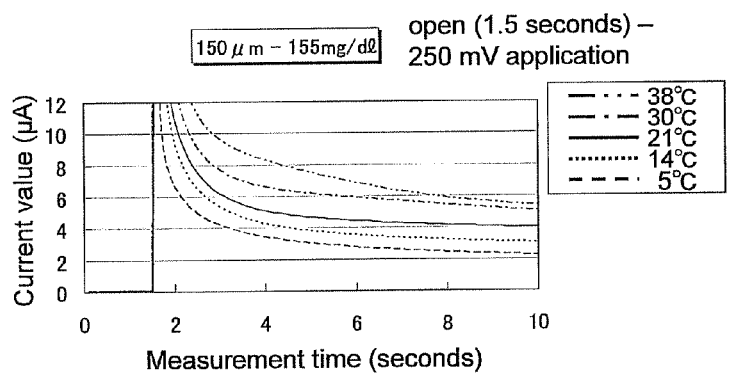
FIG. 24A is a graph of the response current value under the same conditions as in FIG. 23A, except that the glucose concentration of the sample is 155 mg/dL.
Figure 24B:
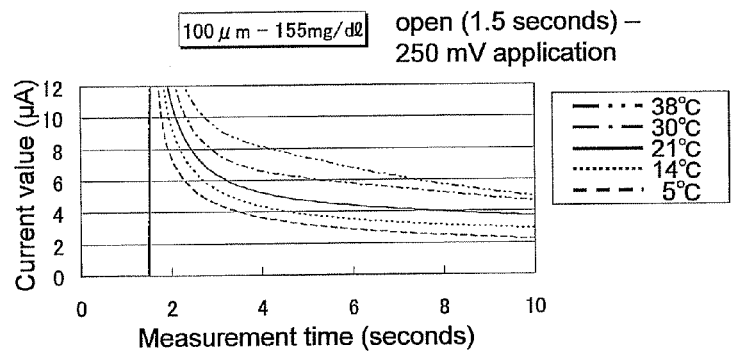
FIG. 24B is a graph of the response current value under the same conditions as in FIG. 24A, except that the height of the capillary is 100 μm.
Figure 24C:
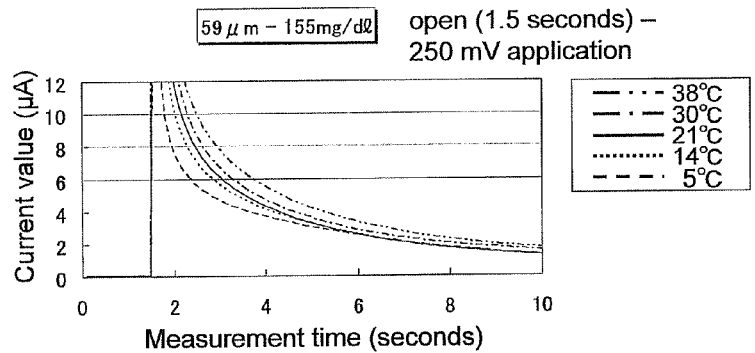
FIG. 24C is a graph of the response current value under the same conditions as in FIG. 24A, except that the height of the capillary is 59 μm.
Figure 24D:
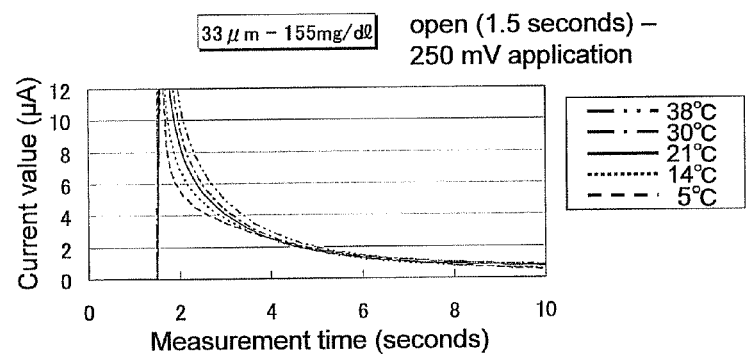
FIG. 24D is a graph of the response current value under the same conditions as in FIG. 24A, except that the height of the capillary is 33 μm.
Figure 25A:
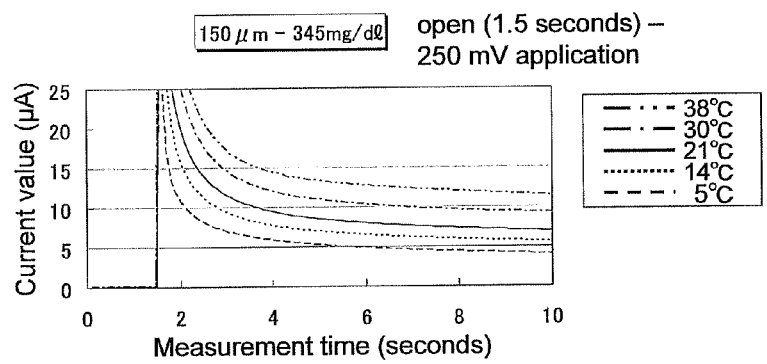
FIG. 25A is a graph of the response current value under the same conditions as in FIG. 23A, except that the glucose concentration of the sample is 345 mg/dL.
Figure 25B:
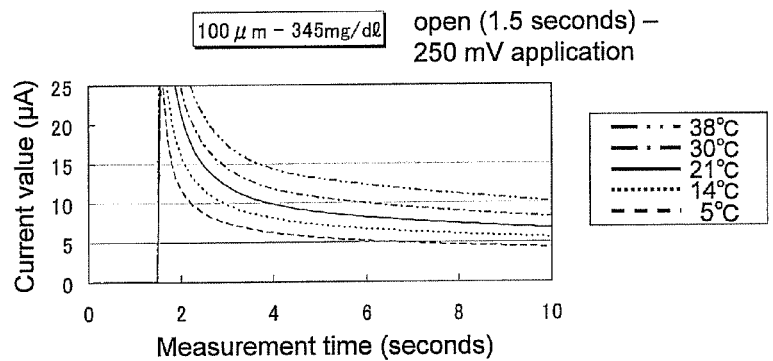
FIG. 25B is a graph of the response current value under the same conditions as in FIG. 25A, except that the height of the capillary is 100 μm.
Figure 25C:
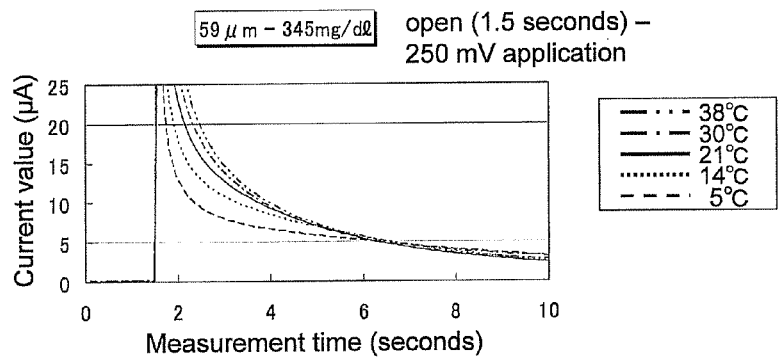
FIG. 25C is a graph of the response current value under the same conditions as in FIG. 25A, except that the height of the capillary is 59 μm.
Figure 25D:
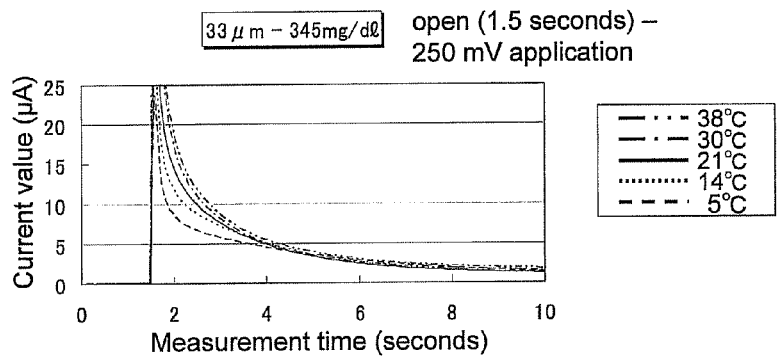
FIG. 25D is a graph of the response current value under the same conditions as in FIG. 25A, except that the height of the capillary is 33 μm.
Figure 26A:
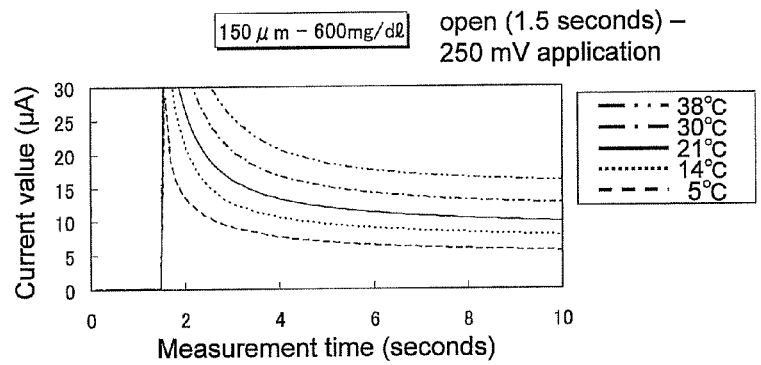
FIG. 26A is a graph of the response current value under the same conditions as in FIG. 23A, except that the glucose concentration of the sample is 600 mg/dL.
Figure 26B:
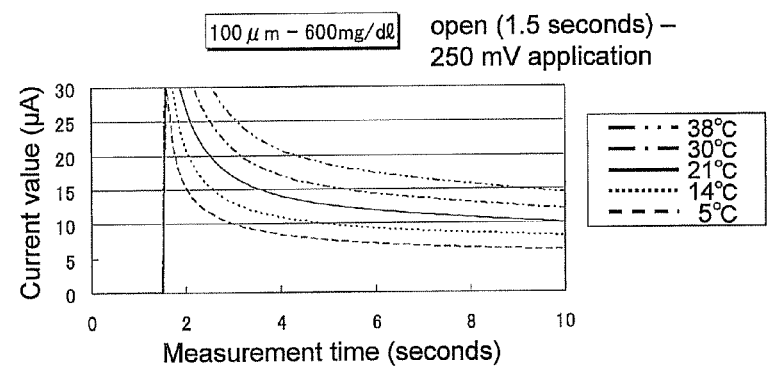
FIG. 26B is a graph of the response current value under the same conditions as in FIG. 26A, except that the height of the capillary is 100 μm.
Figure 26C:
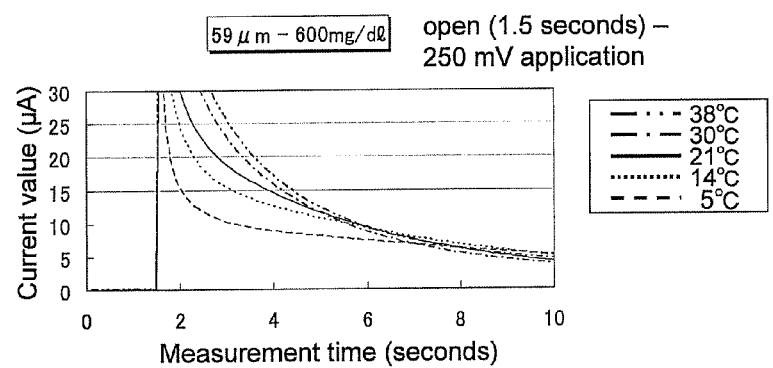
FIG. 26C is a graph of the response current value under the same conditions as in FIG. 26A, except that the height of the capillary is 59 μm.
Figure 26D:
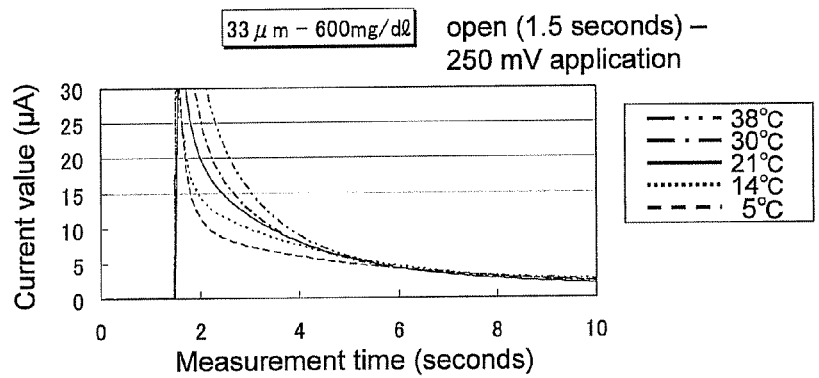
FIG. 26D is a graph of the response current value under the same conditions as in FIG. 26A, except that the height of the capillary is 33 μm.
Figure 27A:
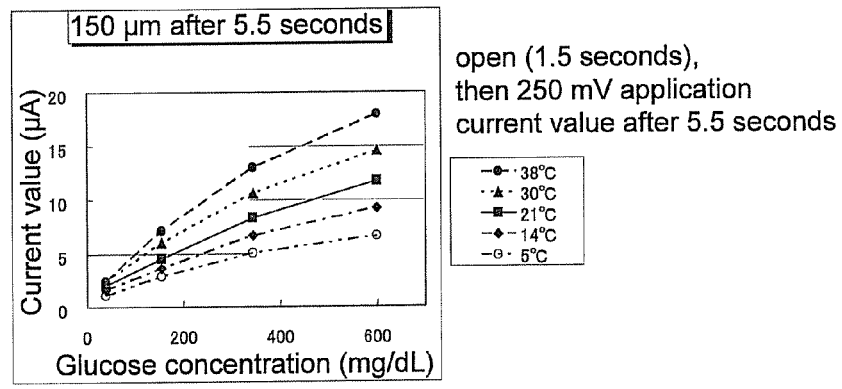
FIG. 27A is a graph of the relation between temperature, glucose concentration, and the current value when 5.5 seconds have elapsed (4 seconds after the start of application of a voltage of 250 mV), when the height of the capillary is 150 μm, on the basis of FIGS. 23A, 24A, 25A, and 26A.
Figure 27B:
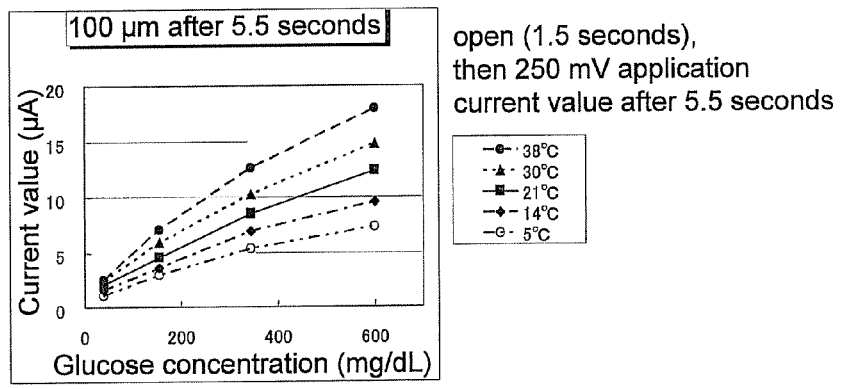
FIG. 27B is a graph of the relation between temperature, glucose concentration, and the current value when 5.5 seconds have elapsed (4 seconds after the start of application of a voltage of 250 mV), when the height of the capillary is 100 μm, on the basis of FIGS. 23B, 24B, 25B, and 26B.
Figure 27C:
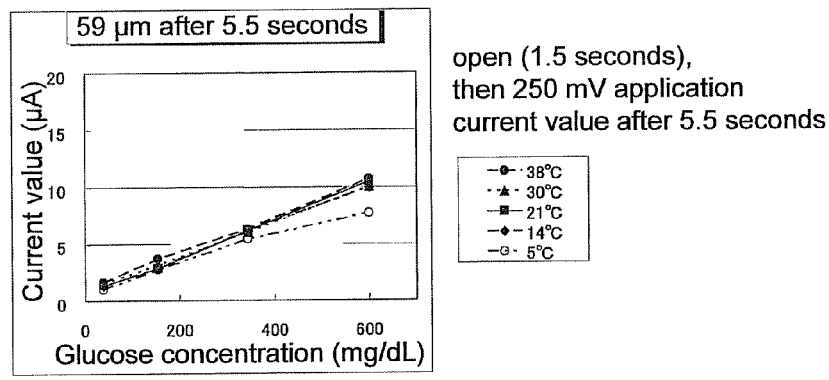
FIG. 27C is a graph of the relation between temperature, glucose concentration, and the current value when 5.5 seconds have elapsed (4 seconds after the start of application of a voltage of 250 mV), when the height of the capillary is 59 μm, on the basis of FIGS. 23C, 24C, 25C, and 26C.
Figure 27D:
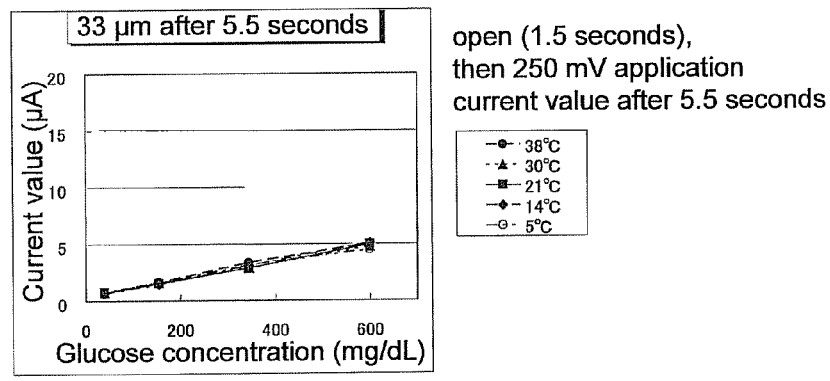
FIG. 27D is a graph of the relation between temperature, glucose concentration, and the current value when 5.5 seconds have elapsed (4 seconds after the start of application of a voltage of 250 mV), when the height of the capillary is 33 μm, on the basis of FIGS. 23D, 24D, 25D, and 26D.
Figure 28A:
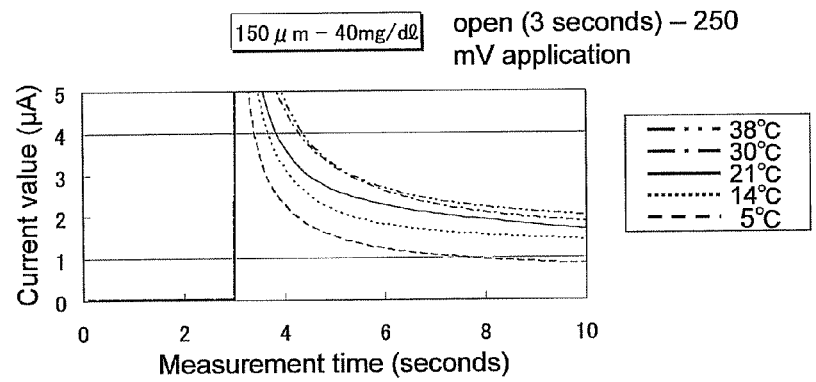
FIG. 28A is a graph of the response current value when the glucose concentration of the sample is 40 mg/dL, the voltage application conditions are open (3 seconds)—250 mV, and the height of the capillary is 150 μm.
Figure 28B:
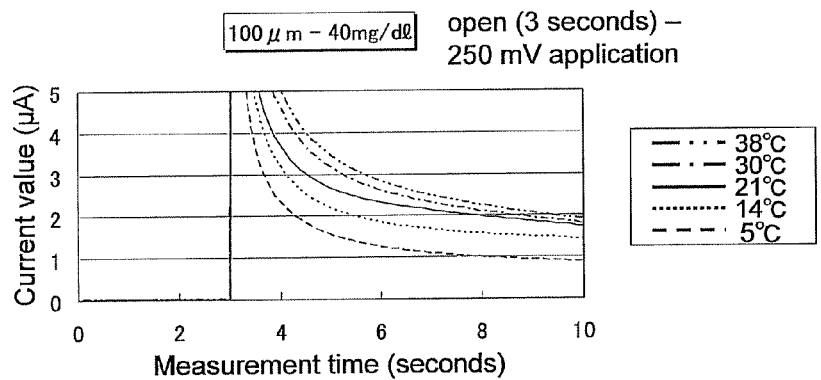
FIG. 28B is a graph of the response current value under the same conditions as in FIG. 28A, except that the height of the capillary is 100 μm.
Figure 28C:
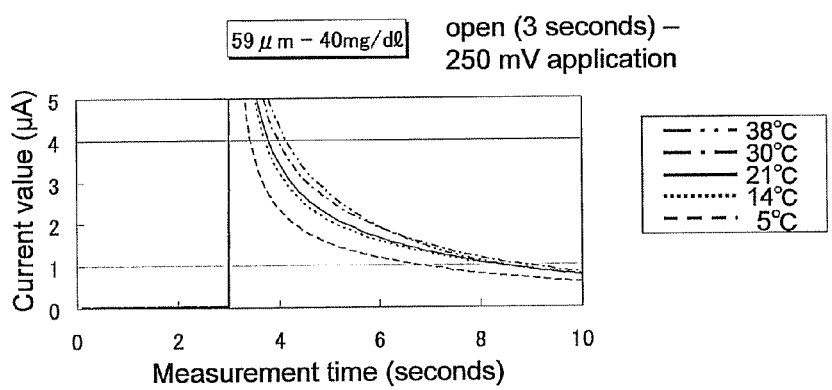
FIG. 28C is a graph of the response current value under the same conditions as in FIG. 28A, except that the height of the capillary is 59 μm.
Figure 28D:
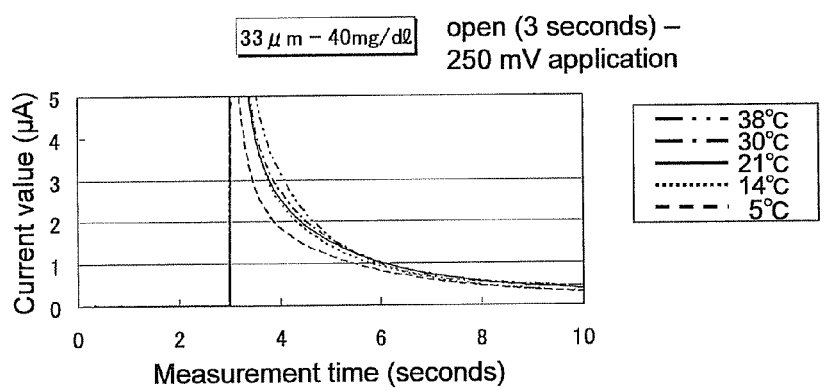
FIG. 28D is a graph of the response current value under the same conditions as in FIG. 28A, except that the height of the capillary is 33 μm.
Figure 29A:
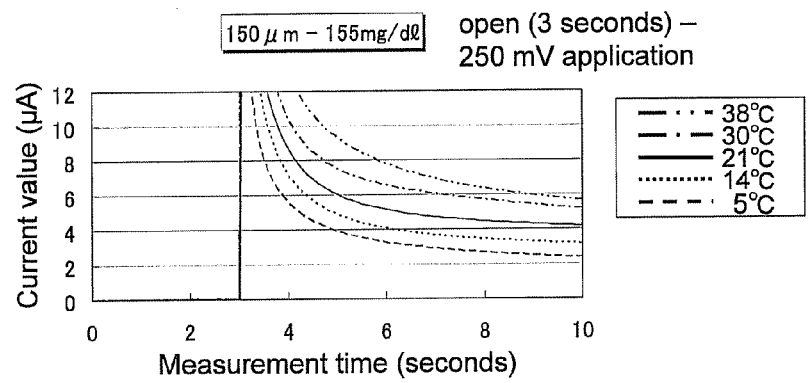
FIG. 29A is a graph of the response current value under the same conditions as in FIG. 28A (the voltage application conditions are open (3 seconds)—250 mV, and the height of the capillary is 150 μm), except that the glucose concentration of the sample is 155 mg/dL.
Figure 29B:
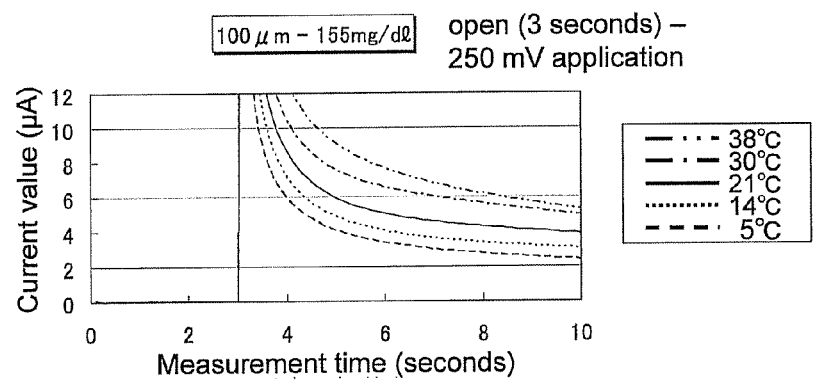
FIG. 29B is a graph of the response current value under the same conditions as in FIG. 29A, except that the height of the capillary is 100 μm.
Figure 29C:
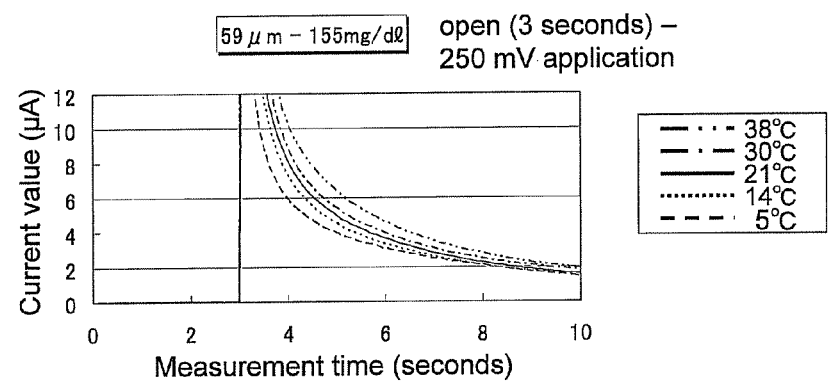
FIG. 29C is a graph of the response current value under the same conditions as in FIG. 29A, except that the height of the capillary is 59 μm.
Figure 29D:
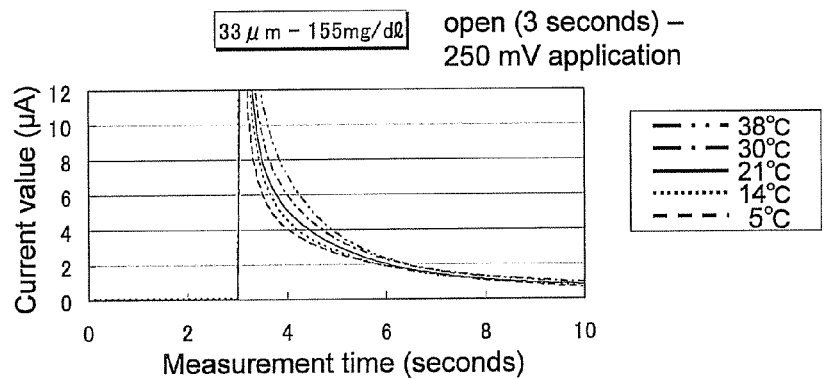
FIG. 29D is a graph of the response current value under the same conditions as in FIG. 29A, except that the height of the capillary is 33 μm.
Figure 30A:
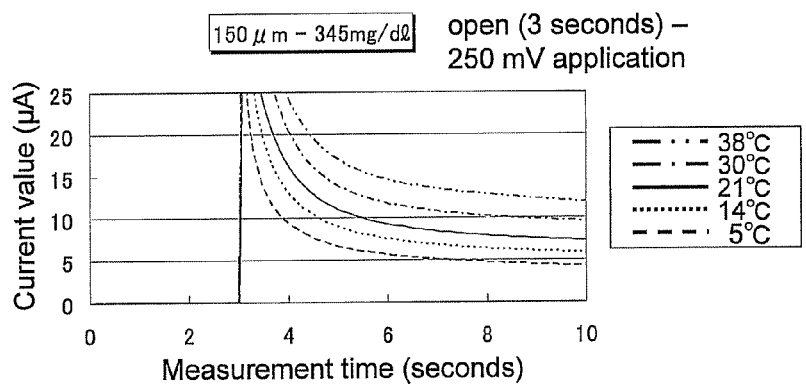
FIG. 30A is a graph of the response current value under the same conditions as in FIG. 28A (the voltage application conditions are open (3 seconds)—250 mV, and the height of the capillary is 150 μm), except that the glucose concentration of the sample is 345 mg/dL.
Figure 30B:
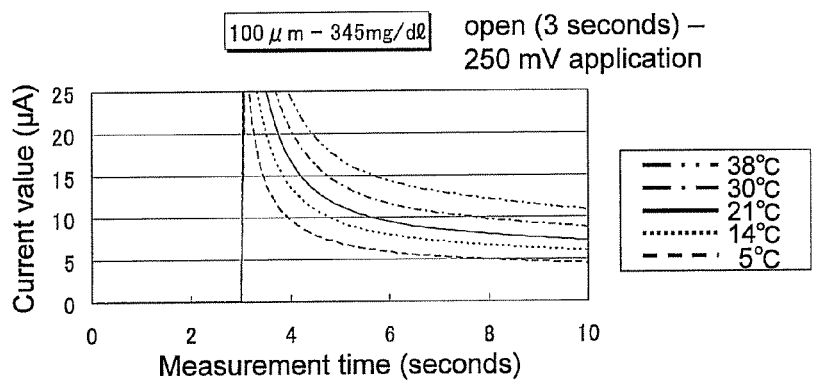
FIG. 30B is a graph of the response current value under the same conditions as in FIG. 30A, except that the height of the capillary is 100 μm.
Figure 30C:
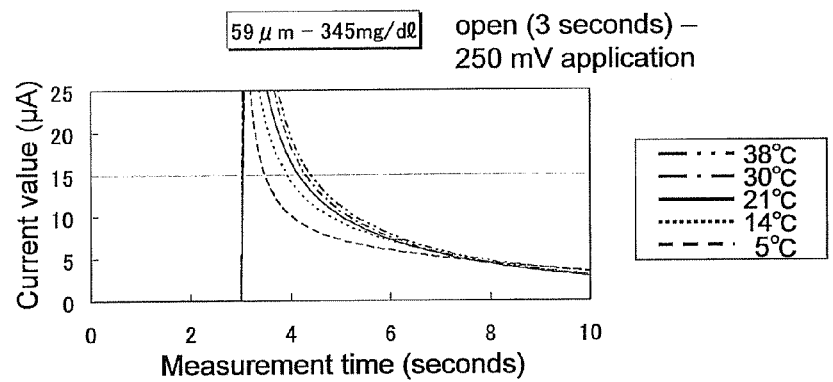
FIG. 30C is a graph of the response current value under the same conditions as in FIG. 30A, except that the height of the capillary is 59 μm.
Figure 30D:
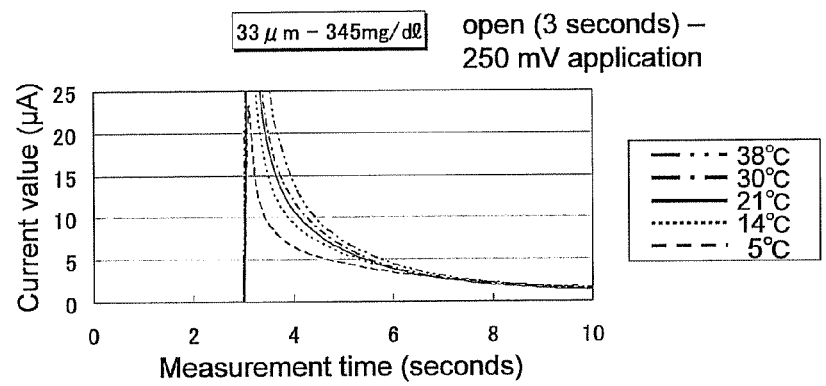
FIG. 30D is a graph of the response current value under the same conditions as in FIG. 30A, except that the height of the capillary is 33 μm.
Figure 31A:
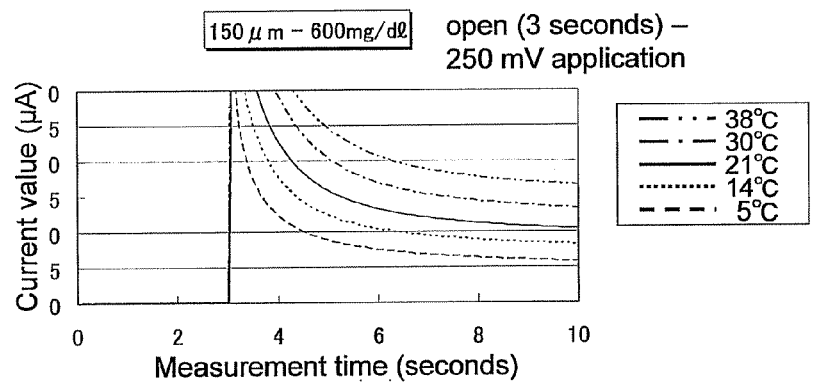
FIG. 31A is a graph of the response current value under the same conditions as in FIG. 28A (the voltage application conditions are open (3 seconds)—250 mV, and the height of the capillary is 150 μm), except that the glucose concentration of the sample is 600 mg/dL.
Figure 31B:
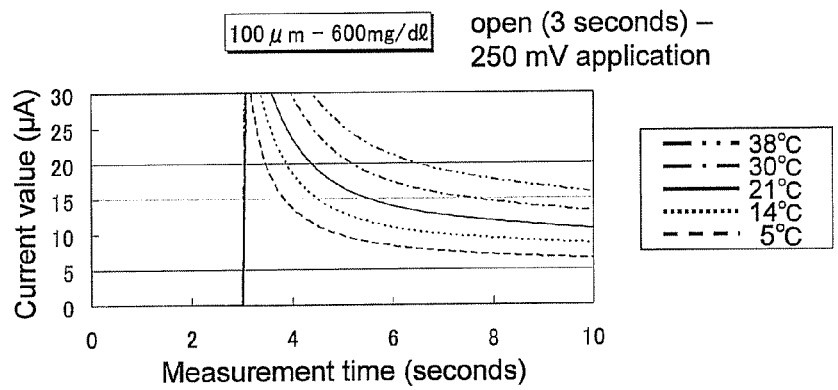
FIG. 31B is a graph of the response current value under the same conditions as in FIG. 31A, except that the height of the capillary is 100 μm.
Figure 31C:
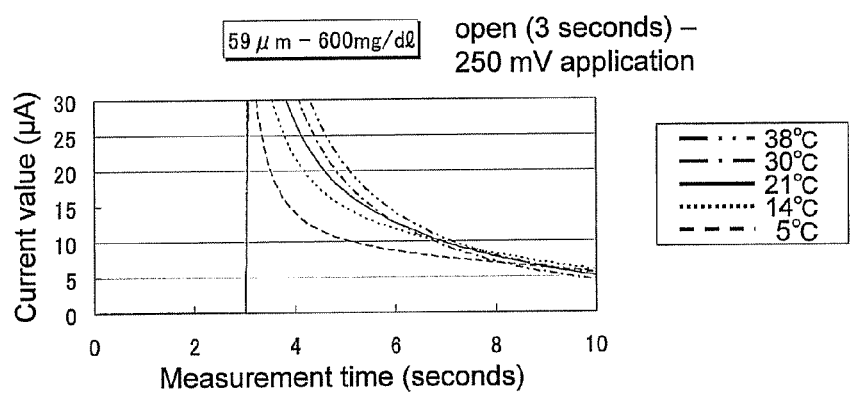
FIG. 31C is a graph of the response current value under the same conditions as in FIG. 31A, except that the height of the capillary is 59 μm.
Figure 31D:
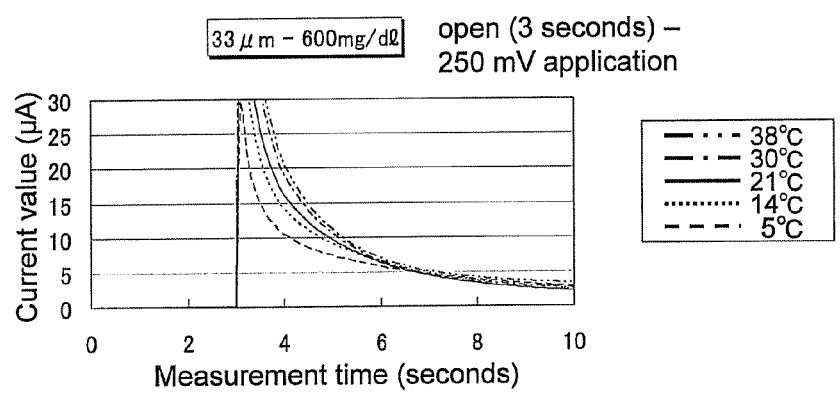
FIG. 31D is a graph of the response current value under the same conditions as in FIG. 31A, except that the height of the capillary is 33 μm.
Figure 32A:
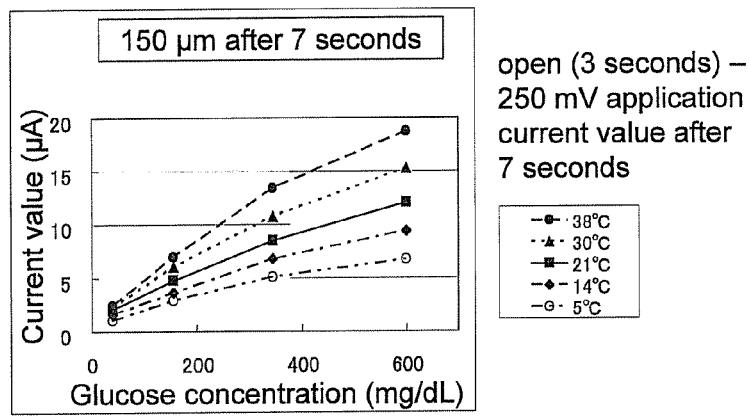
FIG. 32A is a graph of the relation between temperature, glucose concentration, and the current value when 7 seconds have elapsed (4 seconds after the start of application of a voltage of 250 mV), when the height of the capillary is 150 μm, on the basis of FIGS. 28A, 29A, 30A, and 31A.
Figure 32B:
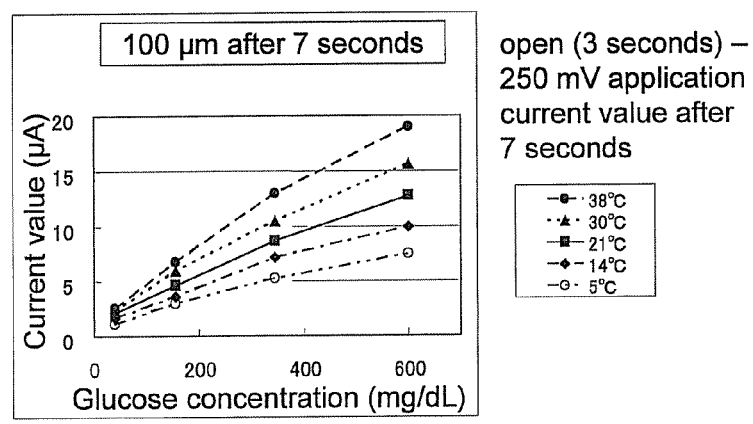
FIG. 32B is a graph of the relation between temperature, glucose concentration, and the current value when 7 seconds have elapsed (4 seconds after the start of application of a voltage of 250 mV), when the height of the capillary is 100 μm, on the basis of FIGS. 28B, 29B, 30B, and 31B.
Figure 32C:
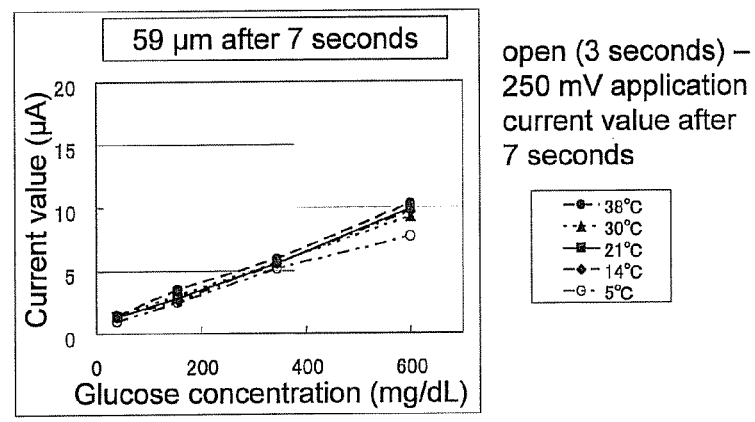
FIG. 32C is a graph of the relation between temperature, glucose concentration, and the current value when 7 seconds have elapsed (4 seconds after the start of application of a voltage of 250 mV), when the height of the capillary is 59 μm, on the basis of FIGS. 28C, 29C, 30C, and 31C.
Figure 32D:
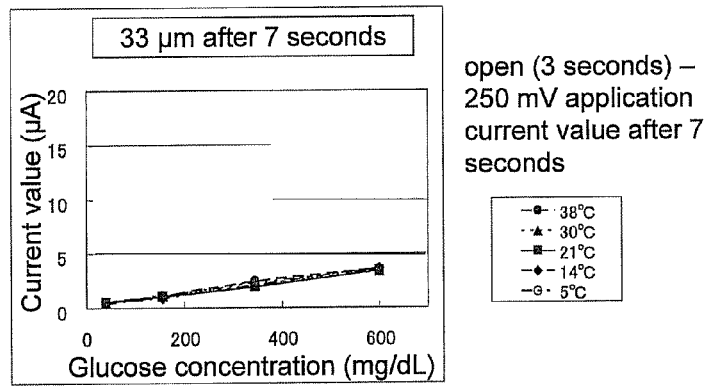
FIG. 32D is a graph of the relation between temperature, glucose concentration, and the current value when 7 seconds have elapsed (4 seconds after the start of application of a voltage of 250 mV), when the height of the capillary is 33 μm, on the basis of FIGS. 28D, 29D, 30D, and 31D.

FIG. 20A is a graph of the current value at a point when 8 seconds had elapsed in FIGS. 19A to 19D (a point when 3 seconds had elapsed after the start of the voltage application of 250 mV). FIG. 20B is a graph of the variance in the current value at various temperatures when the current value at 21° C. in FIG. 20A was used as a reference value (0%).

As shown in FIGS. 20A and 20B, when the height H is 59 μm, the variance due to temperature was kept to less than ±20%. When the height H was 33 μm, the variance was kept to let than ±10%.

The same experiment was conducted using a sample in which the glucose concentration was 400 mg/dL. As shown in FIGS. 21A to 21D and FIGS. 22A to 22B, even when the glucose concentration in the sample was high, the variance was kept small when the height H was 59 µm or less, and particularly when it was 33 µm.

As discussed above, if the height H of the capillary is merely reduced, inversion will occur between the current value at high temperature and the current value at low temperature as the measurement time passes, and variance in the current value due to differences in temperature will not be suppressed.

In contrast, in this experiment example, the mediator is maintained in a state in which no electrons are transmitted to the working electrode 11 inside the capillary 40, by having the applied voltage be open circuit voltage for 5 seconds after the start of the enzyme reaction. Since the enzyme reaction proceeds during this time as well, electrons are accumulated in the mediator. After this, the measurement voltage $V_{mes}$ is applied and the concentration measured at the point when electrons were accumulated. As a result, the current value during concentration measurement is the sum of adding the amount of reaction during the application of the open circuit voltage to the amount of reaction during the application of the measurement voltage $V_{mes}$. As a result, it is believed that fluctuation in the measured value caused by the environment temperature during measurement was kept small.

Experiment Example 4

In this experiment example, it was confirmed that the same effect as in Experiment Example 3 can be obtained even when the open circuit voltage is applied for a different length of time. In this experiment example, the duration of application of the open circuit voltage was 1.5 seconds or 3 seconds. Also, the glucose concentration was 40 mg/dL, 155 mg/dL, 345 mg/dL, or 600 mg/dL. In FIGS. 23A to 23D, FIGS. 24A to 24D, FIGS. 25A to 25D, and FIGS. 26A to 26D, the duration of application of the open circuit voltage is 1.5 seconds. In FIGS. 28A to 28D, FIGS. 29A to 29D, FIGS. 30A to 30D, and FIGS. 31A to 31D, the duration of application of the open circuit voltage is 3 seconds. In all of these drawings, the operation that was carried out is the same except that the glucose concentration is different.

As shown in FIGS. 23A to 23D, FIGS. 24A to 24D, FIGS. 25A to 25D, FIGS. 26A to 26D, FIGS. 28A to 28D, FIGS. 29A to 29D, FIGS. 30A to 30D, and FIGS. 31A to 31D, even when there is a change in the glucose concentration and/or the open circuit voltage application duration, variance in the current value due to temperature was small when the height H was 59 µm or less, and particularly when it was 33 µm.

Also, as shown in FIGS. 27A to 27D, when the height H was 59 µm or less, the current value was not affected greatly by temperature. That is, accurate measurement results were obtained, with little error due to temperature. In particular, variance was extremely small when the height was 33 µm. If variance is small, then even if the temperature is different, the concentration can be calculated from a single calibration curve. As shown in FIGS. 32A to 32D, the same results were observed for the current value at the point when 7 seconds had elapsed in FIG. 29 (the measurement results when the open circuit voltage application duration was 3 seconds and the glucose concentration was 155 mg/dL).

Experiment Example 5

In the following Experiment Examples 5 to 9, the glucose concentration is 100 mg/dL.

In Experiment Example 5, the response current value was measured when the height H of the sensor chip is 150, 104, 90, 82, 69, 59, 49, or 33 µm, the duration of application of the open circuit voltage was 0, 1, 1.5, 2, 3, 4, 5, 6, or 7 seconds, and the 250 mV measurement voltage was applied after the application of the open circuit voltage.

When FIGS. 33A to 34D, which show the results when no open circuit voltage was applied (when the application duration was 0 seconds), are compared to FIGS. 35A to 36D, which show the results when an open circuit voltage was applied, it can be seen that variance in the current value due to temperature was kept smaller when the open circuit voltage was applied. This effect is more pronounced when the open circuit voltage was applied for at least 1.5 seconds, and even more so when the application was for at least 2 seconds.

Data is shown in the drawings for when the open circuit voltage was applied for up to 5 seconds, but variance in the current value due to temperature was similarly kept small when the application length was 6 or 7 seconds.

Experiment Example 6

The height H of the sensor chip was 150, 104, 90, 82, 69, 59, 49, or 33 µm. The duration of application of the open circuit voltage was 0 or 2 seconds. The response current value was measured for when the 250 mV measurement voltage was applied after the application of the open circuit voltage.

Under the various conditions, the current value was measured at 5° C., 14° C., 21° C., 30° C., and 38° C., and the discrepancy (variance) in the result obtained at each temperature from the measurement result at 21° C. was calculated. In FIGS. 47A to 50D, the discrepancy when the height H is 150 µm is expressed by a broken line, and the discrepancy when the height H is 104, 90, 82, 69, 59, 49, or 33 µm is expressed by a solid line.

That is, the solid-line curve at the top in FIG. 49A shows how much the current value obtained when a measurement voltage of 250 mV was applied after the application of an open circuit voltage for 2 seconds (open duration) at 38° C., with a sensor chip having a height H of 104 µm, deviates from the current value measured at 21° C. (measured under the same conditions except for the temperature). That is, the closer the solid line is to the 0% horizontal axis, the smaller is the variance. The broken line at the top in this same drawing shows how much the current value measured at a height H of 150 µm and 38° C. deviates from the current value measured at 21° C.

As shown in FIGS. 47A to 50C, when the open circuit voltage application duration was 2 seconds, the variance due to temperature was kept smaller than when the duration was 0 seconds.

As shown in FIGS. 49A to 49D and FIGS. 50A to 50C, the variance in current value when the height H is 104 µm is quite different from the variance in current value when the height H is 150 µm (FIG. 49A). In contrast, when the height H is 90 µm or less, the variance in current value due to temperature was kept smaller than when the height H was 104 µm (FIG. 49B, etc.). Specifically, the height H of the capillary is preferably 90 µm or less.

Although not shown in the data graphs, the variance was similarly kept small when the open circuit voltage application duration was 3 to 5 seconds.

Experiment Example 7

In this experiment example, a measurement voltage of 250 mV was applied after a voltage of 100 mV had been applied for 3 seconds to sensor chips of different heights H. The heights H were 150, 104, 90, 82, 69, 59, 49, and 33 µm.

As shown in FIGS. 51A to 51D and FIGS. 52A to 52D, this experiment example makes it clear that there is still a variance suppression effect even when a voltage that is lower than the measurement voltage is applied instead of an open circuit voltage. The variance suppression effect was particularly pronounced when the height H was 59 µm or less.

Experiment Example 8

In this experiment example, a measurement voltage of 250 mV was applied after a voltage of 0 mV had been applied for 3 seconds to sensor chips of different heights H. The heights H were the same as in Experiment Example 7.

As shown in FIGS. 53A to 53D and FIGS. 54A to 54D, there is still a variance suppression effect even when a voltage of 0 mV is applied instead of an open circuit voltage. The variance suppression effect was particularly pronounced when the height H was 59 µm or less.

Experiment Example 9

In this experiment example, a measurement voltage of 250 mV was applied after a voltage of 250 mV had first been applied for 1 second to sensor chips of different heights H, followed by the application of an open circuit voltage for 2 seconds. The heights H were the same as in Experiment Example 7.

As shown in FIGS. 55A to 55D and FIGS. 56A to 56D, there is still a variance suppression effect even when a closed circuit voltage is applied prior to the application of an open circuit voltage. The variance suppression effect was particularly pronounced when the height H was 59 µm or less.

Furthermore, it was confirmed that if an open circuit voltage is applied and/or a voltage lower than the measurement voltage is applied after the application of a voltage higher than the measurement voltage, there was less variance due to temperature in the current value obtained when measurement voltage was applied subsequently to this.

INDUSTRIAL APPLICABILITY

The sensor chip, the biosensor system comprising this sensor chip, the method for measuring the temperature of a biological sample, and the concentration measurement method of the present invention all have the effect of allowing concentration measurement error attributable to temperature to be effectively suppressed, and therefore can be widely applied in various fields that require more accurate measurement.

REFERENCE SIGNS LIST

11 working electrode (electrode)
12 counter electrode (electrode)
13 detection electrode
16 air vent
17 introduction port
20 reagent layer
40 capillary
100 biosensor system
101 measurement device
102 mounting opening
103 display section
200 sensor chip
201 insulated board
202 spacer
203 cover
204 cut-out
300 control circuit
301a, 301b, 301c connector
302 switching circuit
303 current/voltage conversion circuit
304 analog/digital (A/D) conversion circuit
305 reference voltage source (first voltage applicator, second voltage applicator)
306 computer (concentration measurement section, first voltage applicator, second voltage applicator)

The invention claimed is:

1. A biosensor system, with which the concentration of an analyte in a liquid sample is measured using a redox enzyme and a potassium ferricyanide as an electron-transfer mediator, said biosensor system comprising:
    a sensor chip having a capillary into which a liquid sample is introduced, a plurality of electrodes disposed within the capillary, and a reagent layer that is disposed within the capillary and includes the electron-transfer mediator;
    the capillary having a height less than the maximum value of the sum of the diffusion distance of the electron-transfer mediator and the diffusion distance of the analyte at an upper temperature limit for which the biosensor system is functional;
    the plurality of electrodes including a working electrode and a counter electrode; and
    the plurality of electrodes are disposed so as to be opposite each other in a horizontal plane;
    a voltage applicator that
        applies a measurement voltage to the working electrode and the counter electrode,
        applies a second voltage of positive polarity to the working electrode and the counter electrode prior to the application of the measurement voltage, so that the effect of the temperature of the liquid sample on the measurement results of the concentration measurement section will be diminished, and
        applies a first voltage to the working electrode and the counter electrode prior to the application of the second voltage,
        wherein the second voltage is positive with respect to a ground used when applying the measurement voltage, and
        wherein the second voltage is lower than the measurement voltage;
    a concentration measurement section that measures the concentration of the analyte on the basis of the value of the current flowing through the liquid sample during the measurement voltage application; and
    wherein the height of the capillary of the sensor chip is the distance from the working electrode to an opposite face from the working electrode, and the height of the capillary of the sensor chip is between 49 and 90 µm.

2. The biosensor system according to claim 1,
    wherein the height of the capillary of the sensor chip is less than the maximum value of the sum of the diffusion distance of the electron-transfer mediator and the diffusion distance of the analyte, found from a lower temperature limit for which biosensor system is functional.

3. The biosensor system according to claim 1,
    wherein the voltage applicator accumulates electrons in the electron-transfer mediator by applying the second voltage.

4. The biosensor system according to claim 1,
wherein the voltage applicator applies an open circuit voltage as the second voltage.

5. The biosensor system according to claim 1,
wherein the concentration measurement section has a calibration curve or table that correlates the current value and the analyte concentration, and calculates the analyte concentration on the basis of the same calibration curve or table even if the temperature of the liquid sample should fluctuate.

6. The biosensor system according to claim 1,
wherein the concentration measurement section measures the analyte concentration on the basis of the current value at a point when no more than 10 seconds have elapsed since the start of the application of the second voltage.

7. The biosensor system according to claim 1,
wherein the electrodes are disposed on two faces that are mutually opposite in the height direction of the capillary.

8. The biosensor system according to claim 1,
wherein the second voltage is smaller than the measurement voltage, and
the first voltage is bigger than the second voltage.

9. The biosensor system according to claim 1,
wherein the height of the capillary of the sensor chip is between 49 and 59 μm.

* * * * *